US008084258B2

(12) United States Patent
Gehring et al.

(10) Patent No.: US 8,084,258 B2
(45) Date of Patent: Dec. 27, 2011

(54) MANIPULATION OF TISSUE OF ORGAN TYPE USING THE NOTCH PATHWAY

(75) Inventors: Walter Gehring, Therwil (CH); Spyridon Artavanis-Tsakonas, Brookline, MA (US)

(73) Assignees: University of Basel, Basel (CH); Yale University, New Haven, CT (US)

( * ) Notice: Subject to any disclaimer, the term of this patent is extended or adjusted under 35 U.S.C. 154(b) by 1056 days.

(21) Appl. No.: 10/751,908

(22) Filed: Jan. 5, 2004

(65) Prior Publication Data

US 2004/0242482 A1 Dec. 2, 2004

Related U.S. Application Data

(63) Continuation of application No. 09/614,003, filed on Jul. 11, 2000, now abandoned.

(60) Provisional application No. 60/143,484, filed on Jul. 12, 1999.

(51) Int. Cl.
*C12N 5/00* (2006.01)
(52) U.S. Cl. ........ 435/377; 435/455; 530/358; 536/24.1; 536/24.5
(58) Field of Classification Search .................. None
See application file for complete search history.

(56) References Cited

U.S. PATENT DOCUMENTS

| | | | |
|---|---|---|---|
| 5,115,096 A | 5/1992 | Shoyab et al. |
| 5,132,212 A | 7/1992 | Kirsch et al. |
| 5,226,914 A | 7/1993 | Caplan et al. |
| 5,264,557 A | 11/1993 | Salomon et al. |
| 5,635,177 A | 6/1997 | Bennett et al. |
| 5,648,464 A | 7/1997 | Artavanis-Tsakonas et al. |
| 5,780,300 A | 7/1998 | Artavanis-Tsakonas et al. |
| 5,786,158 A | 7/1998 | Artavanis-Tsakonas et al. |
| 5,789,195 A | 8/1998 | Artavanis-Tsakonas et al. |
| 5,849,869 A | 12/1998 | Artavanis-Tsakonas et al. |
| 5,856,441 A | 1/1999 | Artavanis-Tsakonas et al. |
| 5,869,282 A | 2/1999 | Ish-Horowicz et al. |
| 6,004,924 A | 12/1999 | Ish-Horowicz et al. |
| 6,083,904 A | 7/2000 | Artavanis-Tsakonas et al. |
| 6,149,902 A | 11/2000 | Artavanis-Tsakonas et al. |
| 6,262,025 B1 | 7/2001 | Ish-Horowicz et al. |
| 6,337,387 B1 | 1/2002 | Sakano et al. |
| 6,436,650 B1 | 8/2002 | Artavanis-Tsakonas et al. |
| 6,692,919 B1 | 2/2004 | Artavanis-Tsakonas et al. |
| 6,783,956 B2 | 8/2004 | Ish-Horowicz et al. |
| 7,118,890 B2 | 10/2006 | Ish-Horowicz et al. |
| 2004/0058443 A1 | 3/2004 | Artavanis-Tsakonas et al. |
| 2005/0112121 A1 | 5/2005 | Artavanis-Tsakonas et al. |
| 2007/0003983 A1 | 1/2007 | Artavanis-Tsakonas et al. |
| 2007/0082846 A1 | 4/2007 | Ish-Horowicz et al. |
| 2007/0134239 A1 | 6/2007 | Ish-Horowicz et al. |

FOREIGN PATENT DOCUMENTS

| | | |
|---|---|---|
| WO | WO 92/19734 | 11/1992 |
| WO | WO 94/07474 | 4/1994 |
| WO | WO 94/13701 | 6/1994 |
| WO | WO95/027062 | 10/1995 |
| WO | WO 98/48829 | 11/1998 |

OTHER PUBLICATIONS

Blaumueller et al., Cell, vol. 90, 1997, pp. 281-291.*
Fleming et al., Trends in Cell Biology, vol. 7, 1997, pp. 437-441.*
Branch, TIBS, vol. 23 (1998) pp. 45-50.*
U.S. Appl. No. 10/746,237, filed Jul. 21, 2005, Artavanis-Tsakonas et al.
U.S. Appl. No. 11/605,536, filed Jul. 19, 2007, Artavanis-Tsakonas et al.
Ahmad et al., 1995, "Involvement of Notch-1 in mammalian retinal neurogenesis: association of Notch-1 activity with both immature and terminally differentiated cells." Mech Dev. 53(1):73-85.
Artavanis-Tsakonas et al., 1999, "Notch signaling: cell fate control and signal integration in development", Science 284:770-776.
Campos-Ortega et al., 1990, "Molecular analysis of a cellular decision during embryonic development of Drosophila melanogaster: epidermogenesis or neurogenesis." Eur J Biochem. 190(1):1-10.
Czerny et al., 1999, "Twin of eyeless, a second Pax-6 gene of Drosophila, acts upstream of eyeless in the control of eye development", Mol. Cell 3:297-307.
de Celis et al., 1993, "Genetic and molecular characterization of a Notch mutation in its Delta- and Serrate-binding domain in Drosophila." Proc Natl Acad Sci U S A. 90(9):4037-41.

(Continued)

*Primary Examiner* — Jim Ketter
(74) *Attorney, Agent, or Firm* — Jones Day

(57) ABSTRACT

The present invention is directed to methods for altering the fate of a cell, tissue or organ type by altering Notch pathway function in the cell. The invention is further directed to methods for altering the fate of a cell, tissue or organ type by simultaneously changing the activation state of the Notch pathway and one or more cell fate control gene pathways. The invention can be utilized for cells of any differentiation state. The resulting cells may be expanded and used in cell replacement therapy to repopulate lost cell populations and help in the regeneration of diseased and/or injured tissues. The resulting cell populations can also be made recombinant and used for gene therapy or as tissue/organ models for research. The invention is directed to methods for of treating macular degeneration comprising altering Notch pathway function in retinal pigment epithelium cells or retinal neuroepithelium or both tissues. The present invention is also directed to kits utilizing the methods of the invention to generate cells, tissues or organs of altered fates. The invention also provides methods for screening for agonists or antagonists of Notch or cell fate control gene pathway functions.

23 Claims, 9 Drawing Sheets

OTHER PUBLICATIONS

Figures 2A, 2B:
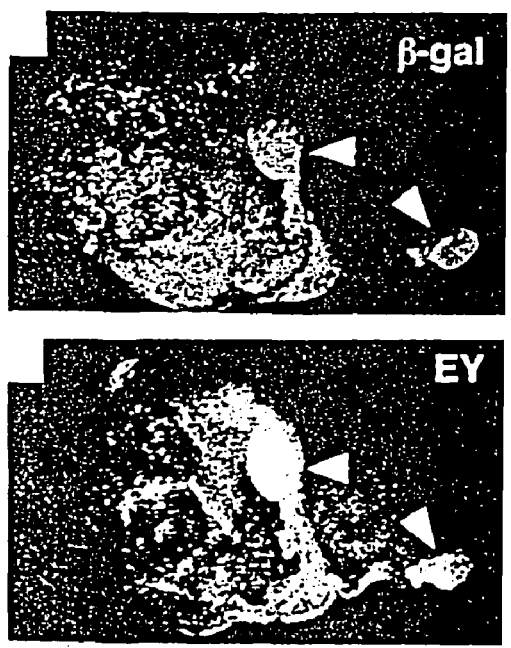

Eggert et al., 1998, "Isolation of a Drosophila homolog of the vertebrate homeobox gene Rx and its possible role in brain and eye development", Proc. Natl. Acad. Sci. USA, 5:2343-48.

Ellisen et al., 1991, "TAN-1, the human homolog of the Drosophila notch gene, is broken by chromosomal translocations in T lymphoblastic neoplasms." Cell. 66(4):649-61.

Fleming et al., 1997, "The NOTCH receptor and its ligands." Trends Cell Biol. 7(11): 437-441.

Fortini et al., 1992, "Signalling by the sevenless protein tyrosine kinase is mimicked by Ras1 activation."Nature. 355(6360):559-61.

Fortini et al., 1993, "An activated Notch receptor blocks cell-fate commitment in the developing Drosophila eye", Nature 365:555-57.

Go et al., 1998, "Cell proliferation control by Notch signaling in Drosophila development", Development 125:2031-40.

Greenspan, 1990, "The Notch gene, adhesion, and developmental fate in the Drosophila embryo." New Biol. 2(7):595-600.

Greenwald, 1994, "Structure/function studies of lin-12/Notch proteins", Curr Opin Genet Dev. 4:556-62.

Halder et al., 1995, "Induction of Ectopic Eyes by Targeted Expression of the eyeless Gene in Drosophila", Science 267:1788-92.

Hukriede et al., 1997, "A dominant-negative form of Serrate acts as a general antagonist of Notch activation", Development 124(7):3427-37.

Nusse et al., 1992, "Wnt genes." Cell. 69(7):1073-87.

Quiring et al., 1994, "Homology of the eyeless gene of Drosophila to the Small eye gene in mice and Aniridia in humans", Science 265:785-9.

Rebay et al., 1991, Specific EGF repeats of Notch mediate interactions with Delta and Serrate: implications for Notch as a multifunctional receptor. Cell. 67(4):687-99.

Robbins et al., 1992, "Mouse mammary tumor gene int-3: a member of the notch gene family transforms mammary epithelial cells." J Virol. 66(4):2594-9.

Roehl et al., 1993, "Control of cell fate in C. elegans by a GLP-1 peptide consisting primarily of ankyrin repeats." Nature 364:632-5.

Struhl et al. 1993, "Intrinsic activity of the Lin-12 and Notch intracellular domains in vivo." Cell. 74(2):331-45.

Sun et al., 1997, "Evolution of paired domains: isolation and sequencing of jellyfish and hydra Pax genes related to Pax-5 and Pax-6." Proc. Natl. Acad. Sci. USA 94:5156-5161.

Sun and Artavanis-Tsakonas, 1997, "Secreted forms of DELTA and SERRATE define antagonists of Notch signaling in Drosophila." Development 124:3439-48.

Sun et al., 1996, "The intracellular deletions of DELTA and SERRATE define dominant negative forms of the Drosophila Notch ligands." Development 122:2465-2474.

Artavanis-Tsakonas and Simpson, 1991, "Choosing a cell fate: a view from the Notch locus." Trends in Genetics 7:403-408.

Artavanis-Tsakonas et al., 1991, "The Notch locus and the cell biology of neuroblast segregation." Ann. Rev. Cell Biol. 7:427-452.

Artavanis-Tsakonas et al., 1995, "Notch signaling." Science 268:225-232.

Berezovska et al., 1999, "Notch 1 inhibits neurite outgrowth in postmitotic primary neurons." Neuroscience 93(2):433-439.

Briend et al., 2005, "Modulation of the notch pathway for immunotherapy." Curr. Opin. Mol. Therapeutics 7(1):56-61.

Büchler et al., 2005, "The Notch signaling pathway is related to neurovascular progression of pancreatic cancer" Ann. Surg. 242:791.

Chigurupati et al., 2007, "Involvement of notch signaling in wound healing." PloS ONE 2(11):e1167.

Coffman et al., 1990, "Xotch, the Xenopus homolog of Drosophila notch." Science 249:1438-1441.

Dang et al., 2003, "Constitutive activation of Notch3 inhibits terminal epithelial differentiation in lungs of transgenic mice." Oncogene 22:1988.

Decision to Refuse a European Patent Application, from EP Application No. 99933914.3-2107, dated May 3, 2007.

Dontu et al., 2004, "Role of Notch signaling in cell-fate determination of human mammary stem/progenitor cells." Breast Cancer Res. 64:R605-R615.

Farnie et al., 2007, "Novel cell culture technique for primary ductal carcinoma in situ: role of Notch and epidermal growth factor receptor signaling pathways." J. Natl. Cancer Inst. 99:616-627.

Farnie et al., 2007, "Mammary stem cells and breast cancer—role of Notch signaling." Stem Cell Rev. 3:169-175.

Fehon et al., 1990, "Molecular interactions between the protein products of the neurogenic loci Notch and Delta, two EGF-homologous genes in Drosophila." Cell 61:523-534.

Fre et al., 2005, "Notch signals control the fate of immature progenitor cells in the intestine." Nature 435:964.

Garces, 1997, "Notch-1 controls the expression of fatty acid-activated transcription factors and is required for adipogenesis." J. Biol. Chem. 272(47):29729.

Gerhart, 1999, "1998 Warkany lecture: signaling pathways in development." Teratology 60:226-239.

Harper et al., 2003, "Notch signaling in development and disease." Clin. Genet 64:461.

Hayashi et al., 2004, "Expression failure of the notch signaling system is associated with the pathogenesis of testicular germ cell tumor." Tumor Biology 25:99.

Hetts et al., 1998, "To die or not to die: an overview of apoptosis and its role in disease." JAMA 279(4): 300-307.

Hoek et al., 2004, "Expression profiling reveals novel pathways in the transformation of melanocytes to melanomas." Cancer Research 64:5270.

Jang et al., 2000, "Notch signaling as a target in multimodality cancer therapy." Curr. Opin. Mol. Therapeutics 2(1):55.

Jundt et al., 2002, "Activated Notch 1 signaling promotes tumor cell proliferation and survival in Hodgkin and anaplastic large cell lymphoma." Blood 99(9):3398.

Kiaris et al., 2004, "Modulation of notch signaling elicits signature tumors and inhibits hras1-induced oncogenesis in the mouse mammary epithelium." Am. J. Pathology 165:695.

Kogoshi et al., 2007, "Gamma-secretase inhibitors suppress the growth of leukemia and lymphoma cells." Oncology Reports 18:77-80.

Konishi et al., 2007, "Gamma-secretase inhibitor prevents Notch3 activation and reduces proliferation in human lung cancers." Cancer Res. 67:8051-8057.

Kopan et al., 1994, "The intracellular domain of mouse Notch: a constitutively activated repressor of myogenesis directed at the basic helix-loop-helix region of MyoD." Development 120:2385.

Krop et al., 2006, Abstract 6097, Breast Cancer Research and Treatment 100:Supplement 1.

Li et al., 1997, "Alagille syndrome is caused by mutations in human Jagged1, which encodes a ligans for Notch1." Nature Genetics 16:243.

Li et al., 2008, "Modulation of Notch Signaling by Antibodies specific for the extracellular negative regulatory region of notch3" J. Biol. Chem. 283:8046-8054.

Lindsell et al., 1995, "Jagged: a mammalian ligand that activates Notch1 ." Cell 80:909-917.

Louvi and Artavanis-Tsakonas, 2006, "Notch signaling in Vertebrate Neural development" Notch Signaling in Neuronal Development , Nature Neuro. Reviews 7:93.

Malicki et al., 1990, "Mouse Hox-2.2 specifies thoracic segmental identity in Drosophila embryos and larvae." Cell 63:961-967.

Miele et al., 2006, "NOTCH signaling as a novel cancer therapeutic target." Curr. Cancer Drug Targets 6:313.

Nam et al., 2002, "Notch signaling as a therapeutic target."Curr. Opin. Chem. Biol. 6:501.

Nijjar et al., 2002, "Altered Notch ligand expression in human liver disease: further evidence for a role of the Notch signaling pathway in hepatic neovascularization and biliary ductular defects." Am. J. Pathology 160(5):1695.

Nye et al., 1994, "An activated Notch suppresses neurogenesis and myogenesis but not gliogenesis in mammalian cells." Development 120:2421.

Oda et al., 1997, "Mutations in the human Jagged1 gene are responsible for Alagille syndrome." Nature Genetics 16:235.

Onuma et al., 2002, "Conservation of Pax 6 function and upstream activation by Notch signaling in eye development of frogs and flies." Proc. Natl. Acad. Sci. U.S.A. 99:2020-2025.

Park et al 2006, "Notch3 gene amplification in ovarian cancer." Cancer Res. 66:6312-6318.
Patel et al., 2005, "Up-regulation of delta-like 4 ligand in human tumor vasculature and the role of basal expression in endothelial cell function." Cancer Res. 65(19):8690.
Politi et al., 2004, "Notch in mammary gland development and breast cancer." Sem. Cancer Biol. 14:341-347.
Pui et al., 1999, "Notch 1 expression in early lymphopoiesis influences B versus T lineage determination." Immunity 11:299.
Purow et al., 2005, "Expression of Notch-1 and its ligands, Delta-like-1 and Jagged-1, is critical for glioma cell survival and proliferation." Cancer Res. 65(6):2353.
Qi et al., 1999, "Processing of the notch ligand delta by the metalloprotease Kuzbanian." Science 283:91-94.
Rebay et al., 1993, "Specific truncations of Drosophila Notch define dominant activated and dominant negative forms of the receptor." Cell 74:319-329.
Reedijk et al., 2005 "High-level coexpression of JAG 1 and NOTCH 1 is observed in human breast cancer and is associated with poor overall survival." Cancer Res. 65(18):8530-8537.
Robey et al., 1996, "An activated form of Notch influences the choice between CD4 and CD8 T cell lineages." Cell 87:483.
Rones et al., 2000, "Serrate and Notch specify cell fates in the heart field by suppressing cardiomyogenesis." Development 127:3865.
Santagata et al., 2004, "Jagged1 expression is associated with prostate cancer metastasis and recurrence." Cancer Res. 64:6854.
Sestan et al., 1999, "Contact-dependent inhibition of cortical neurite growth mediated by notch signaling." Science 286:741-746.
Sriuranpong et al., 2001, "Notch signaling induces cell cycle arrest in small cell lung cancer cells." Cancer Research 61:3200.
Stallwood et al., 2006, "Small interfering RNA-mediated knockdown of notch ligands in primary CD4+ T cells and dendritic cells enhances cytokine production." J. Immunol. 177:885-895.
Tomarev et al., 1997, "Squid Pax-6 and eye development." Proc. Natl. Acad. Sci. U.S.A. 94:2421.
Varnum-Finney et al., 1998, "The Notch ligand, Jagged-1, influences the development of primitive hematopoietic precursor cells." Blood 91(11):4084-4091.
Veeraraghavalu et al., 2004, "Papillomavirus-mediated neoplastic progression is associated with reciprocal changes in JAGGED1 and manic fringe expression linked to notch activation." J. Virology 78:8687.
Washburn et al., 1997, "Notch activity influences the alphabeta versus gammadelta T cell lineage decision." Cell 88:833.
Weinmaster et al., 1992, "Notch2: a second mammalian Notch gene." Develop. 116:931-941.
Zhao et al., 1993, "The mouse Hox-1.3 gene is functionally equivalent to the Drosophila Sex combs reduced gene." Genes & Develop. 7:343-354.
Office Action of U.S. Appl. No. 08/532,384, filed Sep. 22, 1995, dated Mar. 18, 1999.
Office Action of U.S. Appl. No. 08/532,384, filed Sep. 22, 1995, dated Jun. 23, 1998.
Office Action of U.S. Appl. No. 09/614,003, filed Jun. 11, 2000, dated Mar, 11, 2002.
Office Action of U.S. Appl. No. 09/614,003, filed Jun. 11, 2000, dated Dec. 3, 2002.
Office Action of U.S. Appl. No. 09/783,931, filed Feb. 15, 2001, dated Mar. 9, 2004.
Office Action of U.S. Appl. No. 09/783,931, filed Feb. 15, 2001, dated Jul. 25, 2005.
Office Action of U.S. Appl. No. 09/783,931, filed Feb. 15, 2001, dated Nov. 30, 2004.
Office Action of U.S. Appl. No. 09/783,931, filed Feb. 15, 2001, dated Feb. 5, 2003.
Office Action of U.S. Appl. No. 10/419,026, filed Apr. 18, 2003, dated Feb 10, 2005.
Office Action of U.S. Appl. No. 10/419,026, filed Apr. 18, 2003, dated Nov. 1, 2005.
Office Action of U.S. Appl. No. 10/746,237, filed Dec. 22, 2003, dated Dec. 28, 2006.
Office Action of U.S. Appl. No. 10/746,237, filed Dec. 22, 2003, dated Sep 19, 2007.
Office Action of U.S. Appl. No. 10/746,237, filed Dec. 22, 2003, dated Nov. 30, 2006.
Office Action of U.S. Appl. No. 10/746,237, filed Dec. 22, 2003, dated Mar. 30, 2006.
Office Action of U.S. Appl. No. 10/781,059, filed Feb. 17, 2004, dated Mar. 26, 2008.
Office Action of U.S. Appl. No. 10/781,059, filed Feb. 17, 2004, dated May 29, 2007.
Office Action of U.S. Appl. No. 10/781,060, filed Feb. 17, 2004, dated May 14, 2008.
Office Action of U.S. Appl. No. 10/781,060, filed Feb. 17, 2004, dated Aug. 9, 2007.
Office Action of U.S. Appl. No. 11/492,497, filed Jul. 24, 2006, dated Jul. 24, 2008.
Office Action of U.S. Appl. No. 07/695,189, filed May 3, 1991, dated Jun. 29, 1993.
Office Action of U.S. Appl. No. 07/791,923, filed Nov. 14, 1991, dated Feb. 16, 1993.
Office Action of U.S. Appl. No. 07/791,923, filed Nov. 14, 1991, dated Sep. 20, 1993.
Office Action of U.S. Appl. No. 07/791,923, filed Nov. 14, 1991, dated Jun. 3, 1994.
Office Action of U.S. Appl. No. 07/791,923, filed Nov. 14, 1991, dated Nov. 17, 1992.
Office Action of U.S. Appl. No. 07/879,038, filed Apr. 30, 1992, dated Jun. 3, 1994.
Office Action of U.S. Appl. No. 07/879,038, filed Apr. 30, 1992, dated Feb. 16, 1993.
Office Action of U.S. Appl. No. 07/879,038, filed Apr. 30, 1992, dated Nov. 17, 1992.
Office Action of U.S. Appl. No. 07/879,038, filed Apr. 30, 1992, dated Jun. 3, 1994.
Office Action of U.S. Appl. No. 07/879,038, filed Apr. 30, 1992 dated Sep. 20, 1993.
Office Action of U.S. Appl. No. 08/336,128, filed Apr. 30, 1992, dated Mar. 11, 1996.
Office Action of U.S. Appl. No. 08/346,126, filed Apr. 30, 1992, dated Mar. 12, 1996.
Office Action of U.S. Appl. No. 08/346,126 filed Apr. 30, 1992, dated May 30, 1995.
Office Action of U.S. Appl. No. 08/346,126 filed Apr. 30, 1992, dated Jun 1, 1995.
Office Action of U.S. Appl. No. 08/400,159, filed Mar. 7, 1995, dated Feb. 21, 1996.
Office Action of U.S. Appl. No. 08/400,159, filed Mar. 7, 1995, dated Oct. 3, 1996.
Office Action of U.S. Appl. No. 08/465,500, filed Jun. 5, 1995, dated Jul. 29, 1996.
Office Action of U.S. Appl. No. 08/465,500, filed Jun. 5, 1995, dated Apr. 18, 1997.
Office Action of U.S. Appl. No. 08/532,384, filed Sep. 22, 1995 dated Dec. 5, 1997.
Office Action of U.S. Appl. No. 08/532,384, filed Sep. 22, 1995 dated Jun. 29, 1998.
Office Action of U.S. Appl. No. 08/532,384, filed Sep. 22, 1995 dated Mar. 18, 1999.
Office Action of U.S. Appl. No. 08/532,384, filed Sep. 22, 1995 dated Mar. 31, 1997.
Office Action of U.S. Appl. No. 08/537,210, filed Sep. 29, 1995 dated Dec. 10, 1996.
Office Action of U.S. Appl. No. 08/537,210, filed Sep. 29, 1995 dated Dec. 12, 1996.
Office Action of U.S. Appl. No. 08/899,232, filed Jul. 23, 1997 dated Apr. 25, 2001.
Office Action of U.S. Appl. No. 08/899,232, filed Jul. 23, 1997 dated Jan. 16, 2001.
Office Action of U.S. Appl. No. 08/899,232, filed Jul. 23, 1997 dated Nov. 30, 1998.
Office Action of U.S. Appl. No. 08/899,232, filed Jul. 23, 1997 dated Oct. 14, 1999.
Office Action of U.S. Appl. No. 09/043,847, filed Jun. I, 1998, dated Apr. 9, 2002.

Office Action of U.S. Appl. No. 09/043,847, filed Jun. 1, 1998, dated Apr. 23, 2001.
Office Action of U.S. Appl. No. 09/043,847, filed Jun. 1, 1998, dated Feb. 16., 1999.
Office Action of U.S. Appl. No. 09/043,847, filed Jun. 1, 1998, dated Jul. 2, 2003.
Office Action of U.S. Appl. No. 09/043,847, filed Jun. 1, 1998, dated Oct. 14, 1999.
Office Action of U.S. Appl. No. 09/113,824, filed Jul. 10, 1998, dated Apr. 20, 2000.
Office Action of U.S. Appl. No. 09/113,824, filed Jul. 10, 1998, dated Aug. 9, 2001.
Office Action of U.S. Appl. No. 09/113,824, filed Jul. 10, 1998, dated Jan 26., 1999.
Office Action of U.S. Appl. No. 09/113,824, filed Jul. 10, 1998, dated Jan. 30, 2001.
Office Action of U.S. Appl. No. 09/113,824, filed Jul. 10, 1998, dated Jul. 2, 2003.
Office Action of U.S. Appl. No. 09/113,824, filed Jul. 10, 1998, dated Mar. 26, 2002.
Office Action of U.S. Appl. No. 09/113,824, filed Jul. 10, 1998, dated Sep. 27, 1999.
Office Action of U.S. Appl. No. 09/121,457, filed Jul. 23, 1998 dated Apr. 30, 2001.
Office Action of U.S. Appl. No. 09/121,457, filed Jul. 23, 1998 dated Feb. 14, 2000.
Office Action of U.S. Appl. No. 09/121,457, filed Jul. 23, 1998 dated Jun. 10, 1999.
Office Action of U.S. Appl. No. 09/121,457, filed Jul. 23, 1998 dated Oct. 17, 2002.
Office Action of U.S. Appl. No. 09/908,322, filed Jul. 17, 2001 dated Feb. 2, 2003.
Office Action of U.S. Appl. No. 09/908,322, filed Jul. 17, 2001 dated Nov. 5, 2003.
Office Action of U.S. Appl. No. 09/908,322, filed Jul. 17, 2001 dated Sep. 19, 2002.
Gray et al., 1999, "Human Ligands of the Notch Receptor," American Journal of Pathology, 154(3):785-794.
Park et al., 2006, "Notch3 gene amplification in ovarian cancer," Cancer Research, 66:6312-6318.
Purow et al., 2005, "Expression of Notch-1 and its ligands, Delta-like-1 and Jagged-1, is critical for glioma cell survival and proliferation," Cancer Res. 65:2353-2363.
Veeraraghavalu et al., 2004, "Papillomavirus-mediated neoplastic progression is associated with reciprocal changes in JAGGED1 and manic fringe expression linked to notch activation," J. Virology 78:8687-8700.
Li et al. 2008, "Modulation of Notch signaling by antibodies specific for the extracellular negative regulatory region of NOTCH3," J. Biol. Chem. 283:8046-8054.
Hukriede et al., "A dominant-negative form of Serrate acts as a general antagonist of Notch activation," 1997, Development 124:3427-3437.
Chitnis et al., "Primary neurogenesis in Xenopus embryos regulated by a homologue of the Drosophila neurogenic gene Delta," 1995, Nature 29:761-766.
Office Action of U.S. Appl. No. 10/781,060, filed Feb. 17, 2004, dated Jun. 19, 2009.
Office Action of U.S. Appl. No. 11/492,497, filed Jul. 24, 2006, dated May 7, 2009.
Malicki et al., "Mouse hex-2.2 Specifics Thoracic Segmental Identity in Drosophila Embryos and Larvae." 1990, Cell 63:951-967.

* cited by examiner

FIG.1A   FIG.1B
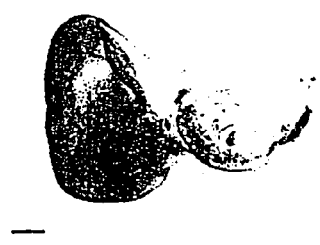
FIG.1C   FIG.1D
FIG.1E   FIG.1F

FIG.3A
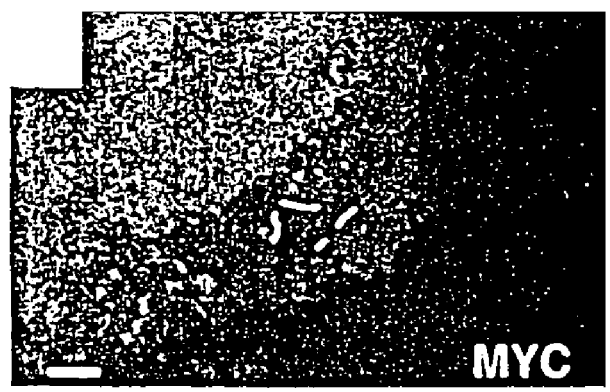
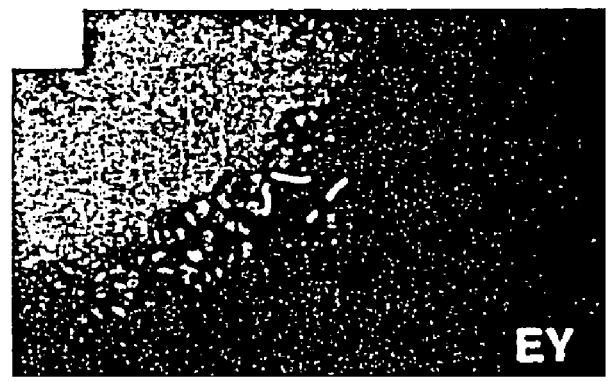
FIG.3B

FIG.4A
FIG.4B

FIG.5A
FIG.5B

MANIPULATION OF TISSUE OF ORGAN TYPE USING THE NOTCH PATHWAY

This application is a continuation of U.S. application Ser. No. 09/614,003, filed Jul. 11, 2000 now abandoned, which claims the benefit of U.S. Provisional Application No. 60/143,484, filed Jul. 12, 1999, each of which is incorporated herein by reference in its entirety.

1. FIELD OF THE INVENTION

The present invention is directed to methods for altering the fate of a cell, tissue or organ type by altering Notch pathway function in the cell. The invention is further directed to methods for altering the fate of a cell, tissue or organ type by simultaneously changing the activation state of the Notch pathway and one or more cell fate control gene pathways. The invention can be utilized for cells of any differentiation state. The resulting cells may be expanded and used in cell replacement therapy to repopulate lost cell populations and help in the regeneration of diseased and/or injured tissues. The resulting cell populations can also be made recombinant and used for gene therapy or as tissue/organ models for research. The invention is directed to methods for of treating macular degeneration comprising altering Notch pathway function in cells of the retinal pigment epithelium and/or the neuroepithelium. The present invention is also directed to kits utilizing the methods of the invention to generate cells, tissues or organs of altered fates. The invention also provides methods for screening for agonists or antagonists of Notch or cell fate control gene pathway functions.

2. BACKGROUND OF THE INVENTION

2.1. Developmental Processes

The developmental processes that govern the ontogeny of multicellular organisms, including humans, depends on the interplay between signaling pathways, which gradually narrow the developmental potential of cells from the original totipotent stem cell to the terminally differentiated mature cell, which performs a specialized function, such as a heart cell or a nerve cell.

The fertilized egg is the cell from which all other cell lineages derive, i.e., the ultimate stem cell. As development proceeds, early embryonic cells respond to growth and differentiation signals which gradually narrow the cells' developmental potential, until the cells reach developmental maturity, i.e., are terminally differentiated. These terminally differentiated cells have specialized functions and characteristics, and represent the last step in a multi-step process of precursor cell differentiation into a particular cell.

The transition from one step to the next in cell differentiation is governed by specific biochemical mechanisms which gradually control the progression until maturity is reached. It is clear that the differentiation of tissues and cells is a gradual process which follows specific steps until a terminally differentiated state is reached.

Gastrulation, the morphogenic movement of the early embryonic cell mass, results in the formation of three distinct germ cell layers, the ectoderm, the mesoderm, and the endoderm. As cells in each germ cell layer respond to various developmental signals, specific organs are generated which are composed of specific differentiated cells. For example, the epidermis and the nervous system develop from ectoderm-derived cells, the respiratory system and the digestive tract are developed from endoderm-derived cells, and mesoderm-derived cells develop into the connective tissues, the hematopoietic system, the urogenital system, muscle, and parts of most internal organs.

The following is a brief outline of how ectoderm, endoderm and mesoderm are developed and further, how these three dermal layers give rise to the different tissues of the body. For a general review of development see Scott F. Gilbert, 1991, Developmental Biology, 3rd Edition, Sinauer Associates, Inc., Sunderland Mass.

The interaction between the dorsal mesoderm and the overlaying ectoderm initiates organogenesis. In this interaction the chordamesoderm directs the ectoderm above it to form the neural tube which will eventually give rise to the brain and the spinal cord. The differentiation of the neural tube into the various regions of the central nervous system is clear at the gross anatomical level where morphogenetic changes shape specific constrictions and bulges to form the chambers of the brain and the spinal cord. At the cellular level, cell migratory events rearrange various groups of cells. The neuroepithelial cells respond to growth and differentiation signals and eventually differentiate into the numerous types of neurons and supportive (glial) cells. Both neural tube and brain are highly regionalized with each specific region serving distinct functional purposes (see FIG. 1). Each cell in this tissue has specific morphological and biochemical characteristics. Differentiated cells are the last step in a lineage where precursor cells responding to developmental cues progress to a more differentiated state until they reach their terminal differentiation state. For example, ependymal cells which are the integral components of the neural tube lining can give rise to precursors which may differentiate into neurons or glia depending on the developmental cues they will receive (Rakic et al., 1982, Neurosci. Rev. 20:429-611).

The neural crest derives from the ectoderm and is the cell mass from which an extraordinary large and complex number of differentiated cell types are produced, including the peripheral nervous system, pigment cells, adrenal medulla and certain areas of the head cartilage.

The fate of neural crest cells will depend on where they migrate and settle during development since the cells will encounter different differentiation and growth signals that govern their ultimate differentiation. The pluripotentiality of neural crest cells is well established (LeDouarin et al., 1975, Proc. Natl. Acad. Sci USA 72:728-732). A single neural crest cell can differentiate into several different cell types. Transplantation experiments of cell populations or single neural crest cells point to the remarkably plastic differentiation potential of these cells. Even though the cell lineages of the various differentiation pathways have not been established to the degree they have in hematopoietic development, the existence of multi-potential cell precursors, reminiscent to those seen in the hematopoietic system, is well founded.

The cells covering the embryo after neurulation form the presumptive epidermis. The epidermis consists of several cellular layers which define a differentiation lineage starting from the undifferentiated, mitotically active basal cells to the terminally differentiated non-dividing keratinocytes. The latter cells are eventually shed and constantly replenished by the underlying less differentiated precursors. Psoriasis, a pathogenic condition of the skin, results from the exfoliation of abnormally high levels of epidermal cells.

Skin is not only the derivative of epidermis. Interactions between mesenchymal dermis, a tissue of mesodermal origin and the epidermis at specific sites, result in the formation of cutaneous appendages, hair follicles, sweat glands and apocrine glands. The cell ensemble that produces hairs is rather dynamic in that the first embryonic hairs are shed before birth and replaced by new follicles (vellus). Vellus, a short and silky hair, remains on many parts of the body which are considered hairless, e.g., forehead and eye lids. In other areas vellus can give way to "terminal" hair. Terminal hair can revert into the production of unpigmented vellus, a situation found normally in male baldness.

The endoderm is the source of the tissues that line two tubes within the adult body. The digestive tube extends throughout the length of the body. The digestive tube gives rise not only to the digestive tract but also to, for example, the liver, the gallbladder and the pancreas. The second tube, the respiratory tube, forms the lungs and part of the pharynx. The pharynx gives rise to the tonsils, thyroid, thymus, and parathyroid glands.

The genesis of the mesoderm which has also been referred to as the mesengenic process gives rise to a very large number of internal tissues which cover all the organs between the ectodermal wall and the digestive and respiratory tubes. As is the case with all other organs it is the intricate interplay between various intercellular signaling events and the response of non-terminally differentiated precursor cells that will eventually dictate specific cellular identities. To a large degree organ formation depends on the interactions between mesenchymal cells with the adjacent epithelium. The interaction between dermis and epidermis to form, e.g., hairs, has been described above. The formation of the limbs, the gut organs, liver or pancreas, kidney, teeth, etc., all depend on interactions between specific mesenchymal and epithelial components. In fact, the differentiation of a given epithelium depends on the nature of the adjacent mesenchyme. For example, when lung bud epithelium is cultured alone, no differentiation occurs. However, when lung bud epithelium is cultured with stomach mesenchyme or intestinal mesenchyme, the lung bud epithelium differentiates into gastric glands or villi, respectively. Further, if lung bud epithelium is cultured with liver mesenchyme or bronchial mesenchyme, the epithelium differentiates into hepatic cords or branching bronchial buds, respectively. Examples of factors that mediate these inductive processes are described in Section 2.3, infra.

Embryonic development produces the fully formed organism. The morphologic processes that define the cellular boundaries of each organ include not only proliferation and differentiation, but also apoptosis (programmed cell death). For example, in the nervous system, approximately 50% of neurons undergo programmed cell death during embryogenesis.

In the juvenile or adult individual, the maintenance of tissues, whether during normal life or in response to injury and disease, depends on the replenishing of the organs from precursor cells that are capable of responding to specific developmental signals.

The best known example of adult cell renewal via the differentiation of immature cells is the hematopoietic system. Here, developmentally immature precursors (hematopoietic stem and progenitor cells) respond to molecular signals to gradually form the varied blood and lymphoid cell types.

While the hematopoietic system is the best understood self renewing adult cellular system it is believed that most, perhaps all, adult organs harbor precursor cells that under the right circumstances, can be triggered to replenish the adult tissue. For example, the pluripotentiality of neural crest cells has been described above. The adult gut contains immature precursors which replenish the differentiated tissue. Liver has the capacity to regenerate because it contains hepatic immature precursors; skin renews itself, etc. Through the mesengenic process, most mesodermal derivatives are continuously replenished by the differentiation of precursors. Such repair recapitulates the embryonic lineages and entails differentiation paths which involve pluripotent progenitor cells.

Mesenchymal progenitor cells are pluripotent cells that respond to specific signals and adopt specific lineages. For example, in response to bone morphogenic factors, mesenchymal progenitor cells adopt a bone forming lineage. For example, in response to injury, mesodermal progenitor cells can migrate to the appropriate site, multiply and react to local differentiation factors, consequently adopting a distinct differentiation path. It has been suggested that the reason that only a limited tissue repair is observed in adults is because there are too few progenitor cells which can adopt specific differentiation lineages. It is clear that if tissues can be changed so that they take on another fate, then tissue repair could be much more efficient, utilizing cells or tissues that are more readily available. Further, the process of growing cells of a desired tissue or organ type ex vivo would give rise to more rapid proliferation of the desired tissue and allow for more rapid treatment injuries or traumas, and would also provide a source of cells for organ and tissue transplants. A pool of cells, and more so a pool of expanded cells of a particular cell fate, would be of great value in gene therapy and a myriad of therapeutic regimens.

Additionally, the ability to alter cell fates such that apoptosis is induced in certain cells and circumvented in others would give rise to the potential for treating many human diseases, such as cancer, which results from uncontrolled proliferation and lack of appropriate response to cell fate cues, and degenerative diseases, which result from inappropriate cell death, respectively.

2.2. Genes that Participate in Cell Fate Decisions 2.2.1. The Notch Pathway

Genetic and molecular studies have led to the identification of a group of genes which define distinct elements of the Notch signaling pathway. While the identification of these various elements has come exclusively from *Drosophila* using genetic tools as the initial guide, subsequent analyses have lead to the identification of homologous proteins in vertebrate species including humans. The molecular relationships between the known Notch pathway elements as well as their subcellular localization are depicted in Artavanis-Tsakonas et al., 1995 (Science 268:225-232).

Several members of the Notch signaling pathway have been cloned and sequenced, for example, Notch (Wharton et al., 1985, Cell 43:567-581; Int'l Publn. No. WO92/19734 dated Nov. 12, 1992; Ellison et al., 1991, Cell 66:523-534; Weinmaster et al., Development 116:931-941; Coffman et al., 1990, Science 249:1438-1441; Stifani et al., 1992, Nature Genet. 2:119-127; Lardelli and Lendahl, 1993, Exp. Cell. Res. 204:364-372; Lardelli et al., 1994, Mech. Dev. 96:123-136; Bierkamp et al., 1993, Mech. Dev. 43:87-100); Delta (Kopczynski et al., 1988, Genes Dev. 2:1723-1735; Henrique et al., 1995, Nature 375:787-790; Chitnis et al., 1995, Nature 375:761-766); Serrate (Fleming et al., 1990, Genes Dev. 1:2188-2201; Lindsell et al., 1995, Cell 80:909-917; Thomas et al., 1991, Development 111:749-761); the cytoplasmic protein Deltex (Busseau et al., 1994, Genetics 136:585-596); and the nuclear proteins encoded by Mastermind, Hairless, the Enhancer of Split Complex and Suppressor of Hairless (Smoller et al., 1990, Genes Dev. 4:1688-1700; Bang and Posakony, 1992, Genes Dev. 6:1752-1769; Maier et al., 1992, Mech. Dev. 38:143-156; Delidakis et al., 1991, Genetics 129: 803-823; Schrons et al., 1992, Genetics 132:481-503;

Furukawa et al., 1991, J. Biol. Chem. 266:23334-23340; Furukawa et al., 1992, Cell 69:1191-1197; Schweisguth and Posakony, 1992, Cell 69:1199-1212; Fortini and Artavanis-Tsakonas, 1994, Cell 79:273-282.

The extracellular domain of Notch carries 36 EGF-like repeats, two of which have been implicated in interactions with the Notch ligands Serrate and Delta. Delta and Serrate are membrane bound ligands with EGF homologous extracellular domains, which interact physically with Notch on adjacent cells to trigger signaling.

Functional analyses involving the expression of truncated forms of the Notch receptor have indicated that receptor activation depends on the six cdc10/ankyrin repeats in the intracellular domain. Further, Notch activation requires that the cdc10/ankyrin repeats reach the nucleus—possibly after proteolytic cleavage from the remainder of the protein—and participate in transcriptional activation (Struhl and Adachi, 1998, Cell 93:649-660). Deltex and Suppressor of Hairless, whose over-expression results in an apparent activation of the pathway, associate with those repeats. Recent evidence suggests that the proteolytic cleavage step that releases the cdc10/ankyrin repeats for nuclear entry is dependent on Presenilin activity (De Strooper et al., 1999, Nature 398:518-522; Struhl and Greenwald, ibid.:522-525; Ye et al., ibid.:525-529).

The Notch pathway is dependent on protein processing events additional to the step that releases the ankyrin repeats of Notch to the nucleus. The Notch receptor present in the plasma membrane comprises a heterodimer of two Notch proteolytic cleavage products, one comprising an N-terminal fragment consisting a portion of the extracellular domain, the transmembrane domain and the intracellular domain, and the other comprising the majority of the extracellular domain (Blaumueller et al., 1997, Cell 90:281-291). The proteolytic cleavage step of Notch to activate the receptor occurs in the Golgi apparatus and is mediated by a furin-like convertase (Logeat et al., 1998, Proc. Natl. Acad. Sci. USA 95:8108-8112). The Notch ligand, Delta, additionally requires cleavage for activation. Delta is cleaved by a the ADAM disintegrin metalloprotease Kuzbanian at the cell surface, the cleavage event releasing a soluble and active form of Delta (Qi et al., 1999, Science 283:91-94).

Suppressor of Hairless is the *Drosophila* homolog of CBF1, a mammalian DNA binding protein involved in the Epstein-Barr virus-induced immortalization of B cells. It has been demonstrated that, at least in cultured cells, Suppressor of Hairless associates with the cdc10/ankyrin repeats in the cytoplasm and translocates into the nucleus upon the interaction of the Notch receptor with its ligand Delta on adjacent cells (Fortini and Artavanis, 1994, Cell 79:273-282). The association of Hairless, a novel nuclear protein, with Suppressor of Hairless has been documented using the yeast two hybrid system therefore, it is believed that the involvement of Suppressor of Hairless in transcription is modulated by Hairless (Brou et al., 1994, Genes Dev. 8:2491; Knust et al. 1992, Genetics 129:803).

Deltex is a cytoplasmic protein which contains a ring zinc finger. Deltex interacts with the ankyrin repeats of Notch (Matsuno et al., 1995, Development 121:2633-2644) and is postulated to promote Notch pathway activation by preventing membrane-localized Notch from binding to the Suppressor of Hairless, thereby releasing the Suppressor of Hairless into the nucleus where it can act as a transcriptional modulator. However, in a vertebrate B-cell system, it has also been shown that Deltex and not the Suppressor of Hairless homolog, CBF1, is responsible for inhibiting E47 function (Ordentlich et al., 1998, Mol. Cell. Biol. 18:2230-2239).

Finally, it is known that Notch signaling results in the activation of at least certain bHLH genes within the Enhancer of split complex (Delidakis et al., 1991, Genetics 129:803). Mastermind encodes a novel ubiquitous nuclear protein whose relationship to Notch signaling remains unclear but is involved in the Notch pathway as shown by genetic analysis (Smoller et al., 1990, Genes Dev. 4:1688).

The generality of the Notch pathway manifests itself at different levels. At the genetic level, many mutations exist which affect the development of a very broad spectrum of cell types in *Drosophila*. Knockout mutations in mice are embryonic lethals consistent with a fundamental role for Notch function (Swiatek et al., 1994, Genes Dev. 8:707). Mutations in the Notch pathway in the hematopoietic system in humans are associated with lymphoblastic leukemia (Ellison et al., 1991, Cell 66:649-661). Finally the expression of mutant forms of Notch in developing *Xenopus* embryos interferes profoundly with normal development (Coffman et al., 1993, Cell 73:659).

The expression patterns of Notch in the *Drosophila* embryo are complex and dynamic. The Notch protein is broadly expressed in the early embryo, and subsequently becomes restricted to uncommitted or proliferative groups of cells as development proceeds. In the adult, expression persists in the regenerating tissues of the ovaries and testes (reviewed in Fortini et al., 1993, Cell 75:1245-1247; Jan et al., 1993, Proc. Natl. Acad. Sci. USA 90:8305-8307; Sternberg, 1993, Curr. Biol. 3:763-765; Greenwald, 1994, Curr. Opin. Genet. Dev. 4:556-562; Artavanis-Tsakonas et al., 1995, Science 268:225-232). Studies of the expression of Notch1, one of three known vertebrate homologs of Notch, in zebrafish and *Xenopus*, have shown that the general patterns are similar; with Notch expression associated in general with non-terminally differentiated, proliferative cell populations. Tissues with high expression levels include the developing brain, eye and neural tube (Coffman et al., 1990, Science 249:1438-1441; Bierkamp et al., 1993, Mech. Dev. 43:87-100). While studies in mammals have shown the expression of the corresponding Notch homologs to begin later in development, the proteins are expressed in dynamic patterns in tissues undergoing cell fate determination or rapid proliferation (Weinmaster et al., 1991, Development 113:199-205; Reaume et al., 1992, Dev. Biol. 154:377-387; Stifani et al., 1992, Nature Genet. 2:119-127; Weinmaster et al., 1992, Development 116:931-941; Kopan et al., 1993, J. Cell Biol. 121:631-641; Lardelli et al., 1993, Exp. Cell Res. 204:364-372; Lardelli et al., 1994, Mech. Dev. 46:123-136; Henrique et al., 1995, Nature 375:787-790; Horvitz et al., 1991, Nature 351:535-541; Franco del Amo et al., 1992, Development 115:737-744). Among the tissues in which mammalian Notch homologs are first expressed are the pre-somitic mesoderm and the developing neuroepithelium of the embryo. In the pre-somitic mesoderm, expression of Notch1 is seen in all of the migrated mesoderm, and a particularly dense band is seen at the anterior edge of pre-somitic mesoderm. This expression has been shown to decrease once the somites have formed, indicating a role for Notch in the differentiation of somatic precursor cells (Reaume et al., 1992, Dev. Biol. 154:377-387; Horvitz et al., 1991, Nature 351:535-541). Similar expression patterns are seen for mouse Delta (Simske et al., 1995, Nature 375:142-145).

Within the developing mammalian nervous system, expression patterns of Notch homolog have been shown to be prominent in particular regions of the ventricular zone of the spinal cord, as well as in components of the peripheral nervous system, in an overlapping but non-identical pattern. Notch expression in the nervous system appears to be limited to regions of cellular proliferation, and is absent from nearby populations of recently differentiated cells (Weinmster et al., 1991, Development 113:199-205; Reaume et al., 1992, Dev. Biol. 154:377-387; Weinmaster et al., 1992, Development 116:931-941; Kopan et al., 1993, J. Cell Biol. 121:631-641; Lardelli et al., 1993, Exp. Cell Res. 204:364-372; Lardelli et al., 1994, Mech. Dev. 46:123-136; Henrique et al., 1995, Nature 375:787-790; Horvitz et al., 1991, Nature 351:535-541). A rat Notch ligand is also expressed within the developing spinal cord, in distinct bands of the ventricular zone that overlap with the expression domains of the Notch genes. The spatio-temporal expression pattern of this ligand correlates well with the patterns of cells committing to spinal cord neuronal fates, which demonstrates the usefulness of Notch as a marker of populations of cells for neuronal fates (Henrique et al., 1995, Nature 375:787-790). This has also been suggested for vertebrate Delta homologs, whose expression domains also overlap with those of Notch1 (Larsson et al., 1994, Genomics 24:253-258; Fortini et al., 1993, Nature 365:555-557; Simske et al., 1995, Nature 375:142-145). In the cases of the *Xenopus* and chicken homologs, Delta is actually expressed only in scattered cells within the Notch1 expression domain, as would be expected from the lateral specification model, and these patterns "foreshadow" future patterns of neuronal differentiation (Larsson et al., 1994, Genomics 24:253-258; Fortini et al., 1993, Nature 365:555-557).

Other vertebrate studies of particular interest have focused on the expression of Notch homologs in developing sensory structures, including the retina, hair follicles and tooth buds. In the case of the *Xenopus* retina, Notch1 is expressed in the undifferentiated cells of the central marginal zone and central retina (Coffman et al., 1990, Science 249:1439-1441; Mango et al., 1991, Nature 352:811-815). Studies in the rat have also demonstrated an association of Notch1 with differentiating cells in the developing retina have been interpreted to suggest that Notch1 plays a role in successive cell fate choices in this tissue (Lyman et al., 1993, Proc. Natl. Acad. Sci. USA 90:10395-10399).

A detailed analysis of mouse Notch1 expression in the regenerating matrix cells of hair follicles was undertaken to examine the potential participation of Notch proteins in epithelial/mesenchymal inductive interactions (Franco del Amo et al., 1992, Development 115:737-744). Such a role had originally been suggested for Notch1 based on the its expression in rat whiskers and tooth buds (Weinmaster et al., 1991, Development 113:199-205). Notch1 expression was instead found to be limited to subsets of non-mitotic, differentiating cells that are not subject to epithelial/mesenchymal interactions, a finding that is consistent with Notch expression elsewhere.

Expression studies of Notch proteins in human tissue and cell lines have also been reported. The aberrant expression of a truncated Notch1 RNA in human T-cell leukemia results from a translocation with a breakpoint in Notch1 (Ellisen et al., 1991, Cell 66:649-661). A study of human Notch1 expression during hematopoiesis has suggested a role for Notch1 in the early differentiation of T-cell precursors (Mango et al., 1994, Development 120:2305-2315). Additional studies of human Notch1 and Notch2 expression have been performed on adult tissue sections including both normal and neoplastic cervical and colon tissue. Notch1 and Notch2 appear to be expressed in overlapping patterns in differentiating populations of cells within squamous epithelia of normal tissues that have been examined and are clearly not expressed in normal columnar epithelia, except in some of the precursor cells. Both proteins are expressed in neoplasias, in cases ranging from relatively benign squamous metaplasias to cancerous invasive adenocarcinomas in which columnar epithelia are replaced by these tumors (Gray et al., 1999, Am. J. Pathol. 154:785-794; Zagouras et al., 1995, Proc. Natl. Acad. Sci. USA 92:6414-6418).

Insight into the developmental role and the general nature of Notch signaling has emerged from studies with truncated, constitutively activated forms of Notch in several species. These recombinantly engineered Notch forms, which lack extracellular ligand-binding domains, resemble the naturally occurring oncogenic variants of mammalian Notch proteins and are constitutively activated using phenotypic criteria (Greenwald, 1994, Curr. Opin. Genet. Dev. 4:556; Fortini et al., 1993, Nature 365:555-557; Coffman et al., 1993, Cell 73:659-671; Struhl et al., 1993, Cell 69:1073; Rebay et al., 1993, Genes Dev. 7:1949; Kopan et al., 1994, Development 120:2385; Roehl et al., 1993, Nature 364:632).

Ubiquitous expression of activated Notch in the *Drosophila* embryo suppresses neuroblast segregation without impairing epidermal differentiation (Struhl et al., 1993, Cell 69:331; Rebay et al., 1993, Genes Dev. 7:1949).

Persistent expression of activated Notch in developing imaginal epithelia likewise results in an overproduction of epidermis at the expense of neural structures (Struhl et al., 1993, Cell 69:331).

Neuroblast segregation occurs in temporal waves that are delayed but not prevented by transient expression of activated Notch in the embryo (Struhl et al., 1993, Cell 69:331).

Transient expression in well-defined cells of the *Drosophila* eye imaginal disc causes the cells to ignore their normal inductive cues and to adopt alternative cell fates (Fortini et al., 1993, Nature 365:555-557).

Studies utilizing transient expression of activated Notch in either the *Drosophila* embryo or the eye disc indicate that once Notch signaling activity has subsided, cells may recover and differentiate properly or respond to later developmental cues (Fortini et al., 1993, Nature 365:555-557; Struhl et al., 1993, Cell 69:331).

For a general review on the Notch pathway and Notch signaling, see Artavanis-Tsakonas et al., 1995, Science 268: 225-232 and Artavanis-Tsakonas et al., 1999, Science 284: 770-776.

2.2.2. Pax Genes and Proteins

Pax genes (reviewed by Dahl et al., 1997, Bioessays 19:755-766; Noll, 1993, Curr. Opin. Gen. Dev. 4:427-438) encode transcription factors characterized as having a domain called the paired domain, named after *Drosophila* paired, the first gene of the Pax family to be identified. The paired box has been functionally divided into two subdomains, the PAI and RED domains (Czerny et al., 1993, Genes Dev. 7:2048-2061). In addition to the paired domain, PAX proteins contain a homeodomain and/or an octapeptide motif. According to the structural motifs they encode, Pax genes have been classified into four different groups (Walther et al., 1991, Genomics 11:424-434; Dahl et al., 1997, Bioessays 19:755-766). Group I proteins such as Pax1 possess a paired domain and an octapeptide motif; Group II proteins (e.g. Pax2) possess a paired domain, an octapeptide and a partial homeodomain consisting of only one helix; Group III proteins (e.g. Pax3) possess a paired domain, an octapeptide and a homeodomain; and Group IV proteins (e.g. Pax4) possess a paired domain and a homeodomain. Both the paired domain and the homeodomain, contribute to the DNA binding activity of the PAX proteins (see for example Treisman et al., 1991, Genes Dev. 5:594-604). In some instances there exist cooperative interactions in DNA binding, either intramolecularly between the two paired subdomains (PAI and RED) (Pellizzari et al., 1999, Biochem J. 337:253-262) or between the paired domain and the homeodomain (Jun et al., 1996, Development 122:2639-2650), or intermolecularly between the homeodomains of different Pax proteins (Wilson et al., 1993, Genes Dev. 7:2120-2134). In addition to their DNA binding functions, the paired domain and the homeodomain contribute to the interactions of Pax proteins with other transcription factors (see, e.g., Eberhard et al., 1999, Cancer Res. 59 (7 Suppl.):1716s-1725s; Wheat et al., 1999, Mol. Cell Biol. 19:2231-2241).

Outside *Drosophila*, mice and humans, Pax genes have been cloned from a large variety of organisms, including rat (Otsen et al., 1995, Mamm. Genome 6:666-667), chicken (Nohno et al., 1993, Dev. Biol. 158:254-264), quail (Carriere et al., 1993, Mol. Cell Biol. 13:7257-7266), zebrafish (Kelly et al., 1995, Dev. Genet. 17:129-140), urodele (Del Rio-Tsonis et al., 1995, Proc. Natl. Acad. Sci. USA 92:5092-5096), squid (Tomarev et al., 1997, Proc. Natl. Acad. Sci. USA 94:2421-2426), jellyfish (Sun et al., 1996, Proc. Natl. Acad. Sci. USA 94:5156-5161), hydra (Sun et al., 1996, Proc. Natl. Acad. Sci. USA 94:5156-5161), the nematode *Caenorhabditis elegans* (Zhang et al., 1995, Nature 377:55-59), the ribbonworm *Lineus sanguineus* (Loosli et al., 1996, Proc. Natl. Acad. Sci. USA 93:2658-2663), the ascidian *Phallusia mammillata* (Glardon et al., 1997, Development 124:817-825) and amphioxus (Holland et al., 1995, Mol. Mar. Biol. Biotechnol. 4:206-214).

The roles of Pax genes in development have been elucidated by means of classical and molecular genetics. In humans, mutations in Pax genes result in spina bifida (Pax 1; Hol et al., 1996, J. Med. Genet. 33:655-660), renal coloboma syndrome (Pax2; Sanyanusin et al., 1995, Nat. Genet. 9:358-363), Waardenburg Syndrome (Pax 3; Tassabehji et al., 1992, Nature 355:635-636; Baldwin et al., ibid. 637-638) and aniridia/Peter's anomaly (Pax6; Macdonald and Wilson, 1996, Curr. Opin. Neurobiol. 6:49-56). Similar phenotypes have been detected in mouse Pax mutants, e.g. spina bifida (Pax1 (or undulated)); Dietrich and Gruss, 1995, Dev. Biol. 167: 529-548; Helwig et al., 1995, Nat. Genet. 11:60-63) and Small eye (Pax6; Macdonald and Wilson, 1996, Curr. Opin. Neurobiol. 6:49-56). Strikingly, the conservation of Pax gene function extends to invertebrates such as *Drosophila*, wherein a loss of function mutation of the Pax6 homolog, eyeless (ey) gives rise to flies lacking ommatidia, hence the name of the gene (Hunt et al., 1969, Genet Res. 13:251-65; Quiring et al., 1994, Science 265:785-9). Another *Drosophila* Pax6 gene is twin of eyeless (toy, Czerny et al., 1999, Mol. Cell 3:297-307.), an upstream regulator of ey and whose ectopic expression leads to ectopic eye formation mediated by the induction of ey expression.

The phenotypes of loss of function Pax mutants reveals the important roles that these genes play in tissue differentiation and organogenesis. Most mammalian organs that express Pax genes e.g. thymus, kidney, thyroid, tooth, lung and hair (see e.g. Thesleff et al., 1995, Dev. Biol. 39:35-50) develop after an inductive event has taken place between mesenchymal and epithelial cells. During this process, the Pax gene(s) can be expressed in one or both of the interacting tissues; however, each tissue studied to date expresses a unique combination of Pax genes. In the absence of Pax gene function during organogenesis, the inductive interaction between the mesenchyme and epithelium fails. An illustrative example of this failure is in kidney development, which is induced upon the interaction between the ureteric bud epithelium and the metanephric mesenchyme (Saxen and Lehtonen, 1978, J. Embryol. Exp. Morph. 47:97-109). During the terminal stages of kidney differentiation, part of the mesenchyme is changed into kidney tubule epithelium, whereas the ureteric bud is induced to branch, forming the mature duct system. Pax2 is expressed transiently in the metanephric mesenchyme (Torres et al., 1995, Development 121:4057-4065; Dressler et al., 1990, Development 109:787-795), and elimination of Pax2 expression from the tissue by means of antisense oligonucleotides prevents the mesenchyme-to-epithelium change, leading to apoptosis of the mesenchymal cells (Rothenpleler and Dressler, 1993, Development 119:711-720). Pax2 is also involved in other inductive events during renal development (Torres et al., 1995, Development 121:4057-4065), as are other Pax genes in other organs during analogous inductive processes (see e.g. Wallin et al., 1996, Development 122:23-30 for thymus differentiation; Macchia et al., 1998, Nature Genet. 19:83-86 for thyroid development; Wilm et al., 1998, Proc. Natl. Acad. Sci. USA 95:8692-7 for skeletal development; Peters et al., 1998, Genes Dev. 12:2735-47 for tooth differentiation). It has become increasingly apparent that the roles of Pax proteins are at the interfaces between cellular cues, e.g. differentiation or proliferation signals, and the cellular responses to the cues, e.g. differentiation or proliferation (a few such examples are presented by Dahl et al., 1997, Bioessays 19:755-763).

2.2.3. Homeotic/HOX/HOM-C Genes and Proteins

Homeotic genes were initially identified in *Drosophila melanogaster* by virtue of their mutant phenotypes, which cause the cells of one compartment to be transformed into the equivalent cells of another compartment. One classical homeotic mutation is Antennapedia$^{NS}$ (Antp$^{NS}$), which transforms the fly antennae into legs (Gehring, 1967, Arch Julius Klaus Stift Vererbungsforsch Sozialanthropol Rassenhyg. 41:44-54). The cause of this transformation is a gain of function mutation in the Antennapedia gene which results in the ectopic expression of Antennapedia protein in the antennal primordia (Frischer et al., 1986, Cell 47:1017-23). Loss of function mutations of Antennapedia result in the converse phenotype, or the transformation of leg tissue into antennal tissue (Struhl, 1982, Proc. Natl. Acad. Sci. USA 79:7380-7384). Another example of tissue transformation as a result of a homeotic gene mutation is the transformation of the fly's balance organs, the halteres, into wings, giving rise to a four winged fly, in the absence of Ultrabithorax function during the larval stages of *Drosophila* development (reviewed by Lewis, 1998, Int. J. Dev. Biol. 42:403-415).

The homeotic genes of the fly were cloned and found to code for transcription factors with a highly conserved DNA binding sequence called the homeodomain (McGinnis et al., 1984, Nature 308:428-433; Scott and Weiner, 1984, Proc. Natl. Acad. Sci. USA 81:4115-4119). Homeotic genes are found clustered in the genome and their expression patterns in overlapping domains along the body axis mirrors the order they are found in the genome (Gaunt et al., 1986, Nature 324:662-4; Gaunt et al., 1989, Development 107:131-141; Ponchinelli et al., 1988, Human Rep. 3:880-886; Bachiller et al., 1994, EMBO J. 13:1930-1941). Subsequent to the characterization of *Drosophila* homeotic genes, homeotic genes—by virtue of their homology—were found to exist throughout the animal kingdom. Mammalian and fly homeotic genes are very highly conserved, from the level of their sequences to their organization in their genome (Graham et al., 1989, Cell 57:367-378) to their function (see below). In mammals, there are four homeotic gene clusters named A-D. Individual homeotic genes are named according to the cluster they belong to and their position in the series, for example HOX A5 or HOX D9, although none of the clusters contain the full complement of 13 homeotic genes (see Table I below; also reviewed by Krumlauf, 1992, Bioessays 14:245-252; Scott, 1992, Cell 71:551-553).

The next two protein families described, the MEINOX and PBC families, belong to a yet larger family of homeodomain proteins called TALE proteins (Burglin, 1997, Nucleic Acids Res. 25:4173-4180), named for the three amino acid loop extension between the first and second helices of the home-

TABLE I

Genomic configuration of *Drosophila* and mammalian HOX genes

| 5' | | | | | | | | | | | | | | 3' | |
|---|---|---|---|---|---|---|---|---|---|---|---|---|---|---|---|
| | | | | ABD-B | ABD-A | UBX | \\* | ANTP | SCR | DFD | | PB | LAB | *Drosophila* HOM-C |
| A13 | | A11 | A10 | A9 | | A7 | | A6 | A5 | A4 | A3 | A2 | A1 | Mammalian HoxA |
| B13 | | | | B9 | B8 | B7 | | B6 | B5 | B4 | B3 | B2 | B1 | Mammalian HoxB |
| C13 | C12 | C11 | C10 | C9 | C8 | | | C6 | C5 | C4 | | | | Mammalian HoxC |
| D13 | D12 | D11 | D10 | D9 | D8 | | | | | D4 | D3 | | D1 | Mammalian HoxD |

*\\ indicates that the *Drosophila* HOM-C is broken up into two regions in the genome: the Antennapedia complex (Antp-C) and the Bithorax complex (BX-C). Antp-C comprises the HOX genes labial (lab), proboscipedia (pb), Deformed (Dfd), Sex combs reduced (Scr), and Antennapedia (Antp); BX-C comprises Ultrabithorax (Ubx), abdominal-A (abd-A) and Abdominal-B (Abd-B).

While the roles of homeotic genes in mammalian development have not been defined as clearly as have their roles in *Drosophila*, the limited studies of mouse HOX knockout mutants suggest similar roles in determining tissue or organ identity. These phenotypes are clearest in segmented tissues, for example skeletal tissues, where transformations of vertebrae occur when HOX function is altered. For example, HOX A11 mutant mice exhibit transformation of thoracic or sacral vertebrae to lumbar vertebrae (Small and Potter, 1993, Genes Dev. 7:2318-38). The high level of conservation of homeotic gene function has also been demonstrated by genetic rescue or gain of function experiments in which an avian or mammalian homolog of a particular homeotic gene can function almost identically to the corresponding *Drosophila* gene when expressed in the fly (e.g. Lutz et al., 1996, Genes Dev. 10:176-84; Malicki et al., 1990, Cell 63: 961-967).

Outside their well-defined roles in segmentation, HOX genes play important roles in organogenesis. For example, HOX genes are involved in neural crest differentiation (e.g. Maconochie et al., 1999, Development 126:1483-1494), cardiovascular development (reviewed by Patterson et al., 1998, Curr. Top. Dev. Biol. 40:1-44) and hematopoiesis (Shimamoto et al., 1998, Int. J. Hematol. 67:339-250).

HOX genes are expressed in cells of erythroid, myeloid and lymphoid lineages. A limited number of studies has been carried out to assess the function of HOX genes in the differentiation of hematopoietic lineages. Data from antisense and knockout approaches are summarized in FIG. 9, and suggest that HOX genes are involved in many stages of hematopoietic development. It is almost certain that future studies will reveal further roles for HOX genes in hematopoiesis.

2.2.4. Dispersed (Non-HOX) Homeobox Genes and Homeodomain Proteins

DLX genes code for DNA-binding proteins with homeodomain motifs. The first of these genes to be identified was the *Drosophila* Distal-less (Dll) gene, which is required for the development of ventral appendages, i.e. the legs and antennae (Gorfinkiel et al., 1997). Dll mutant flies exhibit malformation of these appendages, including deletion of the appendages' distal portions (Cohen et al., 1989, Nature 338: 432-4). Mammalian DLX genes are required for forebrain and craniofacial development (see e.g. Ellies et al., 1997, Mech. Dev. 61:23-36). Additional roles have been suggested, for example in hematopoiesis (Shimamoto et al., Proc. Natl. Acad Sci. USA 94:3245-3249).

odomain (when compared to traditional homeodomain proteins). Outside the homeodomain, PBC proteins have domains of high conservation called PBC-A and PBC-B (Burglin et al., 1992, Nat Genet. 1:319-20). In *Drosophila*, the PBC protein Extradenticle (EXD) functions as a HOX transcriptional cofactor (Mann and Chan, 1996, Trends Genet. 12:258-262) and as such determines the outcome of HOX activity, but also has non-HOX functions such as antennal determination. PBC proteins in mammals are involved in the regulation of hematopoiesis, and a fusion of the PBC protein PBX-1 with E2A that results of a t(1;19) translocation is observed in pre-B cell acute lymphoblastic leukemias (LeBrun and Cleary, 1994, Oncogene 9:1641-1647).

MEIS and related proteins such as KNOX are thought to have arisen from a common ancestor with PBX proteins (Burglin, 1998, Dev. Genes Evol. 208:113-116). MEIS proteins have a conserved domain called the HM or MH domain (Rieckhof et al., 1997, Cell 91:171-183; Pai et al., 1998, Genes Dev. 12:435-446), which comprises two subdomains called HM 1 and HM2. The developmental and cell fate requirements for MEIS proteins are likely to be very similar to those of PBC proteins, as the former are thought to be required for the nuclear localization of the latter (Rieckhof et al., 1997, Cell 91:171-183; Pai et al., 1998, Genes Dev. 12:435-446). Conversely, at least in *Drosophila*, EXD is required to stabilize the MEIS protein HTH (Abu-Shaar and Mann, 1998, Development 125:3821-3830). Thus, while to date it has not been possible to separate the individual roles of PBC and MEIS proteins in cell fate specification, it is clear that both sets of genes work in concert to determine cell fates during development and hematopoiesis.

LIM domains are double zinc finger motifs found in a diverse group of proteins. The LIM domain serves primarily as a protein-protein interaction motif (Dawid et al., 1998, Trends Genet. 14:156-162). One particularly important group of LIM domain proteins are the LIM homeodomain proteins, which have a homeodomains in addition to the LIM domain. In these proteins, the LIM domain functions as a negative regulatory element for DNA binding by the homeodomain (Dawid et al., 1998, Trends Genet. 14:156-162). It has also been suggested the LIM domain itself is involved in DNA binding (Sanchez-Garcia and Rabbitts, 1994, Trends Genet. 10:315-320). LIM homeodomain proteins specify motor neuron identity (Thor et al., 1999, Nature 397:76-80 and references therein), as well as neuron identity in *C. elegans* (Hobert et al., 1998, J. Neurosci 18:2084-2096) and *Drosophila* (Lundgren et al., 1995, Development 121:1769-1773). Other known roles for LIM homeodomain proteins include appendage formation (e.g. wing formation in *Drosophila*, Stevens and Bryant, 1995, Genetics 110:281-297) and hematopoiesis (Porter et al., 1997, Development 124:2935-2944; Pinto et al., 1998, EMBO J. 17:5744-5756). LIM-homeodomain function is conserved across species, as murine orthologs can functionally substitute for *Drosophila* genes (Rincon-Limas et al., 1999, Proc. Natl. Acad. Sci. USA 96:2165-2170).

In addition to their homeodomains, POU proteins have a DNA binding domain called the POU domain (PIT1, Oct1/Oct2; Unc-86). Pit1 is required for pituitary and hyopthalamic development (Ryan et al., 1997, Genes Dev. 11:1207-1225).

PTX1 and PTX2 are homeodomain proteins of the bicoid class, and are necessary for pituitary development (Drouin et al., 1998, Mol. Cell. Endocrinol. 140:31-36). A mutation of PTX2 in humans results in Rieger's syndrome.

MSX genes encode homeodomain proteins related to the *Drosophila* msh (muscle specific homeobox)-encoded protein. MSX proteins are present in a variety of mammalian tissues (Davidson, 1995, Trends Genet. 11:405-411). MSX-1 and MSX-2 are associated with the formation of skin appendages (Noven et al., 1995, J. Invest. Dermatol. 104:711-719).

Another set of divergent homeodomain proteins is encoded by NKX genes. These genes are important for neuronal and muscular differentiation. For example, NKX2-5 and tinman are required for cardiac development of mammals and *Drosophila*, respectively (Patterson et al., 1998, Curr. Top. Dev. Biol. 40:1-44).

2.2.5. Other Transcription Factors

The *Drosophila* vestigial (vg) gene encodes a nuclear protein with a possible protein-protein interaction domain (Williams et al., 1991, Genes Dev. 5:2481-95). vg mutant phenotypes include a reduction of the fly's wings to vestiges and a reduction or absence of the halteres (see e.g., Fristrom, 1968, J. Cell Biol. 39:488-491). When expressed ectopically, VG can induce wing and haltere formation (Kim et al., 1996, Nature 382:133-138; Weatherbee et al., 1996, Genes Dev. 12:1474-1482).

MADS box genes encode transcription factors with a DNA binding domain called the MADS domain. These genes are conserved in yeast, plants, *Drosophila* and mammals (Shore et al., 1995, Eur. J. Biochem. 229:1-13). Two of these genes, SRF and MEF2, are required for skeletal muscle differentiation (Duprey and Lesens, 1994, Int. J. Dev. Biol. 38:591-604).

The bHLH motif is one of the first DNA binding domains to be characterized. The MyoD family of bHLH proteins activate a program of muscle differentiation (Megeney et al., 1995, Biochem. Cell Biol. 73:723-32). The mammalian achaete-scute homolog MASH-1 is necessary for the differentiation of the autonomic neuronal lineage at the time that neural crest cells migrate to peripheral tissues (Anderson et al., 1997, Cold Spring Harbor Symp. Quan. Biol. 62:493-504); further experiments suggest a role for MASH-1 in the differentiation of neuroepithelial cells from a neural stem cell population (Torii et al., 1999, Development 126:443-456).

SOX genes encode HMG domain proteins related to the mammalian SRY sex-determining gene. The expression patterns of these genes are very suggestive of roles in organ and tissue development and differentiation (Prior et al., 1996, Mol. Med. 2:405-412). The few functional studies available show this to be true. For example, Schilham et al. (1996, Nature 380:711-4) demonstrate that in mice lacking SOX-4, the development of the B-cell lineage is halted at the pro-B-cell stage, and no terminal B-cell differentiation takes place.

Finally, T-box genes encode transcription factors with an approximately 200 amino acid DNA binding domain called the T-domain. T-box gene families have been conserved in metazoan evolution, as told by analysis of T-box genes from *C. elegans, Drosophila*, urodele, *Xenopus*, mouse and human (Agulnik et al., 1995, Genomics 25:214-219). T-box genes are implicated in a broad variety of developmental events, including the determination of limb identity in vertebrates (see e.g. Simon, 1999, Cell Tissue Res. 296:57-66; Logan et al., 1998, development 125:2825-2835), mesoderm and notochord specification in *Xenopus* (Horb and Thomsen, 1997, Development 124:1689-1698) and paraxial mesoderm (including somite) formation in mice (Chapman and Papioannou, 1998, Nature 391:695-697 show that in Tbx6 mutant mice, the somites are transformed into neural tubes).

2.2.6. Signaling Molecules

Signaling molecules provide the cues that trigger most cell fate changes during metazoan differentiation and development. Most signaling pathways culminate in changes in transcriptional activity of the cells receiving the signal. These changes include the activation of many of the cell fate control transcription factor pathways described above, often mediated by transcription factors that are specific to the signaling pathways and which respond to changes in signaling activity by acquiring the ability to activate/repress certain genes and/or losing the ability to activate/repress others. Signaling molecule families that mediate growth and differentiation include the TGF-$\beta$ (transforming growth factor $\beta$) and BMP (bone morphogenetic protein) superfamily, the WNT family and the HH (hedgehog) family. These signaling molecule families are described extensively in the following review articles:

TGF-$\beta$/BMP: Massague, 1998, Annu. Rev. Biochem. 67:753-791; Zou et al., 1997, Cold Spring Harb. Symp. Quant. Biol. 62:269-272; Heikinheimo et al., 1998, Eur. J. Oral Sci. 106 Suppl. 1:167-173; Basile and Hammerman, 1998, Miner. Electrolyte Metab. 24:144-148; Perrell et al., Miner. Electrolyte Metab. 24:136-143; Moses and Serra, 1996, Curr. Opin. Genet. Dev. 1996, 6:581-586; Kolodziejczyk and Hall, 1996, Biochem. Cell Biol. 74:299-314; Unsicker et al., 1996, Ciba Found. Symp. 196:70-84; Martin et al., 1995, Ann. NY Acad. Sci. 752:300-308; Wall and Hogan, 1994, Curr. Opin. Genet. Dev. 4:517-522; Hogan et al., 1994, Dev. Suppl. 1994: 53-60.

WNT: Wodarz and Nusse, 1998, Annu. Rev. Cell Dev. Biol. 14:59-88; Cadigan and Nusse, 1997, Genes Dev. 11:3286-3305; Siegfried and Perrimon, 1994, Bioessays 16:395-404; Dickinson and McMahon, 1992, Curr. Opin. Genet. Dev. 2:562-566.

HH: Goodrich and Scott, 1998, Neuron 21:1243-1257; Pepicelli et al., 1998, Curr. Biol. 8:1083-1086; Ming et al., 1998, Mol. Med. Today 4:343-349; Weed et al., 1997, Matrix Biol. 16:53-58; Burke and Basler, 1997, Curr. Opin. Neurobiol. 7:55-61; Hammerschmidt et al., 1997, Trends Genet. 13:14-21; Ingham, 1995, Curr. Opin. Genet. Dev. 5:492-498.

Citation or identification of any reference in Section 2 or any other section of this application shall not be construed as an admission that such reference is available as prior art to the present invention.

3. SUMMARY OF THE INVENTION

The present invention provides methods for altering the fate of a cell, tissue or organ type by altering Notch pathway function in the cell. The invention further provides methods for altering the fate of a cell, tissue or organ type by simultaneously changing the activation state of the Notch pathway and one or more cell fate control gene pathways. The methods of the invention can be directed to cells of any differentiation state. The resulting cells can be used in cell replacement therapy to repopulate lost cell populations and help in the regeneration of diseased and/or injured tissues. The resulting cell populations can also be made recombinant and used for gene therapy or as tissue/organ models for research or as bioreactors for the large scale production of therapeutically useful proteins. The invention provides methods of of treating macular degeneration comprising altering Notch pathway function in retinal pigment epithelium cells or neuroepithelium cells. The present invention also provides kits for altering cell fate by using the methods provided by the invention. The invention also provides methods for screening agonists or antagonists of Notch and cell fate control gene pathway function.

The invention provides a method for altering the cell fate otherwise adopted by a cell by altering Notch and a cell fate control gene pathway function concurrently in the cell, then subjecting the cell to conditions that allow cell fate determination to occur. In a specific embodiment, the method comprises contacting the cell with an agonist of Notch function and an agonist of a cell fate control gene pathway. In another specific embodiment, the method comprises contacting the cell with an agonist of Notch function and an antagonist of a cell fate control gene pathway function. In yet another specific embodiment, the method comprises contacting the cell with an antagonist of Notch function and an agonist of a cell fate control gene pathway function. In an alternative specific embodiment, the method comprises contacting the cell with an antagonist of Notch function and antagonist of a cell fate control gene pathway function.

In certain embodiments of the present methods, the agonist of Notch pathway function is a dominant-active Notch mutant. In other embodiments, the agonist is purified. In yet other embodiments, the antagonist of Notch pathway function is a dominant-negative Notch mutant. In yet other embodiments, the antagonist is purified.

In certain embodiments of the methods of the present invention, the agonist or antagonist of Notch pathway function and the agonist or antagonist of cell fate control gene pathway function can be nucleic acids. Thus, in one embodiment, the methods comprise introducing into the cell one or more nucleic acids encoding an agonist of Notch pathway function and an agonist of a cell fate control gene pathway function such that the agonists are expressed by the cell. In another embodiment, the methods comprise introducing into the cell one or more nucleic acids encoding an agonist of Notch pathway function and an antagonist of a cell fate control gene pathway function such that the agonist and antagonist are expressed by the cell. In yet another embodiment, the method comprise introducing into the cell one or more nucleic acids encoding an antagonist of Notch pathway function and an agonist of a cell fate control gene pathway function such that the antagonist and agonist are expressed by the cell. In yet another embodiment, the methods comprise introducing into the cell one or more nucleic acids encoding an antagonist of Notch pathway function and an antagonist of a cell fate control gene pathway function such that the antagonists are expressed by the cell.

In certain embodiments of the methods of the present invention, the agonist or antagonist of Notch pathway function and the agonist or antagonist of cell fate control gene pathway function can be administered to an organism comprising the cell whose fate is to be altered. Thus, in one embodiment, the methods comprise administering to an organism comprising the cell an agonist of Notch pathway function and an agonist of a cell fate control gene pathway function. In another embodiment, the methods comprise administering to an organism comprising the cell an agonist of Notch pathway function and an antagonist of a cell fate control gene pathway function. In yet another embodiment, the methods comprise administering to an organism comprising the cell an antagonist of Notch pathway function and an agonist of a cell fate control gene pathway function. In yet other embodiments, the methods comprise administering to an organism comprising the cell an antagonist of Notch pathway function and an antagonist of a cell fate control gene pathway function.

In one embodiment, the method of the invention further comprises expanding the cell by subjecting the cell to cell growth conditions to produce a population of cells.

The invention also provides a method of treating a patient by provision of a cell transplant comprising producing cells of a particular cell fate according to the method of the invention, and administering the cells to the patient. In a specific embodiment, the cell transplant is an organ transplant.

The invention further provides methods of treating macular degeneration comprising agonizing Notch pathway function in retinal pigment epithelium and/or the retinal neuroepithelium.

The invention also provides a method for changing the cell fate of a mature cell type comprising antagonizing Notch pathway function in the cell; then contacting the cell in vitro with an agonist of Notch function and altering the function of a cell fate control gene pathway in the cell; and subjecting the cell to conditions that allow cell fate determination to occur.

The invention also provides a method for altering the cell fate otherwise adopted by a cell comprising altering Notch pathway function in the cell by a method comprising contacting the cell in vitro with or administering to an organism comprising the cell an agonist or antagonist of Notch pathway function in the cell and subjecting the cell to conditions that allow cell fate determination to occur while carrying out the alteration to Notch pathway function, until a cell of an altered cell fate is produced.

The invention also provides a method for producing an organ of a different type than would be otherwise produced by one or more cells by comprising altering Notch pathway function in one or more cells by a method comprising contacting the cells in vitro with or administering to an organism comprising the cells an agonist or antagonist of Notch pathway function in the organ and subjecting the cells to conditions that allow organ differentiation and cell growth to occur while maintaining the alteration to Notch pathway function, until a population of cells forming an organ is produced.

In one mode of the invention, altering Notch pathway function and optionally the cell fate control gene pathway function are carried out in vitro. In an alternative mode of the invention, altering Notch pathway function and optionally the cell fate control gene pathway function are carried out in vivo.

In a specific embodiment, the cell fate produced in a cell by the Notch pathway and optionally the cell fate control gene pathway is apoptosis. In a preferred mode of the embodiment, the cell is a cancer cell. In another embodiment, the cell fate altered by the Notch pathway and optionally the cell fate control gene pathway is apoptosis, i.e., the cell fate that would have been otherwise adopted by a cell is apoptosis.

The invention provides a method for screening agonists or antagonists of Notch pathway function, comprising altering a cell fate control gene pathway function in a cell, contacting the cell with or recombinantly expressing within the cell one or more test agonists or antagonists of Notch pathway function while subjecting the cell to conditions that allow cell fate determination to occur, and examining the cell for an alteration in cell fate as compared to a cell not contacted with or expressing the test agonists or antagonists.

The invention provides a method for screening agonists or antagonists of cell fate control gene pathway function, comprising altering Notch pathway function in a cell, contacting the cell with or recombinantly expressing within the cell one or more test agonists or antagonists of a cell fate control gene pathway function while subjecting the cell to conditions that allow cell fate determination to occur, and examining the cell for an alteration in cell fate as compared to a cell not contacted with or expressing the test agonists or antagonists.

The invention also provides a kit comprising in one or more containers a first molecule that alters Notch function; and a second molecule that alters a cell fate control gene pathway function. In one embodiment, the first molecule is an agonist of Notch function. In an alternative embodiment, the first molecule is an antagonist of Notch function. In a further embodiment, the second molecule is an agonist of a cell fate control gene pathway function. In an alternative further embodiment, the second molecule is an antagonist of a cell fate control gene pathway function.

In a specific embodiment, the cell fate control gene is not vestigial (vg), Distal-less (Dll), Antennapedia (Antp), eyeless (ey) or twin of eyeless (toy), and/or alteration in cell fate does not result in a change in type of appendage produced in *Drosophila*.

4. BRIEF DESCRIPTION OF THE FIGURES

FIG. 1(A-F). Eye reduction and ectopic eye induction by the inhibition and the activation of Notch signaling driven by ey-GAL4.

(A) UAS-$N^{dn}$ ey-GAL4 fly lacking eye.

(B) UAS-$N^{act}$ ey-GAL4 fly shows hyperplasia of the eye and an ectopic eye on the rostral membrane of the head.

(C) β-galactosidase staining of the third instar eye-antennal imaginal disc shows the activation of a UAS-lacZ reporter construct by the ey-GAL4. Bar indicates 50 µm.

(D) Scanning electron micrograph of an ectopic eye (arrowhead) on the head of a UAS-$N^{act}$ ey-GAL4 fly. The ectopic eye contains ommatidia with interommatidial bristles.

(E) Anti β-galactosidase antibody staining. Activation of the lacZ reporter reflects the distribution of constitutively activated Notch protein. Arrowhead indicates hyperplastic portion.

(F) Immunostaining of same disc as in (E) with antibody against the neuronal marker ELAV, In the hyperplastic portion (arrowhead), ectopically induced photoreceptor cells can be seen. Posterior is to the left and dorsal is up in (C), (E)-(F).

FIG. 2(A-B). Ectopic induction of eyeless in eye-antennal discs by the activation of Notch signaling driven by ey-GAL4.

(A) Anti β-galactosidase antibody staining of an eye-antennal disc from a UAS-$N^{act}$ UAS-lacZ ey-GAL4 larva. Activation of the lacZ reporter construct reflects the distribution of constitutively activated Notch protein. Arrowheads indicate areas of strong lacZ expression. Bar indicates 50 µm.

(B) Immunostaining of same disc as in (A) with antibody against EY. Ectopic ey expression is induced in the areas of strong lacZ expression (arrowheads).

FIG. 3(A-B). Requirement of Notch signaling for eyeless expression during eye development. Su(H) mutant clones were induced in eye discs using a mitotic clonal analysis technique. (Struhl, 1982, Proc. Natl. Acad. Sci. USA 79:7380-7384).

(A) The Su(H) mutant clones are detected by the lack of MYC staining. Arrowheads indicate the clone. Bar indicates 16 µm.

(B) The Su(H) mutant clones that formed anteriorly to the morphogenic furrow in the eye disc fail to express EY. Posterior is to the left and dorsal is up in all panels.

FIG. 4(A-B). Induction of ectopic antennae in ey mutants by the activation of Notch signaling driven by ey-GAL4.

(A) Many of the UAS-$N^{act}$ ey-GAL4 $ey^2$ flies show strongly reduced eyes. Some of these flies show a reduced original eye (arrow) and also an induced ectopic eye (arrowhead).

(B) With relatively high frequency (about 25%), the activation of Notch signaling driven by ey-GAL4 induces ectopic antennae in ey mutants. Scanning electron micrograph of an ectopic antenna (arrowhead) that is formed on the lateral side of the head of UAS-$N^{act}$ ey-GAL4 $ey^2$ fly instead of an original eye. Arrowhead indicates an original antenna. 1; first segment, 2; second segment, 3; third segment of the antenna, a; arista.

FIG. 5(A-B). Induction of ectopic wing and leg structure on the head by the activation of Notch signaling and the simultaneous ectopic expression of Antennapedia.

(A) Scanning electron micrograph of an ectopic wing that is formed on the lateral side of the head of a UAS-$N^{act}$ UAS-Antp ey-GAL4 fly replacing the original eye. Arrowhead indicates the wing margin bristles with double and triple row.

(B) Scanning electron micrograph of an ectopic leg arising by transformation of the distal parts of an ectopically induced antenna (arrowhead) on the head of an UAS-$N^{act}$ UAS-Antp ey-GAL4 fly. Arrow indicates original antenna. Numbers refer to the five tarsal segments of the ectopic leg. c; claw of the ectopic leg, w; ectopic wing margin bristles, e; reduced original eye.

FIG. 6(A-D). Ectopic induction of Distal-less in $eyeless^2$ (Schneuwly et al., 1987, Nature 325:816-818) mutant eye-antennal discs by the activation of Notch signaling driven by ey-GAL4.

(A) Bright field micrograph of an eye-antennal disc of UAS-$N^{act}$ ey-GAL4 $ey^2$ larva.

(B) Immunostaining of same disc as in (A) with antibody against DLL. Ectopic DLL expression is induced in the eye disc (arrowhead). Arrow indicates original DLL expression in the antennal disc. Bar indicates 50 µm.

(C) Bright field micrograph of an eye-antennal disc of a UAS-$N^{act}$ ey-GAL4 larva.

(D) Immunostaining of the same disc as in (C) with antibody against DLL. Ectopic DLL expression is induced in a few cells of the antennal disc (arrowhead). Arrow indicates original DLL expression in the antennal disc. Bar indicates 50 µm. Posterior is to the left and dorsal is up in all panels.

FIG. 7(A-D). Ectopic induction of vestigial in the eye discs by the activation of Notch signaling and the simultaneous ectopic expression of Antennapedia driven by ey-GAL4.

(A) Bright filed micrograph of an eye-antennal disc of UAS-$N^{act}$ UAS-Antp ey-GAL4 larva.

(B) Immunostaining of the same disc as in (A) with antibody against VG. Ectopic VG expression is induced in the eye disc.

(C) Bright field micrograph of an eye-antennal disc of UAS-Antp ey-GAL4 larva.

(D) Immunostaining of same disc as in (C) with antibody against VG. Ectopic vg expression is induced in a small region of the eye disc. Posterior is to the left and dorsal is up in all panels. Bars indicate 50 μm.

FIG. 8(A-D). Repression of the Distal-less expression by the ectopic expression of eyeless driven by dpp-GAL4.

(A) Wild type expression of DLL in eye-antennal disc.

(B) Wild type expression of EY in eye-antennal disc.

(C) Immunostaining of the eye-antennal disc of UAS-ey dpp-GAL4 larva with antibody against DLL. Arrowhead indicates the repression of DLL in the region of ectopic ey expression.

(D) Immunostaining of same disc as in (D) with antibody against EY. Arrowhead indicates the ectopic expression of ey in the antennal disc. Bars indicate 50 μm.

Figure 9:
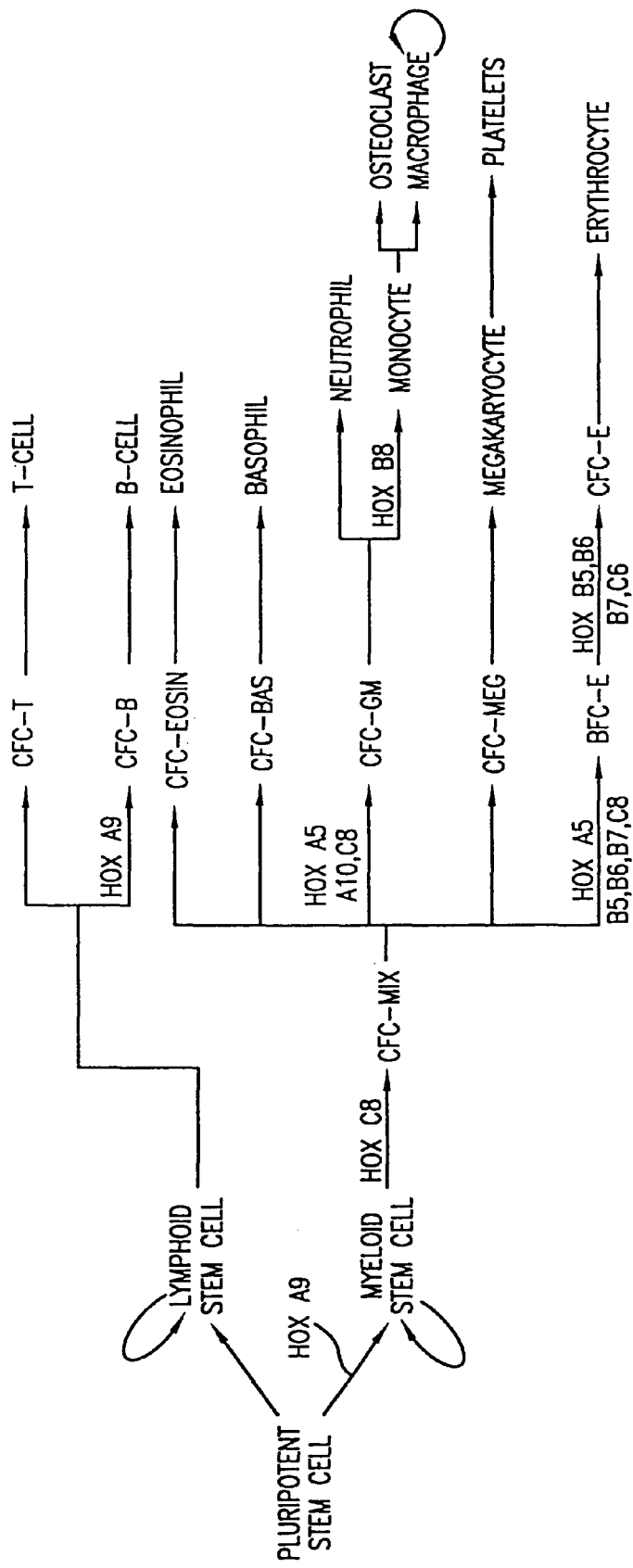

FIG. 9. A schematic representation of the roles of HOX genes in hematopoiesis. Abbreviations used in the figure: CFC, colony-forming cells; BFC, burst-forming cells; CFC-E, erythrocyte colony-forming cells; BFC-E, erythrocyte burst forming-cells; CFC-MEG, megakaryocyte colony-forming cells; CFC-GM, granulocyte/macrophage colony-forming cells; CFC-Bas, basophil colony-forming cells; CFC-Eosin, eosinophil colony-forming cells; CFC-B, B-cell colony-forming cells; CFC-T, T-cell colony-forming cells. Table adapted from p. 1168 of Alberts et al., 1994, Molecular Biology of the Cell, 3$^{rd}$ ed., Garland Publishing, Inc., New York & London.

5. DETAILED DESCRIPTION OF THE INVENTION

The present invention provides methods for altering the fate of a cell, tissue or organ type by altering Notch pathway function in the cell. The invention further provides methods for altering the fate of a cell, tissue or organ type by simultaneously changing the activation state of the Notch pathway and a cell fate control gene pathways. The methods of the invention can be directed to cells of any differentiation state. The resulting cells can be used in cell replacement therapy to repopulate lost cell populations and help in the regeneration of diseased and/or injured tissues. The resulting cell populations can also be made recombinant and used for gene therapy or as tissue/organ models for research or as bioreactors for the large scale production of therapeutically useful proteins. The invention provides methods for of treating macular degeneration comprising altering Notch pathway function in retinal pigment epithelium cells and/or retinal neuroepithelial cells. The present invention also provides kits for altering cell fate by using the methods provided by the invention.

The invention provides a method for altering the cell fate otherwise adopted by a cell by altering Notch and a cell fate control gene pathway function prior in the cell, then subjecting the cell to conditions that allow cell fate determination to occur. In a specific embodiment, the method comprises contacting the cell with an agonist of Notch function and an agonist of a cell fate control gene pathway. In a specific embodiment, the method comprises contacting the cell with an agonist of Notch function and an agonist of a cell fate control gene pathway function. In another specific embodiment, the method comprises contacting the cell with an agonist of Notch function and an antagonist of a cell fate control gene pathway function. In yet another specific embodiment, the method comprises contacting the cell with an antagonist of Notch function and an agonist of a cell fate control gene pathway function. In an alternative specific embodiment, the method comprises contacting the cell with an antagonist of Notch function and antagonist of a cell fate control gene pathway function.

In one embodiment, the method of the invention further comprises expanding the cell by subjecting the cell to cell growth conditions to produce a population of cells.

The invention also provides a method of treating a patient by provision of a cell transplant comprising producing cells of a particular cell fate according to the method of the invention, and administering the cells to the patient.

The invention further provides methods of treating macular degeneration comprising agonizing Notch pathway function in retinal pigment epithelium or retinal neuroepithelium.

The invention also provides a method for changing the cell fate of a mature cell type comprising antagonizing Notch pathway function in the cell; then concurrently contacting the cell in vitro with an agonist of Notch function and altering the function of a cell fate control gene pathway in the cell; and subjecting the cell to conditions that allow cell fate determination to occur.

In one mode of the invention, altering Notch pathway function and optionally the cell fate control gene pathway function are carried out in vitro. In an alternative mode of the invention, altering Notch pathway function and optionally the cell fate control gene pathway function are carried out in vivo.

The invention also provides a method for altering the cell fate otherwise adopted by a cell comprising altering Notch pathway function in the cell by a method comprising contacting the cell in vitro with or administering to an organism comprising the cell an agonist or antagonist of Notch pathway function in the cell and subjecting the cell to conditions that allow cell fate determination to occur while carrying out the alteration to Notch pathway function, until a cell of an altered cell fate is produced.

The invention also provides a method for producing an organ of a different type than would be otherwise produced by one or more cells by comprising altering Notch pathway function in one or more cells by a method comprising contacting the cells in vitro with or administering to an organism comprising the cells an agonist or antagonist of Notch pathway function in the organ and subjecting the cells to conditions that allow organ differentiation and cell growth to occur while maintaining the alteration to Notch pathway function, until a population of cells forming an organ is produced. Examples of organs that can be produced by the methods of this specific embodiment include liver, lung, pancreas, skin, cartilage, bone, intestine, heart, kidney, etc.

In a specific embodiment, the cell fate produced in a cell by the Notch pathway and optionally the cell fate control gene pathway is apoptosis. In a preferred mode of the embodiment, the cell is an immortalized cell, e.g., a cancer cell. In another embodiment, the cell fate altered by the Notch pathway and optionally the cell fate control gene pathway is apoptosis, i.e., the cell fate that would have been otherwise adopted by a cell is apoptosis.

The invention also provides a kit comprising in one or more containers a first molecule that alters Notch function; and a second molecule that alters a cell fate control gene pathway function. In one embodiment, the first molecule is an agonist of Notch function. In an alternative embodiment, the first molecule is an antagonist of Notch function. In a further embodiment, the second molecule is an agonist of a cell fate control gene pathway function. In an alternative further embodiment, the second molecule is an antagonist of a cell fate control gene pathway function.

As used herein, a cell fate control gene is a gene that is necessary or sufficient for the determination of the fate of at least one cell type, the fate being differentiation (e.g., commitment to a particular lineage, tissue of organ type, or mature cell type), proliferation, or programmed cell death. Any gene that fulfils this criterion is encompassed by this invention. In a preferred embodiment, a cell fate control gene is a transcription factor, more preferably a homeobox containing gene, and most preferably a HOX or DLX or PAX gene. In another preferred embodiment, a cell fate control gene encodes a signaling molecule, preferably a WNT, TGF-β/BMP or HH molecule. In a specific embodiment, the cell fate control gene is not vestigial (vg), Distal-less (Dll), Antennapedia (Antp), eyeless (ey) or twin of eyeless (toy), and/or alteration in cell fate does not result in a change in type of appendage produced in *Drosophila*.

A cell that has altered cell fate, produced after the activities of the Notch pathway and a cell fate control gene pathway in the cell are altered concurrently according to the methods of the present invention, is herein called a "Manipulated" cell.

As used herein, "precursor cells" shall mean any cells of any differentiation state. The precursor cells may be manipulated in vivo without the need for isolation. The precursor cells may be isolated from a precursor cell-containing population before or after the manipulation of the precursor cell type. In a specific embodiment, the precursor cells are non-terminally differentiated cells, e.g., are stem cells or progenitor cells.

Activation of the Notch pathway is preferably achieved by contacting the cell with a Notch ligand, e.g., in soluble form or recombinantly expressed on a cell surface or immobilized on a solid surface, or by introducing into the cell a recombinant nucleic acid expressing a dominant active Notch mutant or an activating Notch ligand, or any other molecule that activates the Notch pathway. When the cell fate control gene is a transcription factor, activation of the cell fate control gene pathway function is preferably achieved by introducing into the cell a recombinant nucleic acid expressing the cell fate control, or by contacting the cell with recombinantly expressed cell fate control protein functionally coupled to an internalization signal peptide. If the cell fate control gene is a signaling molecule, the cell fate control gene pathway function is preferably activated by contacting the cell with recombinantly expressed signaling molecule, or by contacting the cell with a recombinant nucleic acid expressing an activated form of a pathway component, e.g. a constitutively activated receptor or signal transducing DNA binding protein. Where the agonists or antagonists of the invention are recombinantly expressed in the cell, they can be expressed constitutively or under the control of an inducible promoter.

The present invention is also directed to Manipulated cells expressing recombinant genes, such that the precursor cells express a desired gene. These recombinant Manipulated cells can be transplanted into a patient such that the desired gene is expressed in the patient to alleviate a disease state caused by the lack of expression of the recombinant gene. The Manipulated cells can be made recombinant either before or after precursor cell expansion. Methods of transfecting the nucleic acid encoding the desired gene product such that the Manipulated cell or its progeny stably expresses the gene product are known to those of skill in the art and are described infra.

The subject into which the Manipulated cells are introduced, or from which precursor cells can be derived, is preferably an animal, including but not limited to animals such as cows, pigs, horses, chickens, cats, dogs, etc., and is preferably a mammal, and most preferably human.

In one embodiment, the Manipulated cells can be administered to a patient wherein the differentiation phenotype is therapeutically useful. Alternatively, the Manipulated cells can be used to replace or supplement the corresponding cell type in a patient by administration of said cell population. In another embodiment, the Manipulated cells are used to coat prosthetic implants. Whenever Manipulated cells are used to treat a patient in vivo, it is preferred that the source of the precursor cells is the patient himself (i.e., the transplant is autologous), the autologous transplant circumventing the need for immunosuppressive drugs. However, the transplant need not be autologous. Administration of Manipulated cells is achieved by methods known to those skilled in the art (see Section 5.8, infra). In another embodiment, the Manipulated cells are maintained in culture for use as tissue or organ models for research, including medical research. In a preferred mode of the embodiment, the tissue or organ models are treated with an infectious agent then used to determine the effects of drugs on the diseased as well as the non-diseased tissue or organ. In another mode of the embodiment, the tissue or organ models are contacted with hormones or growth factors to determine the effects of the hormones or growth factors on the tissue or organ. In yet another embodiment, the Manipulated cells are used as bioreactors for the large scale production of therapeutically useful proteins. The present invention is also directed to kits for altering cell fate by using the methods provided by the invention.

For clarity of disclosure, and not by way of limitation, the detailed description of the invention is divided into the following sub-sections:
—i—Recombinant expression of Notch and cell fate control gene pathway components;
—ii—Notch signaling and differentiation;
—iii—Agonists of Notch Pathway Function;
—iv—Antagonists of Notch Pathway Function;
—v—Cell fate control genes and proteins;
—vi—Activation of cell fate control gene pathways;
—vii—Inhibition of cell fate control gene pathways;
—viii—Screening for Notch and Cell Fate Control Gene Pathway Agonists and Antagonists;
—ix—Obtaining and culturing precursor cells;
—x—Gene therapy;
—xi—Uses of cells manipulated by the methods of the invention;
—xii—Methods of Transplantation; and
—xiii—Pharmaceutical compositions.

5.1. Recombinant Expression of Notch and Cell Fate Control Gene Pathway Components In specific embodiments, agonists and antagonists of Notch or cell fate control gene pathway function are recombinantly produced and then isolated for use, or are recombinantly expressed in the cell whose cell fate is altered according to the present invention.

The nucleotide sequence coding for Notch, a cell fate control protein, a Notch or cell fate gene pathway component, or for a functionally active fragment or other derivative thereof, which in this section is referred to as a "Gene of Interest", and the protein it encodes the "Protein of Interest", can be inserted into an appropriate expression vector, i.e., a vector which contains the necessary elements for the transcription and translation of the inserted protein-coding sequence. The necessary transcriptional and translational signals can also be supplied by the native gene and/or its flanking regions. A variety of host-vector systems may be utilized to express the protein-coding sequence. These include but are not limited to mammalian cell systems infected with virus (e.g., vaccinia virus, adenovirus, etc.); insect cell systems infected with virus (e.g., baculovirus); microorganisms such as yeast containing yeast vectors, or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used.

Any of the methods previously described for the insertion of DNA fragments into a vector may be used to construct expression vectors containing a chimeric gene consisting of appropriate transcriptional/translational control signals and the protein coding sequences. These methods may include in vitro recombinant DNA and synthetic techniques and in vivo recombinants (genetic recombination). Expression of nucleic acid sequence encoding a Protein of Interest thereof may be regulated by a second nucleic acid sequence so that the Protein of Interest is expressed in a host transformed with the recombinant DNA molecule. For example, expression of a Protein of Interest may be controlled by any promoter/enhancer element known in the art. Promoters which may be used to control cell fate control gene or cell fate gene pathway component expression include, but are not limited to, the SV40 early promoter region (Bernoist and Chambon, 1981, Nature 290:304-310), the promoter contained in the 3' long terminal repeat of Rous sarcoma virus (Yamamoto, et al., 1980, Cell 22:787-797), the herpes thymidine kinase promoter (Wagner et al., 1981, Proc. Natl. Acad. Sci. U.S.A. 78:1441-1445), the regulatory sequences of the metallothionein gene (Brinster et al., 1982, Nature 296:39-42); the regulatory sequence of the heat shock protein 70 gene (Bienz and Pelham, 1986, Cell. 45:753-60) prokaryotic expression vectors such as the β-lactamase promoter (Villa-Kamaroff, et al., 1978, Proc. Natl. Acad. Sci. U.S.A. 75:3727-3731), or the tac promoter (DeBoer, et al., 1983, Proc. Natl. Acad. Sci. U.S.A. 80:21-25); see also "Useful proteins from recombinant bacteria" in Scientific American, 1980, 242:74-94; plant expression vectors comprising the nopaline synthetase promoter region (Herrera-Estrella et al., Nature 303:209-213) or the cauliflower mosaic virus 35S RNA promoter (Gardner, et al., 1981, Nucl. Acids Res. 9:2871), and the promoter of the photosynthetic enzyme ribulose biphosphate carboxylase (Herrera-Estrella et al., 1984, Nature 310:115-120); promoter elements from yeast or other fungi such as the Gal 4 promoter, the ADH (alcohol dehydrogenase) promoter, PGK (phosphoglycerol kinase) promoter, alkaline phosphatase promoter, and the following animal transcriptional control regions, which exhibit tissue specificity and have been utilized in transgenic animals: elastase I gene control region which is active in pancreatic acinar cells (Swift et al., 1984, Cell 38:639-646; Ornitz et al., 1986, Cold Spring Harbor Symp. Quant. Biol. 50:399-409; MacDonald, 1987, Hepatology 7:425-515); insulin gene control region which is active in pancreatic beta cells (Hanahan, 1985, Nature 315:115-122), immunoglobulin gene control region which is active in lymphoid cells (Grosschedl et al., 1984, Cell 38:647-658; Adames et al., 1985, Nature 318:533-538; Alexander et al., 1987, Mol. Cell. Biol. 7:1436-1444), mouse mammary tumor virus control region which is active in testicular, breast, lymphoid and mast cells (Leder et al., 1986, Cell 45:485-495), albumin gene control region which is active in liver (Pinkert et al., 1987, Genes and Devel. 1:268-276), alpha-fetoprotein gene control region which is active in liver (Krumlauf et al., 1985, Mol. Cell. Biol. 5:1639-1648; Hammer et al., 1987, Science 235:53-58; alpha 1-antitrypsin gene control region which is active in the liver (Kelsey et al., 1987, Genes and Devel. 1:161-171), beta-globin gene control region which is active in myeloid cells (Mogram et al., 1985, Nature 315:338-340; Kollias et al., 1986, Cell 46:89-94; myelin basic protein gene control region which is active in oligodendrocyte cells in the brain (Readhead et al., 1987, Cell 48:703-712); myosin light chain-2 gene control region which is active in skeletal muscle (Sani, 1985, Nature 314:283-286), and gonadotropic releasing hormone gene control region which is active in the hypothalamus (Mason et al., 1986, Science 234:1372-1378).

In a preferred embodiment, a method that makes use of a tetracycline-regulated gene expression from *E. coli*, referred to as the "Tet system" (Gossen et al., 1995, Science 268:1766-1769; Gossen and Bujard, 1992, Proc. Natl. Acad. Sci. USA), is used to direct gene expression. In this case, transgenic cell lines are generated where the coding region for a tetracycline-controlled transcriptional activator (tTA) is operably fused to promoters/enhancers that direct the expression of tTA in a constitutive or inducible manner. The transgenic cell lines are generated where the coding region for the Gene of Interest to be mis-expressed is operably fused to a promoter that possesses a tTA-responsive regulatory element. When the cell culture food is supplemented with a sufficient amount of tetracycline, it completely blocks expression of the gene-of-interest in the resulting progeny. Expression of the gene-of-interest can be induced at will simply by removal of tetracycline from the food. Also, the level of expression of the gene-of-interest can be adjusted by varying the level of tetracycline in the food. Thus, the use of the Tet system as a binary control mechanism for mis-expression has the advantage of providing a means to control the amplitude and timing of mis-expression of the Gene of Interest. The Tet system can also be used in *Drosophila* and mice, where it has the advantage, depending on the promoter used for the rTA promoter, of providing spatial control as well as control of amplitude and timing. Preferred promoters in this embodiment are those that provide developmental tissue and/or stage specific control of gene expression.

Expression vectors containing a Gene of Interest can be identified by four general approaches: (a) nucleic acid hybridization; (b) molecular biology, (c) expression of inserted sequences; and (d) presence or absence of "marker" gene functions. In the first approach, the presence of a Gene of Interest inserted in an expression vector can be detected by nucleic acid hybridization using probes comprising sequences that are homologous to an inserted Gene of Interest. In the second approach, a combination of molecular biology and "marker" gene function are used to identify recombinant expression vectors containing the Gene of Interest. For example, if the Gene of Interest is inserted into a particular restriction site of an expression vector which codes for both antibiotic resistance, bacterial cells that take up the vector are identified by their resistance to the antibiotic, and those vectors containing the Gene of Interest can be identified by restriction digestion of the amplified vector DNA with the particular restriction enzyme. In the third approach, recombinant expression vectors can be identified by assaying the Protein of Interest expressed by the recombinant. Such assays can be based, for example, on the physical or functional properties of the Protein of Interest. In the fourth approach, the vector/host system can be identified based upon the presence or absence of certain "marker" gene functions (e.g., thymidine kinase activity, β-galactosidase, resistance to antibiotics, transformation phenotype, occlusion body formation in baculovirus, etc.) caused by the insertion of a Gene of Interest in the vector. For example, if the Gene of Interest is inserted within the marker gene sequence of the vector, recombinants containing the Gene of Interest can be identified by the absence of the marker gene function.

Once a particular recombinant DNA molecule is identified and isolated, several methods known in the art may be used to propagate it. Once a suitable host system and growth conditions are established, recombinant expression vectors can be propagated and prepared in quantity. As previously explained, the expression vectors which can be used include, but are not limited to, the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, to name but a few.

In addition, a host cell strain may be chosen which modulates the expression of the inserted sequences, or modifies and processes the gene product in the specific fashion desired. Expression from certain promoters can be elevated in the presence of certain inducers; thus, expression of the genetically engineered Protein of Interest may be controlled. Furthermore, different host cells have characteristic and specific mechanisms for the translational and post-translational processing and modification (e.g., glycosylation, cleavage [e.g., of signal sequence]) of proteins. Appropriate cell lines or host systems can be chosen to ensure the desired modification and processing of the foreign protein expressed. For example, expression in a bacterial system can be used to produce large quantities of transcription factors such as HOX proteins, as little or no posttranslational modification is required for their function. Expression in a eukaryotic cell will produce a glycosylated product, which is necessary for some proteins such as cell surface receptors. Expression in metazoan cells can be used to ensure "native" processing of the signal sequences of signaling molecules.

In other specific embodiments, the Protein of Interest may be expressed as a fusion, or chimeric protein product (comprising the peptide, fragment, analog, or derivative joined via a peptide bond to a heterologous protein sequence (of a different protein)). Such a chimeric product can be made by ligating the appropriate nucleic acid sequences encoding the desired amino acid sequences to each other by methods known in the art, in the proper coding frame, and expressing the chimeric product by methods commonly known in the art. Alternatively, such a chimeric product may be made by protein synthetic techniques, e.g., by use of a peptide synthesizer.

Both cDNA and genomic sequences can be cloned and expressed.

The methods described in this section are also applicable to genes and proteins that are not components of the Notch or cell fate control gene pathways, but to genes and proteins that may be used to indirectly alter the function of a gene or protein of the Notch or cell fate control gene pathways.

5.2. Notch Signaling and Differentiation

The Notch pathway is a signal transducing pathway comprising elements which interact, genetically and/or molecularly, with the Notch receptor protein. For example, elements which interact with the Notch protein on both a molecular and genetic basis are, for example, and not by way of limitation, Delta, Serrate and Deltex. Elements which interact with the Notch protein genetically are, for example, and not by way of limitation, Mastermind, Hairless, Suppressor of Hairless and Presenilin.

U.S. Pat. No. 5,780,300 describes the roles of Notch proteins in differentiation processes. Briefly, Notch regulates the competence of many different cell types to respond to differentiation/proliferation/apoptosis signals, with the particular cell fates chosen depending upon the developmental history of each cell type and the specific signaling pathways operating within it. The inventors have recently discovered (see Section 6, infra, that when Notch activity is altered in a sustained manner, or altered concurrently with changing the activity of one or more appropriate cell fate control genes or proteins, the response of the cell can be a change into a new cell type. Thus, precursor cells may be manipulated in vivo or ex vivo/in vitro in order to provide a source of cells that are useful in gene therapy as well as tissue repair.

In certain embodiments of the present invention, the desired cell population is treated in vitro with agonists or antagonists of the Notch pathway function and cell fate control gene pathway to alter their fates and then subjected to conditions under which they proliferate in culture before transplanting them back into the appropriate region, or directly transplant them without necessarily allowing them to proliferate in vitro. In one embodiment, the Manipulated cells are expanded by activation of the Notch pathway. In alternate embodiments, the cells are expanded, preferably by activation of the Notch pathway, prior to their manipulation by the methods of the present invention.

As described in U.S. Pat. No. 5,780,300, it is possible in many cases that the simple activation of Notch may not suffice to expand the precursor or Manipulated cells in vitro. Subjecting the cells to growth conditions, e.g., culturing them in the presence of specific growth factors or combinations of growth factors may be necessary.

5.3. Agonists of Notch Pathway Function

An agonist of Notch pathway function is an agent that promotes, i.e., causes or increases, activation of Notch pathway function. As used herein, "Notch pathway function" shall mean a function mediated by the Notch signaling pathway, including but not limited to nuclear translocation of Suppressor of Hairless or its mammalian homolog CBF1; activation of bHLH genes of the Enchancer of split complex, e.g. Mastermind; inhibition of *Drosophila* neuroblast segregation; and binding of Notch to Delta, Serrate, Deltex or Suppressor of Hairless, or homologs thereof.

Notch function activation is preferably carried out by contacting a precursor cell with a Notch function agonist. The agonist of Notch function can be a soluble molecule, recombinantly expressed as a cell-surface molecule, on a cell monolayer with which the precursor cells are contacted, a molecule immobilized on a solid phase. In another embodiment, the Notch agonist can be recombinantly expressed from a nucleic acid introduced into the precursor cells. Notch function agonists of the present invention include Notch proteins and analogs and derivatives (including fragments) thereof; proteins that are other elements of the Notch pathway and analogs and derivatives (including fragments) thereof; antibodies thereto and fragments or other derivatives of such antibodies containing the binding region thereof; nucleic acids encoding the proteins and derivatives or analogs; as well as toporythmic proteins and derivatives and analogs thereof which bind to or otherwise interact with Notch proteins or other proteins in the Notch pathway such that Notch function is promoted. Such agonists include but are not limited to Notch proteins and derivatives thereof comprising the intracellular domain, Notch nucleic acids encoding the foregoing, and proteins comprising toporythmic protein domains that interact with Notch (e.g., the extracellular domain of Delta, Serrate or Jagged). Other agonists include but are not limited to Deltex and Suppressor of Hairless. These proteins, fragments and derivatives thereof can be recombinantly expressed and isolated or can be chemically synthesized.

In another specific embodiment, the Notch function agonist is a cell which expresses a protein or fragment or derivative thereof, which agonizes Notch function. The cell expresses the Notch function agonist in such a manner that it is made available to the precursor cells, e.g., secreted, expressed on the cell surface, etc. In yet another specific embodiment, the Notch function agonist is a nucleic acid that encodes a protein or fragment or derivative thereof which agonizes Notch function; such an agonist can, for example, be employed or delivered according to the methods described in Section 5.6, infra.

In yet another specific embodiment, the agonist of Notch function is a peptidomimetic or peptide analog or organic molecule that binds to a member of the Notch signaling pathway. Such an agonist can be identified by binding assays selected from those known in the art.

In a preferred embodiment the agonist is a protein consisting of at least a fragment of the proteins encoded by toporythmic genes which mediate binding to Notch proteins or adhesive fragments thereof. Toporythmic genes, as used herein, shall mean the genes Notch, Delta, Serrate, Jagged, Suppressor of Hairless and Deltex, as well as other members of the Delta/Serrate/Jagged family or Deltex family which may be identified by virtue of sequence homology or genetic interaction and more generally, members of the "Notch cascade" or the "Notch group" of genes, which are identified by molecular interactions (e.g., binding in vitro, or genetic interactions (as depicted phenotypically, e.g., in Drosophila). Adhesive fragments of the toporythmic proteins cited above are described in U.S. Pat. Nos. 5,648,464; 5,849,869; and 8,856,441).

Vertebrate homologs of Notch pathway elements have been cloned and sequenced. For example, these include Serrate (Lindsell et al., 1995, Cell 80:909-917); Delta (Chitnis et al., 1995, Nature 375:761; Henrique et al., 1995, Nature 375: 787-790; Bettenhausen et al., 1995, Development 121:2407); and Notch (Coffman et al, 1990, Science 249:1438-1441; Bierkamp et al., 1993, Mech. Dev. 43:87-100; Stifani et al., 1992, Nature Genet. 2:119-127; Lardelli et al., 1993, Exp. Cell Res. 204:364-372; Lardelli et al., 1994, Mech. Dev. 46:123-136; Larsson et al., 1994, Genomics 24:253-258; Ellisen et al., 1991, Cell 66:649-661; Weinmaster et al., 1991, Development 113:199-205; Reaume et al., 1992, Dev. Biol. 154:377-387; Weinmster et al., 1992, Development 116:931-941; Franco del Amo et al., 1993, Genomics 15:259-264; and Kopan et al., 1993, J. Cell. Biol. 121:631-641).

In one embodiment, the Notch agonist is expressed from a recombinant nucleic acid. For example, in vivo expression of truncated, "activated" forms of the Notch receptor lacking the extra cellular, ligand binding domain results in gain of function mutant phenotypes. Preferably, the Notch dominant active mutant is expressed inside the precursor cells from an inducible promoter, such that expression can be induced in vitro for expansion and/or differentiation, with the inducer lacking in vivo so that the transplanted cells can respond to their environmental cues.

Alternatively, in another embodiment the agonist of Notch function is not a recombinant dominant Notch active mutant.

Alternatively, in another embodiment, contacting of the precursor cells with a Notch agonist is not done by incubation with other cells recombinantly expressing a Notch ligand on the cell surface (although in other embodiments, this method can be used).

In another embodiment, the recombinantly expressed Notch agonist is a chimeric Notch protein which comprises the intracellular domain of Notch and the extracellular domain of another ligand-binding surface receptor. For example, a chimeric Notch protein comprising the EGF receptor extracellular domain and the Notch intracellular domain is expressed in a precursor cell. However, the Notch pathway will not be active unless the EGF receptor ligand EGF is contacted with the precursor cell-expressing the chimera. As with the inducible promoter controlling the expression of the truncated form of Notch, the activity of the chimeric Notch protein is reversible; when EGF is removed from the cells, Notch activity will cease and the cell can then differentiate. Notch activity can again be turned on with the addition of the ligand. Preferably, the chimeric receptor is expressed under the control of an inducible promoter which is turned off prior to transplantation of the Manipulated cells, so that the transplanted cells do not respond to EGF in vivo by the activation of the Notch pathway.

A systematic deletion analysis of the intracellular domain of Notch demonstrates that the Notch sequences that are both necessary and sufficient for the downstream signaling of the Notch receptor are confined to the ankyrin repeats of the intracellular region (Matsuno et al., 1995, Development 121: 2633-2644 and unpublished results). Using the yeast two hybrid system it was discovered that the ankyrin repeats interact homotypically.

Expression of appropriate deletion constructs in the defined cellular environment of the developing Drosophila eye demonstrates that expression of a polypeptide fragment comprising just the ankyrin repeats resulted in an activated phenotype. Not surprisingly this is the part of the Notch protein which is most highly conserved among various species.

These findings suggest that any small molecules, for example, but not by way of limitation, polypeptides or antibodies which bind to the Notch ankyrin repeats, can block its function, and hence behave as antagonists of the pathway. Conversely, molecules that mimic the Notch ankyrin repeat activity can behave as agonists of the Notch pathway. Since the expression of truncated forms of Notch give mutant phenotypes in the developing Drosophila eye, genetic screens for modifiers of these phenotypes can be used for identifying and isolating additional gene products that can act as agonists or antagonists of the pathway.

Genes that act as enhancers of the activated phenotypes are potential agonists and those that act as suppressors are potential antagonists.

Deltex and Suppressor of Hairless are also agonists of Notch function that can be used. It has been shown that the activation of the Notch pathway, as judged by the induction of activated phenotypes similar to those induced by the expression of activated forms of Notch, can be achieved by manipulating the expression of Suppressor of Hairless (Schweisguth and Posakony, 1994, Development 120:1477), as well as Deltex (Matsuno et al., 1995, Development 121:2633) both of which can interact with the ankyrin repeats of Notch.

Using the yeast 'interaction trap' assay (Zervos et al., 1993, Cell 72:223-232), as well as cell culture co-localization studies, the protein regions responsible for heterotypic interactions between Deltex and the intracellular domain of Notch, as well as homotypic interaction among Deltex molecules were defined. The function of the Deltex-Notch interaction domains was examined by in vivo expression studies. Taken together, data from over-expression of Deltex fragments and from studies of physical interactions between Deltex and Notch demonstrate that Deltex positively regulates the Notch pathway through interactions with the Notch ankyrin repeats.

Experiments involving cell cultures indicate that the Deltex-Notch interaction prevents the cytoplasmic retention of Suppressor of Hairless protein, which is normally sequestered in the cytoplasm via association with the Notch ankyrin repeats and translocates to the nucleus when Notch binds to its ligand, Delta. On the basis of these findings Deltex appears to regulate Notch activity by antagonizing the interaction between Notch and Suppressor of Hairless. The translocation of the normally cytoplasmic Suppressor of Hairless protein to the nucleus when Notch binds to a ligand (Fortini and Artavanis-Tsakonas, 1994, Cell 79:273-282) is a convenient assay to monitor for Notch function as well as for the ability of Notch agonists of the present invention to activate Notch function.

Suppressor of Hairless has been shown to be a DNA binding protein. Genetic and molecular data indicate that the activity of Suppressor of Hairless can be influenced by its binding to the nuclear protein Hairless. Moreover it appears that the transcription of at least some of the bHLH genes of the Enhancer of split complex depends directly on Notch signaling and the ability of Suppressor of Hairless to recognize the appropriate binding sites upstream of these genes. Manipulation of these various interactions (e.g., disrupting the interaction between Notch and Suppressor of Hairless with an antibody directed against the ankyrin repeats) will result in modulating the activity of the Notch pathway.

Finally, the Notch pathway can be manipulated by the binding of Notch ligands (e.g., Delta, Serrate) to the extracellular portion of the Notch receptor. Notch signaling appears to be triggered by the physical interaction between the extracellular domains of Notch and its membrane-bound ligands on adjacent cells. The expression of full length ligands on one cell triggers the activation of the pathway in the neighboring cell which expresses the Notch receptor. Not surprisingly, the ligands act as agonists of the pathway. On the other hand, the expression of truncated Delta or Serrate molecules which lack intracellular domains expressed in neighboring cells results in non-autonomous, dominant negative phenotypes. This demonstrates that these mutant forms of the receptor act as antagonists of the pathway.

The definition of the various molecular interactions among the Notch pathway elements provides additional specific pharmacological targets and assays which can be used to screen for Notch function agonists and antagonists. Having evaluated the consequences of a particular molecular manipulation in vivo, this information can be used to design biochemical in vitro screening assays for biological or pharmaceuticals that interfere or enhance Notch function.

Screening for molecules that will trigger the dissociation of the Notch ankyrin repeats with Suppressor of Hairless and the subsequent translocation of Suppressor of Hairless from the cytoplasm to the nucleus results in the identification of agonists. The activation of transcription of a reporter gene which has been engineered to carry several Suppressor of Hairless binding sites at its 5' end in a cell that expresses Notch also results in the identification of agonists of the pathway.

Reversing the underlying logic of these assays leads to the identification of antagonists. For example, cell lines expressing the aforementioned reporter gene can be treated with chemicals and biologicals and those which have the capacity to stop the expression of the reporter gene can be identified.

In another specific embodiment, the Notch pathway function agonists include reagents that promote or activate cellular processes that mediate the maturation or processing steps required for the activation of Notch or a member of the Notch signaling pathway, such as the furin-like convertase required for Notch processing, Kuzbanian, the metalloprotease required for the cleavage and activation of the Notch ligand Delta, or, more generally, cellular trafficking and processing proteins such as the rab family of GTPases required for movement between cellular compartments (for a review on Rab GTPases, see Olkkonen and Stenmark, 1997, Int. Rev. Cytol. 176:1-85). The agonist can be any molecule that increases the activity of one of the above processes, such as a nucleic acid encoding a furin, Kuzabanian or rab protein, or a fragment or derivative or dominant active mutant thereof, or a peptidomimetic or peptide analog or organic molecule that binds to and activates the function of the above proteins. The peptidomimetic or peptide analog or organic molecule can be identified by the assays described above.

5.4. Antagonists of Notch Pathway Function

In certain embodiments, the present invention is directed to antagonizing Notch pathway function or antagonizing Notch function concurrently with altering cell fate control gene pathway function in a precursor cell under conditions that result in changing the fate of a cell. In other embodiments, antagonists are used to inhibit the Notch pathway such that cells, which are maintained in one differentiation state by Notch pathway activity, can be allowed to change their differentiation state, e.g., de-differentiate and re-enter mitosis and proliferate in response to the cues for altering cell fates according to the methods of the invention. An antagonist of Notch function is an agent that reduces or inhibits Notch function. Notch function inhibition is preferably carried out by contacting a terminally differentiated and/or post-mitotic cell and/or other mature cell that expresses Notch with a Notch antagonist.

Notch expression is generally associated with non-terminally differentiated cells. One exception to this general rule is that Notch is expressed in differentiated cervical columnar epithelial cells (Zagouras, 1995, Proc. Natl. Acad. Sci. USA 92:6414-6418). Another exception is that Notch is expressed in post-mitotic neurons of rat and human adult retina (Ahmad et al., 1995, Mech. Develop. 53:73-85). Immunocytochemical staining data indicates that the Notch polypeptides recognized by the antibodies are nuclear. The expression of engineered Notch fragments that are localized in the nucleus has been documented (reviewed in Artavanis-Tsakonas et al., 1995, Science 268:225-232), and these fragments were shown to be associated with activated mutant phenotypes. The presence of an activated form of Notch in the nucleus may lock these cells into a particular state of differentiation by restricting or completely blocking their capacity to respond to differentiation and/or proliferation stimuli. Therefore, it is conceivable that these post-mitotic neurons maintain their differentiated state by virtue of an activated Notch-1 form that is independent of Notch ligands. This state may perhaps afford such cell populations a certain plasticity. For example, an eventual cessation of nuclear Notch-1 activity might allow these cells to re-enter a mitotic state and/or respond to specific differentiation signals. In this context, it is interesting to note that retinal neurons in lower vertebrates such as Goldfish and *Xenopus* have regenerative capacity. Chemical ablation of specific neurons, such as degeneration of dopaminergic amacrine cells by 6-OH dopamine result in their replacement by regeneration (Reh and Tully, 1986, Dev. Biol. 114(2):463-469). However, such plasticity for regenerative purposes have not been observed in higher vertebrates. The observed Notch-1 activity in mature retinal neurons in the rat may represent the recapitulation of the functional significance of Notch-1 in retinal regeneration in lower vertebrates. Thus, antagonizing Notch function would confer responsiveness on mature mammalian cells that express Notch (or a fragment or derivative thereof capable of being immunospecifically bound by an anti-Notch antibody), e.g., mammalian neurons (e.g., of the central nervous system), thus facilitating their re-differentiation in response to differentiation cues provided by the methods of the invention. Such a method comprises contacting the mammalian cell with an antagonist of Notch function and exposing the cell to cell growth conditions prior to contacting the cell with a Notch and cell fate control gene pathway agonists.

Notch function antagonists include, but are not limited to, antisense nucleic acids which will prevent the expression of at least one of the proteins in the Notch signaling pathway by blocking either transcription or translation of one of the proteins in the Notch signaling pathway. Members of the Notch signaling pathway include Notch, Delta, Serrate, Deltex, Enhancer of Split, Presenilin as well as other members of the Delta/Serrate family which may be identified by virtue of sequence homology or genetic interaction, and in general, members of the Notch signaling pathway which are identified by molecular interactions (e.g., binding in vitro) or genetic interactions (as detected phenotypically, e.g., in *Drosophila*). For a general review of the Notch signaling pathway, see Artavanis-Tsakonas et al., 1995, Science 268:225-232 and Artavanis-Tsakonas et al., 1999, Science 284:770-776.

The antisense nucleic acids are of at least six nucleotides and are preferably oligonucleotides (ranging from 6 to about 50 oligonucleotides). In specific aspects, the oligonucleotide is at least 10 nucleotides, at least 15 nucleotides, at least 100 nucleotides, or at least 200 nucleotides. The oligonucleotides can be DNA or RNA or chimeric mixtures or derivatives or modified versions thereof, single-stranded or double-stranded. The oligonucleotide can be modified at the base moiety, sugar moiety, or phosphate backbone. The oligonucleotide may include other appending groups such as peptides, or agents facilitating transport across the cell membrane (see, e.g., Letsinger et al., 1989, Proc. Natl. Acad. Sci. U.S.A. 86:6553-6556; Lemaitre et al., 1987, Proc. Natl. Acad. Sci. 84:648-652; PCT Publication No. WO 88/09810, published Dec. 15, 1988) or blood-brain barrier (see, e.g., PCT Publication No. WO 89/10134, published Apr. 25, 1988), hybridization-triggered cleavage agents (see, e.g., Krol et al., 1988, BioTechniques 6:958-976) or intercalating agents (see, e.g., Zon, 1988, Pharm. Res. 5:539-549).

In a preferred aspect of the invention, a Notch antisense oligonucleotide is provided, preferably of single-stranded DNA. In a most preferred aspect, such an oligonucleotide comprises a sequence antisense to the sequence encoding ELR 11 and ELR 12 of Notch, most preferably, of human Notch. The oligonucleotide may be modified at any position on its structure with substituents generally known in the art.

The antisense oligonucleotide may comprise at least one modified base moiety which is selected from the group including but not limited to 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine.

The antisense oligonucleotide can also comprise at least one modified sugar moiety selected from the group including but not limited to arabinose, 2-fluoroarabinose, xylulose, and hexose.

The antisense oligonucleotide can also comprise at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

The antisense oligonucleotide can also be an α-anomeric oligonucleotide. An α-anomeric oligonucleotide forms specific double-stranded hybrids with complementary RNA in which, contrary to the usual β-units, the strands run parallel to each other (Gautier et al., 1987, Nucl. Acids Res. 15:6625-6641).

The oligonucleotide may be conjugated to another molecule, e.g., a peptide, hybridization triggered cross-linking agent, transport agent, hybridization-triggered cleavage agent, etc.

Such oligonucleotides may be synthesized by standard methods known in the art, e.g. by use of an automated DNA synthesizer (such as are commercially available from Biosearch, Applied Biosystems, etc.). As examples, phosphorothioate oligos may be synthesized by the method of Stein et al. (1988, Nucl. Acids Res. 16:3209), methylphosphonate oligos can be prepared by use of controlled pore glass polymer supports (Sarin et al., 1988, Proc. Natl. Acad. Sci. U.S.A. 85:7448-7451), etc.

In a specific embodiment, a Notch antisense oligonucleotide comprises catalytic RNA, or a ribozyme (see, e.g., PCT International Publication WO 90/11364, published Oct. 4, 1990; Sarver et al., 1990, Science 247:1222-1225). In another embodiment, the oligonucleotide is a 2'-0-methylribonucleotide (Inoue et al., 1987, Nucl. Acids Res. 15:6131-6148), or a chimeric RNA-DNA analogue (Inoue et al., 1987, FEBS Lett. 215:327-330).

In a specific embodiment, a Notch antisense nucleic acid comprises a double stranded RNA, utilizing a method called RNA interference (or RNA-i), in which injection of a few copies of a double stranded RNA molecules in a cell interferes with the function of an endogenous gene. This technique has been used successfully in *C. elegans* (Fire et al., 1998, Nature 391:806-811) and *Drosophila* (Kennerdell and Carthew, 1998, Cell 95:1017-1026; Misquitta and Paterson, 1999, Proc. Natl. Acad. Sci. USA 96:1451-1456), and may be potentially applied to other organisms or cell types.

In an alternative embodiment, antisense nucleic acids are produced intracellularly by transcription from an exogenous sequence. For example, a vector can be introduced in vivo such that it is taken up by a cell, within which cell the vector or a portion thereof is transcribed, producing an antisense nucleic acid (RNA) of the invention. Such a vector would contain a sequence encoding the antisense nucleic acid. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequence encoding the antisense RNA can be by any promoter known in the art to act in mammalian, preferably human, cells. Such promoters can be inducible or constitutive. Such promoters include but are not limited to: the SV40 early promoter region (Bernoist and Chambon, 1981, Nature 290:304-310), the promoter contained in the 3' long terminal repeat of Rous sarcoma virus (Yamamoto et al., 1980, Cell 22:787-797), the herpes thymidine kinase promoter (Wagner et al., 1981, Proc. Natl. Acad. Sci. U.S.A. 78:1441-1445), the regulatory sequences of the metallothionein gene (Brinster et al., 1982, Nature 296:39-42), a heat shock enhancer element in the context of a basal promoter such as the heat shock protein 70 gene promoter (Bienz et al., 1986, Cell. 45:753-60), etc.

The antisense nucleic acids of the invention comprise a sequence complementary and hybridizable to at least a sequence-specific portion of an RNA transcript of a Notch signaling pathway gene, preferably a human Notch signaling pathway gene. However, absolute complementarity, although preferred, is not required. A sequence "complementary to at least a portion of an RNA," as referred to herein, means a sequence having sufficient complementarity to be able to hybridize with the RNA, forming a stable duplex; in the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with a specific RNA it may contain and still form a stable duplex (or triplex, as the case may be). One skilled in the art can ascertain a tolerable degree of mismatch by use of standard procedures to determine the melting point of the hybridized complex.

Other Notch function antagonists include, but are not limited to, antibodies which inhibit interactions between Notch pathway protein constituents, thus disrupting Notch function, e.g., antibodies to the extracellular region of Notch, Delta, or Serrate that mediate binding to Delta, Notch and Notch, respectively (e.g., EGF-like repeat 11 and 12 of Notch). Such antibodies can be polyclonal, monoclonal, chimeric, single chain, Fab fragments, or from an Fab expression library.

Various procedures known in the art may be used for the production of polyclonal antibodies to a Notch signaling pathway protein or peptide. For the production of polyclonal antibody, various host animals can be immunized by injection with the native protein, or a synthetic version, or fragment thereof, including but not limited to rabbits, mice, rats, etc. Various adjuvants may be used to increase the immunological response, depending on the host species, and including but not limited to Freund's (complete and incomplete), mineral gels such as aluminum hydroxide, surface active substances such as lysolecithin, pluronic polyols, polyanions, peptides, oil emulsions, keyhold limpet hemocyanins, dinitrophenol, and potentially useful human adjuvants such as BCG (bacille Calmette-Guerin) and *corynebacterium parvum*.

For preparation of monoclonal antibodies, any technique which provides for the production of antibody molecules by continuous cell lines in culture may be used. For example, the hybridoma technique originally developed by Kohler and Milstein (1975, Nature 256, 495-497), as well as the trioma technique, the human B-cell hybridoma technique (Kozbor et al., 1983, Immunology Today 4, 72), and the EBV-hybridoma technique to produce human monoclonal antibodies (Cole et al., 1985, in Monoclonal Antibodies and Cancer Therapy, Alan R. Liss, Inc., pp. 77-96).

Antibody fragments which contain the idiotype (binding domain) of the molecule can be generated by known techniques. For example, such fragments include but are not limited to: the F(ab')$_2$ fragment which can be produced by pepsin digestion of the antibody molecule; the Fab' fragments which can be generated by reducing the disulfide bridges of the F(ab')$_2$ fragment, and the Fab fragments which can be generated by treating the antibody molecule with papain and a reducing agent.

In the production of antibodies, screening for the desired antibody can be accomplished by techniques known in the art, e.g. ELISA (enzyme-linked immunosorbent assay). For example, to select antibodies which recognize the intracellular domain of a Notch protein, one may assay generated hybridomas for a product which binds to a protein fragment containing such domain.

In a specific embodiment, the antagonist is a Notch, Delta or Serrate fragment that substantially contains the extracellular domain and optionally the transmembrane domain but lacks a portion or all of the intracellular domain of Notch, Delta or Serrate, respectively (dominant negative fragments) (see e.g., Sun and Artavanis-Tsakonas, 1996, Development 122:2465-2474).

In another specific embodiment, the antagonist of Notch pathway function is Deltex, most preferably a vertebrate Deltex molecule.

In another specific embodiment, the antagonist of Notch pathway function is Hairless.

In another specific embodiment, the antagonist of Notch function is fringe (Irvine and Wieschaus, 1994, Cell 79:595-606) or a functional fragment or derivative thereof that antagonizes Notch function.

In another specific embodiment, the Notch function antagonist is a cell that expresses a protein or fragment or derivative thereof which antagonizes Notch function. The cell expresses the Notch function antagonist in such a manner that it is made available to the mature cells, e.g., secreted, expressed on the cell surface, etc. In yet another specific embodiment, the Notch function antagonist is a nucleic acid that encodes a protein or fragment or derivative thereof which antagonizes Notch function; such an antagonist can, for example be employed or delivered according to the methods described in Section 5.6, infra.

In another specific embodiment, the antagonist of Notch pathway function is a peptidomimetic or peptide analog or organic molecule that binds to a member of the Notch signaling pathway. Such an antagonist can be identified by binding assays selected from among those known in the art.

In another specific embodiment, the Notch pathway function antagonists include reagents that inhibit cellular processes that mediate the maturation or processing steps required for the activation of Notch or a member of the Notch signaling pathway, such as the furin-like convertase required for Notch processing, Kuzbanian, the metalloprotease required for the cleavage and activation of the Notch ligand Delta, or, more generally, cellular trafficking and processing proteins such as the rab family of GTPases required for movement between cellular compartments (for a review on Rab GTPases, see Olkkonen and Stenmark, 1997, Int. Rev. Cytol. 176:1-85). The antagonistic reagents may include any molecule that prevents the expression or function of the above proteins, such as peptidomimetic or organic inhibitors or antisense nucleic acids or antibodies thereto, or nucleic acids encoding dominant negative mutants thereof. The peptidomimetic or organic inhibitor can be identified by the assays described above.

5.5. Cell Fate Control Genes and Proteins

Cells respond to external signals or changes in their environment in one of three possible ways, namely differentiation, proliferation or programmed cell death (apoptosis). The particular fate a cell opts for is determined by the nature of the signals it receives and the mediators of the response to the signal that are present in the cell. Genes that are necessary or sufficient to determine a cell's fate, be it differentiation, proliferation, or apoptosis, are herein called cell fate control genes, and the proteins they encode cell fate control proteins.

Cell fate control genes to be utilized using the methods of this invention include but are not limited to Pax genes (including but not limited to human or mouse PAX-1, PAX-2, PAX-3, PAX-4, PAX-5, PAX-6, PAX-7, PAX-8 or PAX-9; *Drosophila* eyeless and twin of eyeless), HOX genes (including but not limited to mammalian HOX A1-7, 9-11 or 13; HOX B1-9; HOX C4-6 or 8-13; HOX D1, 3-4 or 8-13; *Drosophila* lab, pb, Dfd, Scr, Antp, Ubx, abd-A or Abd-B), DLX genes (including but not limited to human DLX-2, DLX-4, DLX-5; mouse DLX-1, DLX-2, DLX-3, DLX-5, DLX-6; DLX-7; *Drosophila* Distal-less), Vestigial genes (*Drosophila* vestigial and homologs thereof), PBC genes (including but not limited to human or mouse Pbx1, Pbx2 or Pbx3 and *Drosophila* extradenticle), MEINOX genes (including but not limited to MEIS genes, e.g. human and mouse Meis1, Meis2, Meis3 and *Drosophila* homothorax and KNOX genes e.g. mouse KNOX1 and Prep1), bHLH genes (including mammalian MyoD, myogenin, myf-5, MASH-1 and MASH-2 and *Drosophila* achaete-scute complex genes), LIM homeobox genes (including but not limited to human ISLET-1, LIM-1, LMX1B, LHX2; mouse Islet-1, Lim-1, Lhx4, Lhx5, Lhx6, Lhx7 and Lhx8 and *Drosophila* apterous and lim3), MSX genes (including but not limited to human MSX-1, or MSX-2, mouse Msx-3 or *Drosophila* msh), POU genes (including but not limited to human Oct-1, Oct-2, Oct-6 and Pit-1; mouse Oct-1, Oct-4, Oct-6 and Pit-1; *Drosophila* pdm-1 and pdm-2), PTX genes (including but not limited to human Ptx1, Ptx2), NKX genes (including but not limited to human NKX2.5, NKX2.8, NKX3.1; mouse Nkx-1.1, Nkx-2.2, Nkx-2.5, Nkx-3.1, Nkx-3.2, Nkx-5.1), MADS box genes (including but not limited to human SRF and mef2 and *Drosophila* d-mef2 and d-SRF), SOX genes (including but not limited to human SOX-2, SOX-4, SOX-8, SOX-9, SOX-10, SOX-11, SOX-14 and SOX-17 and mouse Sox-2, Sox-3, Sox-4, Sox 13, Sox-15 and Sox-17), T-box genes (including but not limited to human TBX-5, TBX-6, TBX-10, TBX-18 and TBX-19; mouse Brachyury, Tbx-1, Tbx-2, Tbx-3, Tbx-4, Tbx-5, Tbx-6; *Drosophila* optomotor blind (omb)), WNT genes (including but not limited to human WNT-1, WNT-2, WNT-3A, WNT4, WNT-5A, WNT-7a, WNT-7B, WNT-8A, WNT-10B, WNT-13, WNT-14; mouse int-1, int-2, Wnt-1, Wnt-2b, Wnt-3a, Wnt-4, Wnt-5a, Wnt-5b, Wnt-6, Wnt-7a, Wnt-7b, Wnt-11, Wnt-10a, Wnt-15; *Drosophila* wingless, dwnt2, dwnt3, dwnt4, dwnt5), BMP/TGF-β superfamily genes (including but not limited to human TGFβ-1, TGFβ-2, TGFβ-3, BMP-1, BMP-2, BMP-3B (GDF10), BMP-4, BMP-5, BMP-6, BMP-7, BMP-8, activin, GDF1, GDF5, GDF8, GDF9; mouse TGFβ-1, TGFβ-3, BMP-1, BMP-2, BMP-3B (GDF10), BMP-4, BMP-5, BMP-6, BMP-7, BMP-8A, BMP-8B, GDF1, GDF5, GDF6, GDF7, GDF9b, GDF11; *Drosophila* decapentaplegic (dpp), 60A, tolloid (tld)) and hedgehog genes (including but not limited to human or mouse Sonic, Indian or Desert hedgehog; *Drosophila* hedgehog).

In all embodiments of the present invention, the cell fate control gene is not Notch, or a member of the Notch signal transduction pathway as classically known, e.g., Notch, Delta, Serrate, Deltex, or Suppressor of Hairless.

In a preferred embodiment, the cell fate control gene or protein is selected from the group comprising Pax-5 or Pax-6.

In a preferred embodiment, the cell fate control gene or protein is mammalian, most preferably human.

In an embodiment of the present invention, the a Manipulated cell is of a cell type with which the cell fate control gene pathway agonized to produce the Manipulated cell is naturally associated. By way of example and not limitation, and by the methods of the present invention, Pax6 activity is altered to produce ocular cells, HoxB8 activity altered to produce monocytes, LIM homeodomain activity altered to produce motor neurons, PTX activity altered to produce pituitary tissue, NKX2-5 activity altered to produce cardiac muscle, MEF-2 activity altered to produce skeletal muscle, Tbx-6 activity altered to produce somitic tissue, and so on and so forth.

5.5.1. Assays for the Identification of Cell Fate Control Genes

In general, cell fate control genes can be identified by their abilities to alter cell fates when agonized, either alone or in combination with agonizing or antagonizing Notch pathway function. In one mode of the invention, a cell fate control gene may be identified by assays in *Drosophila* as described in Section 6, infra. In one assay, a putative cell fate control gene is identified by its ability to alter eye development when misexpressed under UAS control in the developing eye imaginal disc using the ey-Gal4 driver. Many (but not necessarily all) cell fate control genes will result in abnormal eyes in the adult, for example a change in the tissue type (i.e., re-differentiation), an enlargement of the eye (i.e., proliferation), or a reduction of the eye (i.e., programmed cell death). Alternatively, a putative cell fate control gene is identified by generating a loss of function, preferably null, mutation in the gene, and determining whether the mutation results in abnormal cell fate determination.

5.6. Agonists of Cell Fate Control Gene Pathway Function

As used herein, an agonist of cell fate control gene pathway function is an agent that promotes, i.e., causes or increases, activation of cell fate control gene pathway function. As used herein, "cell fate control gene pathway function" shall mean a function mediated by the cell fate control gene pathway.

Activated cell fate control gene or cell fate control gene pathway component derivatives can be made by altering cell fate control protein or cell fate control gene pathway component encoding sequences by substitutions, additions or deletions that provide for functionally equivalent molecules. These derivatives and analogs can be produced by various methods known in the art. The manipulations which result in their production can occur at the gene or protein level. The cloned cell fate control gene or cell fate control gene pathway component sequence can be modified by any of numerous strategies known in the art (Maniatis, T., 1990, Molecular Cloning, A Laboratory Manual, 2d ed., Cold Spring Harbor Laboratory, Cold Spring Harbor, N.Y.). The sequence can be cleaved at appropriate sites with restriction endonuclease(s), followed by further enzymatic modification if desired, isolated, and ligated in vitro. In the production of the gene encoding a derivative or analog of a cell fate control gene or cell fate control gene pathway component, care should be taken to ensure that the modified gene remains within the same translational reading frame as the original gene, uninterrupted by translational stop signals.

Additionally, the cell fate control gene or cell fate control gene pathway component nucleic acid sequence can be mutated in vitro or in vivo, to create and/or destroy translation, initiation, and/or termination sequences, or to create variations in coding regions and/or form new restriction endonuclease sites or destroy preexisting ones, to facilitate further in vitro modification. Any technique for mutagenesis known in the art can be used, including but not limited to, in vitro site-directed mutagenesis (Hutchinson et al., 1978, J. Biol. Chem 253:6551), etc. PCR primers containing sequence changes can be used in PCR to introduce such changes into the amplified fragments.

When the cell fate control gene encodes a transcription factor, activation of the cell fate control gene pathway is preferably achieved by introducing into the cell a recombinant nucleic acid expressing the cell fate control protein, or by contacting the cell with recombinantly expressed cell fate control protein functionally coupled to an internalization signal peptide. If the cell fate control gene is a signaling molecule, the cell fate control gene pathway is activated by contacting the cell with recombinantly expressed signaling molecule, or by contacting the cell with a recombinant nucleic acid expressing an activated form of a pathway component, e.g. a constitutively activated receptor or signal transducing DNA binding protein.

Where a cell fate control gene encodes a transcription factor, usually the transcription factor is a constitutively nuclear protein that binds to DNA and regulates gene transcription. However, the activity of transcription factors is often regulated, e.g. by restricting their ability to access the nucleus or their ability to bind DNA. If the cell fate control gene is constitutively nuclear, activating the cell fate control gene pathway is preferably achieved by introducing into the cell a recombinant nucleic acid expressing the cell fate control gene under the control of a suitable promoter. Alternatively, the cell fate control gene product can be recombinantly expressed whereby it is functionally coupled to an internalization signal peptide that would allow its uptake from the culture medium into the cell nucleus. In this instance, activation of the cell fate control gene pathway is achieved by placing in the culture medium the in vitro expressed protein coupled to the internalization sequence. In a specific embodiment, the internalization signal is that of Antennapedia (reviewed by Prochiantz, 1996, Curr. Opin. Neurobiol. 6:629-634, Hox A5 (Chatelin et al., 1996, Mech. Dev. 55:111-117), HIV TAT protein (Vives et al., 1997, J. Biol. Chem. 272: 16010-16017) or VP22 (Phelan et al., 1998, Nat. Biotechnol. 16:440-443).

If the cell fate control gene product is normally regulated in a manner that would preclude it from accessing the nucleus, the cell fate control gene pathway is preferentially activated by introducing into the precursor cell a nucleic acid encoding an active form of the protein. For example, a truncated form of the protein is preferable if nuclear entry requires the removal of an inhibitory domain. In another embodiment, a protein carrying point mutations that mimic phosphorylation (e.g. serine/threonine/tyrosine to glutamic acid) is provided if nuclear access requires phosphorylation or point mutations that prevent phosphorylation of de-phosphorylation is required to permit nuclear localization. Alternatively, the cell fate control gene pathway is activated by introducing into the cell a nucleic acid encoding the wild type protein then treating the cell with a reagent that results in the activation of the cell fate control gene pathway. Activation of the cell fate control gene pathway can also be achieved by placing in the culture medium the in vitro expressed active form of the protein functionally coupled to an internalization sequence or by placing in the culture medium the in vitro expressed wild type protein functionally coupled to an internalization sequence then treating the cell with a reagent that induces the activation of the cell fate control gene pathway.

If the protein encoded by the cell fate control gene is modulated in a manner that prevents DNA binding or transcriptional activation, then a suitably active form is provided. If modulation is mediated by phosphorylation or de-phosphorylation, a mutant form of the cell fate control gene is provided such that it functions as if constitutively phosphorylated or de-phosphorylated (e.g. by changing the coding region so that the residues required to be phosphorylated for activity are mutated into acidic residues such as aspartic acid, or so that the residue required to be de-phosphorylated for activity are mutated into residues that are unphosphorylatable, such as alanines). Alternatively, a construct carrying the wild type protein is transfected into the precursor cells and the precursor cells treated with an agent that would activate the wild type protein.

Activation of the cell fate control gene pathway need not be direct. In one embodiment, activation is achieved by inhibiting or antagonizing the function of an inhibitor of said cell fate control gene pathway. In one exemplary embodiment, the method addresses a situation of posterior dominance. "Posterior dominance" is a phenomenon amongst the HOX genes, wherein one HOX gene prevents the activity of a more anterior HOX gene if both are expressed in the same cell. Activation of an anterior HOX gene in such a cell can simply consist of inhibiting the function of the more posterior gene. In another exemplary embodiment, a signaling pathway is activated indirectly. For example, the hedgehog (HH) pathway is a constitutively active pathway, the signal originating from the smoothened (SMO) cell surface seven-transmembrane protein and effective to repress protein kinase A (PKA) activity. The interaction between SMO and another transmembrane protein, patched (PTC), prevents the constitutively activated receptor from signaling and repressing the repressor of the pathway, PKA. When HH is present, it binds to PTC and allows SMO to relay its signal, which includes the repression of PKA. Thus, the HH pathway can be indirectly activated in one of two ways, namely inhibition of either PTC or PKA activity. In the exemplary embodiments above, inhibiting or antagonizing a posterior HOX gene, PKA or PTC can be achieved by standard molecular biology techniques, such as by use of antisense nucleic acids or antagonist antibodies or expression of a dominant negative mutant, described in Section 5.3.2, supra. It will be obvious to those skilled in the art that the specific embodiments described in this paragraph are merely exemplary. The principle of antagonizing an inhibitor can be applied to any cell fate control pathway of interest.

In a specific embodiment, activation of a Hox gene pathway in the presence of the expression of a more posterior Hox gene comprises the overexpression of said Hox gene pathway.

5.7. Antagonists of Cell Fate Control Gene Pathway Function

An antagonist of a cell fate control gene pathway function is an agent that reduces or inhibits cell fate control gene pathway function. Using the technologies described supra, it is possible to manipulate precursor cells in order to antagonize cell fate control gene pathway function.

In one embodiment, antagonizing cell fate control gene pathway function is mediated by antisense nucleic acids which will prevent the expression of the cell fate control gene or at least one component the cell fate control gene pathways. Antisense methods are described in Section 5.4, supra. In a preferred mode of the embodiment, the antisense nucleic acid is a DNA oligonucleotide ranging from 15 to 50 bases that is complementary and hybridizable to a sequence-specific portion of an RNA transcript encoding the cell fate control protein or a component of the cell fate control gene pathway. In another preferred mode of the embodiment, the antisense nucleic acid is produced by recombinant means, e.g. from a vector having a sequence that, when transcribed, produces an antisense RNA. In an alternative mode of the embodiment, the antisense nucleic acid is a double stranded RNA molecule ranging from 50 to 5,000 base pairs.

In another embodiment, the antagonist is an antibody which would inhibit the function of at least one cell fate control gene pathway component, for example by blocking the binding of a transcription factor to DNA or by blocking the interaction between two components of a signal transduction pathway.

In yet another embodiment, the cell fate gene pathway antagonist is a nucleic acid encoding a repressor of the pathway, or the repressor protein itself. The nucleic acid or protein can be prepared by the methods described in section 5.1, supra. In the case of a cell fate control protein that is a transcription factor, the repressor protein can be an inhibitory dimerization partner, a dominant negative form of the transcription factor (e.g. comprising the DNA binding domain but lacking the transcriptional activation domain), or a competitor for DNA binding. In the case of a cell fate control protein that is a signaling molecule, the repressor can be a dominant negative component of the pathway for example a truncated receptor containing only the extracellular domain, or a dominant active mutant form of a repressor of the pathway.

Like activation of the cell fate control gene pathway, inactivation of the pathway need not be direct. Referring back to the exemplary embodiments for indirect activation of a cell fate control gene pathway described in Section 5.6, when the cell fate control gene is a HOX gene, inactivation of the HOX gene pathway can be achieved by providing in the cell the activity of a more dominant, more posterior HOX gene pathway. In the case of the HH pathway, inhibition of the pathway can be achieved by providing a dominant active form of PKA, e.g. the catalytic domain in the absence of the regulatory domain.

5.8. Screening for Notch and Cell Fate Control Gene Pathway Agonists and Antagonists The invention provides a method for screening agonists or antagonists of Notch pathway function, comprising altering a cell fate control gene pathway function in a cell by a method comprising contacting the cell with an agonist or antagonist of the cell fate control gene pathway function and concurrently treating the cell with a test agonist or antagonist of Notch pathway function, then subjecting the cell to conditions that allow cell fate determination to occur; and examining the cell for an alteration in cell fate. In order to identify a test compound as an agonist or antagonist of Notch pathway function, the alteration in cell fate elicited by the test compound has to differ from the cell fate alteration elicited by the method in the absence of an alteration in cell fate control gene pathway function.

The invention further provides a method for screening agonists or antagonists of a cell fate control gene pathway function, comprising Notch pathway function in a cell by a method comprising contacting the cell with an agonist or antagonist of the Notch pathway function, treating the cell with a test agonist or antagonist of cell fate control gene pathway function while subjecting the cell to conditions that allow cell fate determination to occur, and examining the cell for an alteration in cell fate. In order to identify a test compound as an agonist or antagonist of the cell fate control gene pathway function, the alteration in cell fate elicited by the test compound has to differ from the cell fate alteration elicited by the method in the absence of an alteration in Notch pathway function.

An alteration in cell fate can be detected by methods known to those skilled in the art, for example changes in cell morphology for detecting differentiation, Bromodeoxyuridine (BrDU) or $^{35}$S-Methionine incorporation into DNA or cellular proteins, respectively, to measure a change in the rate of proliferation, or incorporation of acridine orange to measure apoptosis.

5.9. Obtaining and Culturing Precursor Cells

Cells in which cell fate is altered according to the present invention are herein called "precursor cells". Precursor cells can be primary cells or cell lines, or from any species, including but not limited to human, animal, plant, mammal, vertebrate, primate, mouse, rat, dog, cat, horse, cow, fowl, insect, *Drosophila*, and *C. elegans*.

Precursor cells can be any cells of any differentiation state. If necessary, terminally differentiated precursor cells are treated so that they respond to new cell fate cues, for example by initially inhibiting the activity of the Notch pathway in those terminally differentiated cells that express Notch. If the precursor cell is not terminally differentiated, the precursor cell population can be expanded prior to altering its fate, e.g. by activating the Notch pathway in the cells; alternatively, the precursor cell population can be expanded after transformation, e.g. by maintaining the activity of the Notch pathway in the cells after the cessation of cell fate control pathway activity and culturing the cells under growth conditions. Further, the precursor cells can be isolated from a cell population, if desired, before or after Notch and cell fate pathway activation. Activation of Notch pathway is preferably achieved by contacting the cell with a Notch ligand, e.g., in soluble form or recombinantly expressed on a cell surface or immobilized on a solid surface, or by introducing into the cell a recombinant nucleic acid expressing a dominant active Notch mutant or an activating Notch ligand, or other molecule that activates the Notch pathway.

In one embodiment, precursor cells can be manipulated in vivo by directly contacting the cells with proteins and nucleic acids that serve to alter the activity of the Notch pathway and optionally a cell fate control gene pathway. In another embodiment, the precursor cells are manipulated in vitro. For in vitro manipulation of cells according to the methods of the invention, precursor cells obtained and cultured by any method known in the art, e.g. directly from tissues of an individual or from cell lines. The following exemplary embodiments describe approaches which allow for the isolation of precursor cells and precursor cell-containing tissues, which are to be treated with agonists of the Notch and cell fate control gene pathways according to the present invention. As already alluded to, isolated cell types or even mixtures of cell populations can be treated according to the method of the invention. The isolated precursor cell or precursor cell population can be cultured ex vivo for expansion under the influence of the Notch function agonists and cell growth conditions prior to or after changing their fate by altering Notch and one or more cell fate control gene pathway function. If the Manipulated cell population is to be used for transplantation, a recombinant gene can be introduced into the cell so that it or its progeny expresses a desired gene product before transplantation. Introduction of a recombinant gene can be accomplished either before or after precursor cell manipulation.

In a preferred embodiment, the precursor cell populations are purified or at least highly enriched. However, in order to manipulate the fate of a precursor cells by the methods of the present invention it is not necessary that the precursor cells are a pure population. Once a mixture is treated, the desired population can be selected for and purified. Furthermore, purification may not be necessary or desirable prior to therapeutic administration in vivo.

In one embodiment, the precursor cell in which Notch pathway function has been activated in order to expand the precursor cell prior or subsequent to manipulating the cell's fate, the cell is subjected to cell growth conditions to induce proliferation. Such cell growth conditions (e.g., cell culture medium, temperature, if growth is done in vitro) can be any of those commonly known in the art. In a preferred embodiment, both Notch activation and exposure to cell growth conditions are carried out in vitro.

The isolation of precursor cells for use in the present invention can be carried out by any of numerous methods commonly known to those skilled in the art. For example, one common method for isolating precursor cells is to collect a population of cells from a patient and using differential antibody binding, wherein cells of one or more certain differentiation stages are bound by antibodies to differentiation antigens, fluorescence activated cell sorting is used to separate the desired precursor cells expressing selected differentiation antigens from the population of isolated cells. The following section describes exemplary methods for the isolation of various types of cells. In addition, any method known in the art can be employed.

In a preferred embodiment, the precursor cell is a stem cell.

5.9.1. Mesenchymal Cells

5.9.1.1 Stem Cells

One of the most important type of progenitor cells vis a vis for therapeutic applications are those derived from the mesenchyme. Mesenchymal progenitors give rise to a very large number of distinct tissues (Caplan, 1991, J. Orth. Res 641-650). Most work to date involves the isolation and culture of cells which can differentiate into chondrocytes and osteoblasts. The systems developed to isolate the relevant progenitor cell populations were worked out first in chick embryos (Caplan, 1970, Exp. Cell. Res. 62:341-355; Caplan, 1981, 39th Annual Symposium of the Society for Developmental Biology, pp. 37-68; Caplan et al., 1980, Dilatation of the Uterine Cervix 79-98; DeLuca et al., 1977, J. Biol. Chem. 252:6600-6608; Osdoby et al., 1979, Dev. Biol. 73:84-102; Syftestad et al., 1985, Dev. Biol. 110:275-283). Conditions were defined under which chick mesenchymal cells differentiated into chondrocytes and bone. Id. With regard to cartilage and bone, the properties of mouse or human mesenchymal limb appear to be quite similar if not identical (Caplan, 1991, J. Orth. Res. 641-650). Mesenchymal cells capable of differentiating into bone and cartilage have also been isolated from marrow (Caplan, 1991, J. Orth. Res. 641-650).

Caplan et al., 1993, and Caplan et al., 1996, U.S. Pat. Nos. 5,226,914 and 5,486,359 respectively, describe exemplary methods for isolating mesenchymal stem cells from bone marrow. These isolated marrow stem cells can be used in conjunction with Notch reagents to expand the stem cell population. These precursor cells, optionally expanded with Notch or other reagents, may then be further differentiated by the methods of the present application as described supra. The cells are preferably differentiated into osteocytes, cartilage, chondrocytes, adipocytes, etc.

Several bone marrow isolation protocols have been reported and can be used to obtain progenitor or precursor cells. Single cell suspensions from rat bone marrow can be prepared according to Goshima et al., 1991, Clin. Orth. and Rel. Res. 262:298-311. Human stem cell cultures from marrow can be prepared as described by Bab et al., 1988, Bone Mineral 4:373-386 as follows: Whole marrow cells are obtained from five patients. The marrow samples are separated from either the iliac crest or femoral midshaft. Marrow samples, 3 ml in volume, are transferred to 6 ml of serum-free Minimal Essential Medium (MEM) containing 50 U/ml penicillin and 0.05 mg/ml streptomycin-sulfate. A suspension of predominantly single cells is prepared as described previously (Bab et al., 1984, Calcif. Tissue Int. 36:77-82; Ashton et al., 1984, Calcif. Tissue Int. 36:83-86) by drawing the preparation into a syringe and expelling it several times sequentially through 19, 21, 23 and 25 gauge needles. The cells are counted using a fixed volume hemocytometer and the concentration adjusted to $1-5\times10^8$ total marrow cells per ml suspension. Positive and negative control cell suspensions can be set as described before (Shteyer et al., 1986, Calcif. Tissue Int. 39:49-54), using rabbit whole marrow and spleen cells, respectively.

5.9.1.2 Connective Tissue

Connective tissue comprises fibroblasts, cartilage, bone, adipose and smooth muscle cells. Fibroblasts are the least differentiated of the connective tissue cells and are dispersed in connective tissues throughout the body. They can be identified by their characteristic secretion of type I and/or type III collagen. Fibroblasts can migrate into tissue wounds and secrete a collagenous matrix that heals and isolates the wounds. Further, they can differentiate into other members of the connective tissue family, depending on their local cues. The utility of fibroblasts lies not only in their plasticity, i.e. ability to differentiate into many cell types, but also the ease of growing the cells in culture and their rapid division. Fibroblasts can therefore be grown using basic tissue culture techniques well known to those skilled in the art and described in many readily available publications, e.g. Freshney, 1994, Culture of Animal Cells, third edition, Wiley-Liss Inc., New York. These characteristics make fibroblasts preferred precursor cells for practicing the methods of the invention.

5.9.1.3 Endothelium

Endothelial membrane isolation and separation from associated tissue is described by Schnitzer et al. in U.S. Pat. No. 5,610,008. Additionally, endothelial culture techniques have been described in scientific publications (e.g. Haudenschild et al., 1976, Exp. Cell Res. 98:175-183; Folkman and Haudenschild, 1980, Nature 288:551-556). In humans, endothelial cells have been successfully isolated from human umbilical veins (Jaffe et al., 1973) and human adipose (Kern et al., 1983, J. Clin. Invest. 71:1822-1829) and dermal (Davison et al., 1983, In Vitro 19:937-945) capillaries. Generally, they are released from the surrounding tissue by collagenase treatment and grown on a suitable substrate in the presence of growth factors (see Zetter, 1994, in Culture of Animal Cells, third edition, Wiley-Liss Inc., New York, p. 334).

5.9.2. Neuroectodermal Cells

5.9.2.1 Neural Stem Cells

It is generally assumed that neurogenesis in the central nervous system eases before or soon after birth. In recent years, several studies have presented evidence indicating that at least to some degree new neurons continue to be added to the brain of adult vertebrates (Alvarez-Buylla and Lois, 1995, Stem Cells (Dayt) 13:263-272). The precursors are generally located in the wall of the brain ventricles. It is thought that from these proliferative regions, neuronal precursors migrate towards target positions where the microenvironment induces them to differentiate. Studies have been reported where cells from the sub-ventricular zone can generate neurons both in vivo as well as in vitro, reviewed in Alvarez-Buylla and Lois, 1995, Stem Cells (Dayt) 13:263-272.

The neuronal precursors from the adult brain can be used as a source of cells for neuronal transplantation (Alvarez-Buylla, 1993, Proc. Natl. Acad. Sci. USA 90:2074-2077). Neural crest cells have also been long recognized to be pluripotent neuronal cells which can migrate and differentiate into different cell neuronal cell types according to the instructions they receive from the microenvironment they find themselves in (LeDouarin and Ziller, 1993, Curr. Opin. Cell Biol. 5:1036-1043).

Mature neurons and glia may be isolated by methods known to those skilled in the art.

5.9.2.2 Endocrine Cells

Endocrine cells of the thyroid, parathyroid and pancreas may be isolated and cultured by the methods described in U.S. Pat. Nos. 5,888,816 and 5,646,035 by Coon et al.

5.9.3. Fetal Cells

The fact that fetal brain tissue has been shown to have clear behavioral effects when transplanted into adult lesioned brains, has focused attention on human fetal tissue as a potential cell source in transplantation protocols designed to improve neurodegenerative disorders (Bjorklund, 1993, Nature 362:414-415; McKay, 1991, Trends Neurosci. 14:338-340). Nevertheless both ethical, as well as practical considerations make fetal tissue a difficult source to deal with. Expansion of neuronal stem cells whether fetal or otherwise using Notch function agonists provides an alternative source for obtaining the desired quantities of precursor cells for transplantation purposes. Fetal tissues or adult tissues containing precursors can be treated with Notch function agonists as described earlier in order to expand the undifferentiated progenitor cell populations. Fetal cells can placed into primary culture using, for example, protocols developed by Sabate et al., 1995, Nature Gen. 9:256-260, before being treated with Notch function agonists. By way of example but not limitation, the procedure is as follows: Primary cultures of human fetal brain cells can be isolated from human fetuses, obtained from legal abortions after 5 to 12 weeks of gestation. Expulsion can be done by syringe-driven gentle aspiration under echographic control. Fetuses collected in sterile hibernation medium are dissected in a sterile hood under a stereomicroscope. Brains are first removed in toto in hibernation medium containing penicillin G 500 U/ml, streptomycin 100 μg/ml, and fungizon 5 μg/ml. For fetuses of six to eight weeks of age the brain is separated into an anterior (telencephalic vesicles and diencephalon) and a posterior fraction (mesencephalon, pons and cerebellar enlage) and a posterior in toto after careful removal of meninges. For older fetuses, striatal hippocampal, cortical and cerebellar zones expected to contain proliferative precursor cells are visualized under the stereomicroscope and dissected separately. Cells are transferred to either Opti-MEM (Gibco BRL) containing 15% heat-inactivated fetal bovine serum (FBS) (Seromed), or to a defined serum-free medium (DS-FM) with human recombinant bFGF (10 ng/ml, Boehringer), which is a minor modification of the Bottenstein-Sato medium 39 with glucose, 6 g/l, glutamine 2 mM (Gibco BRL), insulin 25 ug/ml (Sigma) transferrin 100 μg/ml (Sigma), sodium selenite 30 nM (Gibco BRL), progesterone 20 nM (Sigma), putrescine 60 nM (Sigma), penicillin G (500 U/ml), streptomycin 100 μg/ml, and fungizon 5 μg/ml. Cells, approximately 40,000 per cm$^2$, are grown at 37° C. in an atmosphere containing 10% $CO_2$ in tissue culture dishes (Falcon or Nunc) coated with gelatin (0.25% wt/vol) followed by Matrigel (Gibco BRL, a basement membrane extract enriched in laminin and containing trace amounts of growth factors diluted one in 20). Cells in culture can be treated with Notch function agonists in order to expand the population of the appropriate cells until the desired cell mass is reached for transplantation.

5.9.4. Hematopoietic Cells

Any technique which provides for the isolation, propagation, and maintenance in vitro of hematopoietic stem cells (HSC) can be used in this embodiment of the invention. Techniques by which this can be accomplished include (a) the isolation and establishment of HSC cultures from bone marrow cells isolated from the future host, or a donor, or (b) the use of previously established long-term HSC cultures, which may be allogeneic or xenogeneic. Non-autologous HSC are used preferably in conjunction with a method of suppressing transplantation immune reactions of the future host/patient. In a particular embodiment of the present invention, human bone marrow cells can be obtained from the posterior iliac crest by needle aspiration (see, e.g., Kodo et al., 1984, J. Clin. Invest. 73:1377-1384). In a preferred embodiment of the present invention, the HSCs can be made highly enriched or in substantially pure form. This enrichment can be accomplished before, during, or after long-term culturing, and can be done by any techniques known in the art. Long-term cultures of bone marrow cells can be established and maintained by using, for example, modified Dexter cell culture techniques (Dexter et al., 1977, J. Cell Physiol. 91:335) or Witlock-Witte culture techniques (Witlock and Witte, 1982, Proc. Natl. Acad. Sci. USA 79:3608-3612).

Another technique for the isolation of HSC is described by Milner et al., 1994, Blood 83:2057-2062. Bone marrow samples are obtained and are separated by Ficoll-Hypaque density gradient centrifugation, are washed, and stained using two-color indirect immunofluorescent antibody binding and then separated by fluorescence-activated cell sorting (FACS). The cells are labelled simultaneously with IgG antibodies such that CD34$^+$ hematopoietic stem cells, including the immature subset that lacks expression of individual lineage associated antigens, CD34$^+$lin$^-$, are isolated from the cells collected from marrow.

Where hematopoietic progenitor cells are desired, the presence of hematopoietic progenitor cells and/or their progeny can be detected by commonly known in vitro colony forming assays (e.g., those that detect CFU-GM, BFU-E). As another example, assays for hematopoietic stem cells are also known in the art (e.g., spleen focus forming assays, assays that detect the ability to form progenitors after replating).

5.9.5. Epithelial Cells

5.9.5.1 Stem Cells and Keratinocytes

Epithelial stem cells (ESCs) and keratinocytes can be obtained from tissues such as the skin and the lining of the gut by known procedures (Rheinwald, 1980, Meth. Cell Bio. 21A:229). In stratified epithelial tissue such as the skin, renewal occurs by mitosis of precursor cells within the germinal layer, the layer closest to the basal lamina. Precursor cells within the lining of the gut provide for a rapid renewal rate of this tissue. ESCs obtained from the skin or lining of the gut of a patient or donor can be grown in tissue culture (Rheinwald, 1980, Meth. Cell Bio. 21A:229; Pittelkow and Scott, 1986, Mayo Clinic Proc. 61:771).

5.9.5.2 Salivary Epithelial Cells

Culture and growth conditions of non-transformed salivary epithelial cells are described in U.S. Pat. No. 5,462,870 by Chopra.

5.9.5.3 Liver Stem Cells

Liver stem cells can be isolated by methods described in PCT Publication WO 94/08598, dated Apr. 28, 1994.

5.9.5.4 Mature Liver Cells

A collagenase-liver-perfusion method has been described for the isolation of liver cells (hepatocytes) from both rats (Seglen et al., 1976, in Methods in Cell Biology, D. M. Prescott, Ed., Vol. XIII, pp. 29-83, Academic Press, New York) and humans (Butterworth et al., 1989, Cancer Res. 49:1075-84). Suitable culture conditions—including the use of lipid-bound glycosaminoglycan substrates—are taught in U.S. Pat. No. 5,624,839 by Yada et al.

5.9.5.5 Mammary Cells

In one specific embodiment, the epithelial cell population desired as a precursor to the present invention consists of mammary epithelial cells. These may be isolated according to the method of U.S. Pat. No. 4,423,145.

5.9.5.6 Cervical Cells

Cervical kertinocytes can be grown in culture using a variation of the method used for culturing epidermal keratinocytes (Stanley and Parkinson, 1979, Int. J. Cancer 24:407-414), the method comprising two steps, or primary and secondary culture. The primary culture comprises inoculating the disaggregated epithelium into a tissue culture flask or plate in the presence of serum, growth factors and irradiated or mitomycin C-fed Swiss 3T3 fibroblasts. Secondary cultures are grown on fibroblast support cells.

5.9.5.7 Kidney Stem Cells

Mammalian kidney emerges from the metanephric mesenchyme which induces the uteric bud to undergo a series of morphogenetic movements ultimately forming the mature urinary collecting system (Nigam and Brenner, 1992, Curr. Opin. Nephrol. Huper 1:187-191. The uteric bud, an epithelial outgrowth of the Wolfian duct, contracts and induces condensing adjacent mesenchyme along differentiation pathways of epithelial divergence in early embryonic life. Attempts to study this process in vitro have been reported; metanephros in organ culture can be induced to form tubules using embryonic spinal cord as the inducer. While the specific transducing agents that lead to the induction of metanephric mesenchyme by the uteric bud in vivo or by spinal cord in vitro are not known, cell specific markers show that the differentiation program is induced in progenitor cells (Karp et al., 1994, Dev. Biol. 91:5286-5290).

5.9.5.8 Mature Kidney Cells

The mature kidney consists of a variety of cell types. The isolation or separation of many of these has been described in scientific publications (e.g. Taub et al., 1989, In Vitro Cell Dev. Biol. 25:770-775; Wilson et al., 1985, Am. J. Physiol. 248:F436-F443; Smith and Garcia-Perez et al., 1985, Am. J. Physiol. 248:F1-F7; Pizzonia et al., 1991, In Vitro Cell Dev. Biol. 27A:409-416). Further, methods for culturing primary cultures of mature human kidney have been described (Detrisac et al., 1984, Kidney Int. 25:383-390; States et al., 1984, Biochem. Med. Metab. Biol. 36:151-161; McAteer et al., 1991, J. Tissue Cult. Methods 13:143-148). In one illustrative example, the primary features of culturing adult kidney cells with the characteristics of the proximal renal tubule are the following: progressive enzymatic digestion of an outer cortex tissue fragment; harvesting single cells for culture: growing the cells under high density on a feeder layer of plastic in the presence of serum (Kempson et al., 1989, J. Lab. Clin. Med. 113:285-296).

5.9.5.9 Epithelial Cells of the Lung

Homogeneous lung epithelial cell lines can be isolated and cultured according to the methods of U.S. Pat. No. 5,364,785.

The key to successful culturing of bronchial and tracheal cells is serum-free medium, which prevents terminal differentiation and selects against growth of fibroblasts (LaVeck and Lechner, 1994, in Culture of Animal Cells, third edition, Wiley-Liss Inc., New York, p. 325).

5.10. Gene Therapy

The cells produced by manipulation of the Notch and cell fate control gene pathways can be made recombinant and used in gene therapy. In its broadest sense, gene therapy refers to therapy performed by the administration of a nucleic acid to a subject. The nucleic acid, either directly or indirectly via its encoded protein, mediates a therapeutic effect in the subject. The present invention provides methods of gene therapy wherein a nucleic acid encoding a protein of therapeutic value (preferably to humans) is introduced into the precursor cells manipulated according to the methods of the invention, before or after manipulation and before or after expansion, if expansion is applied, such that the nucleic acid is expressible by the precursor cells and/or their Manipulated progeny, followed by administration of the recombinant cells to a subject.

The recombinant precursor cells of the present invention can be used in any of the methods for gene therapy available in the art. Thus, the nucleic acid introduced into the cells may encode any desired protein, e.g., a protein missing or dysfunctional in a disease or disorder. The descriptions below are meant to be illustrative of such methods. It will be readily understood by those of skill in the art that the methods illustrated represent only a sample of all available methods of gene therapy.

For general reviews of the methods of gene therapy, see Lundstrom, 1999, J. Recept. Signal Transduct. Res. 19:673-686; Robbins and Ghivizzani, 1998, Pharmacol. Ther. 80:35-47; Pelegrin et al., 1998, Hum. Gene Ther. 9:2165-2175; Harvey and Caskey, 1998, Curr. Opin. Chem. Biol. 2:512-518; Guntaka and Swamynathan, 1998, Indian J. Exp. Biol. 36:539-535; Desnick and Schuchman, 1998, Acta Paediatr. Jpn. 40:191-203; Vos, 1998, Curr. Opin. Genet. Dev. 8:351-359; Tarahovsky and Ivanitsky, 1998, Biochemistry (Mosc) 63:607-618; Morishita et al., 1998, Circ. Res. 2:1023-1028; Vile et al., 1998, Mol. Med. Today 4:84-92; Branch and Klotman, 1998, Exp. Nephrol. 6:78-83; Ascenzioni et al., 1997, Cancer Lett. 118:135-142; Chan and Glazer, 1997, J. Mol. Med. 75:267-282. Methods commonly known in the art of recombinant DNA technology which can be used are described in Ausubel et al. (eds.), 1993, Current Protocols in Molecular Biology, John Wiley & Sons, NY; and Kriegler, 1990, Gene Transfer and Expression, A Laboratory Manual, Stockton Press, NY.

In an embodiment in which recombinant precursor cells are used in gene therapy, a gene whose expression is desired in a patient is introduced into the precursor cells such that it is expressible by the cells and/or their Manipulated progeny, and the recombinant cells are then administered in vivo for therapeutic effect.

Recombinant Manipulated cells can be used in any appropriate method of gene therapy, as would be recognized by those in the art upon considering this disclosure. The resulting action of recombinant Manipulated cells administered to a patient can, for example, lead to the activation or inhibition of a pre-selected gene in the patient, thus leading to improvement of the diseased condition afflicting the patient.

The desired gene is transferred to precursor or Manipulated cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the desired gene is introduced into a precursor or Manipulated cell prior to administration in vivo of the resulting recombinant cell. Such introduction can be carried out by any method known in the art, including but not limited to transfection, electroporation, microinjection, infection with a viral or bacteriophage vector containing the gene sequences, cell fusion, chromosome-mediated gene transfer, microcell-mediated gene transfer, spheroplast fusion, etc. Numerous techniques are known in the art for the introduction of foreign genes into cells (see e.g., Loeffler and Behr, 1993, Meth. Enzymol. 217:599-618; Cohen et al., 1993, Meth. Enzymol. 217:618-644; Cline, 1985, Pharmac. Ther. 29:69-92) and may be used in accordance with the present invention, provided that the necessary developmental and physiological functions of the recipient cells are not disrupted. The technique should provide for the stable transfer of the gene to the cell, so that the gene is expressible by the cell and preferably heritable and expressible by its cell progeny.

One common method of practicing gene therapy is by making use of retroviral vectors (see Miller et al., 1993, Meth. Enzymol. 217:581-599). A retroviral vector is a retrovirus that has been modified to incorporate a preselected gene in order to effect the expression of that gene. It has been found that many of the naturally occurring DNA sequences of retroviruses are dispensable in retroviral vectors. Only a small subset of the naturally occurring DNA sequences of retroviruses is necessary. In general, a retroviral vector must contain all of the cis-acting sequences necessary for the packaging and integration of the viral genome. These cis-acting sequences are:

a) a long terminal repeat (LTR), or portions thereof, at each end of the vector;
b) primer binding sites for negative and positive strand DNA synthesis; and
c) a packaging signal, necessary for the incorporation of genomic RNA into virions.

The gene to be used in gene therapy is cloned into the vector, which facilitates delivery of the gene into a precursor cell by infection or delivery of the vector into the cell.

More detail about retroviral vectors can be found in Boesen et al., 1994, Biotherapy 6:291-302, which describes the use of a retroviral vector to deliver the mdr1 gene to hematopoietic stem cells in order to make the stem cells more resistant to chemotherapy. Other references illustrating the use of retroviral vectors in gene therapy are: Clowes et al., 1994, J. Clin. Invest. 93:644-651; Kiem et al., 1994, Blood 83:1467-1473; Salmons and Gunzberg, 1993, Human Gene Therapy 4:129-141; and Grossman and Wilson, 1993, Curr. Opin. in Genetics and Devel. 3:110-114.

Adenoviruses are also of use in gene therapy. Adenoviruses are especially attractive vehicles for delivering genes to respiratory precursor cells. Adenoviruses can also be used to deliver genes to precursor cells from the liver, the central nervous system, endothelium, and muscle. Adenoviruses have the advantage of being capable of infecting non-dividing cells. Kozarsky and Wilson, 1993, Current Opinion in Genetics and Development 3:499-503 present a review of adenovirus-based gene therapy. Other instances of the use of adenoviruses in gene therapy can be found in Rosenfeld et al., 1991, Science 252:431-434; Rosenfeld et al., 1992, Cell 68:143-155; and Mastrangeli et al., 1993, J. Clin. Invest. 91:225-234.

It has been proposed that adeno-associated virus (AAV) be used in gene therapy (Walsh et al., 1993, Proc. Soc. Exp. Biol. Med. 204:289-300). It has also been proposed that alphaviruses be used in gene therapy (Lundstrom, 1999, J. Recept. Signal Transduct. Res. 19:673-686).

Other methods of gene delivery in gene therapy include mammalian artificial chromosomes (Vos, 1998, Curr. Op. Genet. Dev. 8:351-359); liposomes (Tarahovsky and Ivanitsky, 1998, Biochemistry (Mosc) 63:607-618); ribozymes (Branch and Klotman, 1998, Exp. Nephrol. 6:78-83); and triplex DNA (Chan and Glazer, 1997, J. Mol. Med. 75:267-282).

A desired gene can be introduced intracellularly and incorporated within host precursor cell DNA for expression, by homologous recombination (Koller and Smithies, 1989, Proc. Natl. Acad. Sci. USA 86:8932-8935; Zijlstra et al., 1989, Nature 342:435-438).

In a specific embodiment, the desired gene recombinantly expressed in the precursor or Manipulated cell to be introduced for purposes of gene therapy comprises an inducible promoter operably linked to the coding region, such that expression of the recombinant gene is controllable by controlling the presence or absence of the appropriate inducer of transcription.

In a preferred embodiment, the desired gene recombinantly expressed in the precursor or Manipulated cells, whether its function is to elicit a cell fate change according to the methods of the invention or to provide a therapeutic value to Manipulated cells, is flanked by Cre sites. When the gene function is no longer required, the cells comprising the recombinant gene are subjected to Lox protein, for example be means of supplying a nucleic acid containing the Lox coding sequences functionally coupled to an inducible or tissue specific promoter, or by supplying Lox protein functionally coupled to a nuclear internalization signal. Lox recombinase functions to recombine the Cre sequences (Hamilton et al., 1984, J. Mol. Biol. 178:481-486), excising the intervening sequences in the process, which according to this embodiment contain a nucleic acid of a desired gene. The method has been used successfully to manipulate recombinant gene expression (Fukushige et al., 1992, Proc. Natl. Acad. Sci. USA 89:7905-7909). Alternatively, the FLP/FRT recombination system can be used to control the presence and expression of genes through site-specific recombination (Brand and Perrimon, 1993, Development 118:401-415).

In a preferred aspect of the invention, gene therapy using nucleic acids encoding Notch and Pax6 is directed to the treatment of macular degeneration (See Section 5.10.4, infra). Suitable strategies for ocular gene therapy are described by da Cruz et al., 1997, Aust. NZ J. Opthalmol. 25:97-104.

5.11. Uses of the Manipulated Cells of the Invention

5.11.1. "Bioreactor" Cell Lines

In one embodiment of the invention, the Manipulated cells are used as bioreactor cells lines that are used to produce large quantities of proteins that have therapeutic applications, i.e. proteins whose expression is associated with the cell fate assumed by the Manipulated cells. In one preferred embodiment, the Manipulated cell is specialized to produce the therapeutic protein, e.g. a cell specialized for secretion such as an endocrine or mammary gland cell used to generate a bioreactor cell line for the production of a secreted product such as a hormone or growth factor. The protein with therapeutic value may be expressed endogenously by the Manipulated cell; alternatively, the Manipulated cell may be genetically engineered to express the therapeutic protein by the methods described in Section 5.4, supra, e.g. by transfecting the cell with vector comprising a recombinant DNA molecule encoding the therapeutic protein functionally coupled to a basal promoter and, preferably, functionally coupled to an inducible promoter. In one embodiment, the bioreactor cell is a Manipulated cell that is not easily grown in culture and therefore expanded and cultured as a precursor cell line, being manipulated by the Notch and cell fate control gene pathways immediately prior to the induction of the expression of the therapeutic protein. In one embodiment, the cells transfected with the vector encoding the therapeutic protein are the precursor cells, i.e. prior to manipulation of the cells by the methods of the present invention. In another embodiment, the cells transfected with the vector encoding the therapeutic are the Manipulated cells, i.e. after altering the fate of the precursor cells by the methods of the present invention.

In a preferred embodiment, the Manipulated bioreactor cells express growth factors (e.g. fibroblast growth factors (FGF's), platelet derived growth factors (PDGF's) and epidermal growth factors (EGF's)).

5.11.2. Tissue and Organ Models

The methods of the instant application can be used to provide Manipulated cells of specific tissue types for use as tissue and/or organ models for research, including medical and pharmaceutical research. The Manipulated cells can be used as models for skin, liver, kidney, heart, bone, etc. The Manipulated cells can be used to identify factors involved in normal homeostasis of tissues and cells; to study changes that are triggered in the tissues during pathogenesis or trauma or infection; to test therapeutics, e.g. drugs, hormones, growth factors and gene therapy vehicles; to assay the toxicity or carcinogenicity of various compounds, e.g. drugs or food additives or cosmetics; etc. In one specific embodiment, the Manipulated cells produced by the methods of the invention are used as a skin model to test cosmetics, tanning products, sun protection products, etc. In another specific embodiment, the Manipulated cells produced by the methods of the invention are used as a liver model for infection with hepatitis viruses, alone or in combination, and for screening drugs for the treatment of hepatitis infections.

5.11.3. Treatment of Cancer

In a specific embodiment of the present invention, the methods of the present invention are directed to promoting or inducing programmed cell death in an undesirable cell type, such as an immortalized cell, e.g. a cancer cell, preferably by contacting the cell in vivo with polypeptides and/or nucleic acids that induce cell death according to the methods of the present invention.

Cancers that can be treated by the methods of the present invention include, but are not limited to human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenström's macroglobulinemia, and heavy chain disease.

5.11.4. Treatment of Nervous System Disorders and Injuries

Nervous system disorders, involving cell types that require supplementation or replacement and that can be differentiated in vitro and replenished by transplantation can be treated by the methods of the invention. These include but are not limited to nervous system injuries, and diseases or disorders which result in either a disconnection of axons, a diminution or degeneration of neurons, or demyelination. Nervous system lesions which may be treated in a patient (including human and non-human mammalian patients) according to the invention include but are not limited to the following lesions of either the central (including spinal cord, brain) or peripheral nervous systems:

(i) traumatic lesions, including lesions caused by physical injury or associated with surgery, for example, lesions which sever a portion of the nervous system, or compression injuries;

(ii) ischemic lesions, in which a lack of oxygen in a portion of the nervous system results in neuronal injury or death, including cerebral infarction or ischemia, or spinal cord infarction or ischemia;

(iii) malignant lesions, in which a portion of the nervous system is destroyed or injured by malignant tissue which is either a nervous system associated malignancy or a malignancy derived from non-nervous system tissue;

(iv) infectious lesions, in which a portion of the nervous system is destroyed or injured as a result of infection, for example, by an abscess or associated with infection by human immunodeficiency virus, herpes zoster, or herpes simplex virus or with Lyme disease, tuberculosis, syphilis;

(v) degenerative lesions, in which a portion of the nervous system is destroyed or injured as a result of a degenerative process including but not limited to degeneration associated with Parkinson's disease, Alzheimer's disease, Huntington's chorea, or amyotrophic lateral sclerosis;

(vi) lesions associated with nutritional diseases or disorders, in which a portion of the nervous system is destroyed or injured by a nutritional disorder or disorder of metabolism including but not limited to, vitamin B12 deficiency, folic acid deficiency, Wernicke disease, tobacco-alcohol amblyopia, Marchiafava-Bignami disease (primary degeneration of the corpus callosum), and alcoholic cerebellar degeneration;

(vii) neurological lesions associated with systemic diseases including but not limited to diabetes (diabetic neuropathy, Bell's palsy), systemic lupus erythematosus, carcinoma, or sarcoidosis;

(viii) lesions caused by toxic substances including alcohol, lead, or particular neurotoxins; and (ix) demyelinated lesions in which a portion of the nervous system is destroyed or injured by a demyelinating disease including but not limited to multiple sclerosis, human immunodeficiency virus-associated myelopathy, transverse myelopathy or various etiologies, progressive multifocal leukoencephalopathy, and central pontine myelinolysis.

In a specific embodiments, motor neuron disorders that may be treated according to the invention include but are not limited to disorders such as infarction, infection, exposure to toxin, trauma, surgical damage, degenerative disease or malignancy that may affect motor neurons as well as other components of the nervous system, as well as disorders that selectively affect neurons such as amyotrophic lateral sclerosis, and including but not limited to progressive spinal muscular atrophy, progressive bulbar palsy, primary lateral sclerosis, infantile and juvenile muscular atrophy, progressive bulbar paralysis of childhood (Fazio-Londe syndrome), poliomyelitis and the post polio syndrome, and Hereditary Motorsensory Neuropathy (Charcot-Marie-Tooth Disease).

5.11.5. Tissue or Organ Replacement or Transplantation

In one embodiment of the invention, a Therapeutic of the invention is used to supplement or replace tissues during regeneration and repair processes. In another embodiment, a Therapeutic of the invention is used to treat degenerative or traumatic disorders of the sensory epithelium of the inner ear.

In yet another embodiment of the invention, a Therapeutic of the invention is used to transplant organs, tissues or cells generated by the methods of the invention to supplant or replace tissues compromised by disease, for example liver tissue, lung tissue, pancreatic tissue, skin, cartilage, bone, hematopoietic cells, intestine, heart, kidney, etc. Liver tissue can be transplanted into patients whose livers have been compromised or destroyed by diseases such as hepatitis, cirrhosis or toxic medications. Lung tissue can be used to supplement the lung function of patients whose own lungs are not able to provide sufficient function after the removal of tumors of the lung; similarly, intestinal tissue can be used to replace portions of the intestines removed after cancer surgery. Cartilage transplantation is suitable for the reparation of ear and nose defects in children. Skin grafts are used for burn patients. Transplantation of pancreatic cells is suitable after pancreas removal (e.g. after cancer surgery) or for treatment of severe diabetes. In the latter situation, pancreatic cells genetically engineered to express insulin are preferably used. Bone tissue can be grafted to replace or supplement missing bone. Bone grafts are often used by the body as scaffolds in the formation of new bone tissue. Thyroid tissue can be transplanted into a patient in whom the functional cells of the thyroid are destroyed, e.g. by Hashimoto's thyroiditis. Corneal transplantation is suitable for those patients who have lost the function of the cornea, e.g. because of diabetes or infection. Hematopoietic or immune cells can be administered to patients who are immunocompromised or immunosuppressed or have an immune deficiency, for example as a result of Acquired Immune Deficiency Syndrome or exposure to radiation or chemotherapy regimens for the treatment of cancer, such that the administered cells perform a needed immune or hematopoietic function.

In a most preferred embodiment, the methods of the invention provide retinal pigment epithelium for use in the treatment of macular degeneration. Macular degeneration is primarily an age-related disease which results in photoreceptor and retinal degeneration of the macula, i.e. the area in the eye which enables the discernment of small details and reading. Macular degeneration is the leading cause of blindness and occurs to various degrees in about 10% of the population over the age of 50 and about 30% of the population over the age of 75. Today no effective treatment available to prevent or delay the development of macular degeneration. In one mode of the embodiment, the retinal pigment epithelium is generated in vitro by producing the same cell type utilizing the methods of the invention, as described supra. In a preferred mode of the embodiment, the retinal pigment epithelium is generated in vivo by contacting the macular area, including the retinal pigment epithelium and/or neuroepithelium with a Therapeutic that serves to activate both the Notch and Pax6 pathways. In one aspect, the Therapeutic comprises nucleic acids encoding Notch or an active form of a member of the Notch pathway (as described in Section 5.3) harbored in gene therapy vectors (as described in Section 5.9). In a highly preferred aspect, the Therapeutic comprises an active Notch protein or ligand (described in Section 5.3) and Pax6 protein, preferably functionally coupled to a nuclear internalization signal, together with a pharmaceutically acceptable carrier.

It will be understood to those skilled in the art that the above embodiments are merely exemplary; the Therapeutics of the invention may be applied to any disease that requires cell or tissue supplementation.

5.11.6. Cosmetic Applications

Many aspects of cosmetic surgery involve the introduction of foreign objects into the human body. In one non-limiting example, breast enlargement comprises the insertion of sacs containing silicone or saline. These sacs are under the danger of rupturing or leaking, causing deleterious side effects, and also prevent women from nursing their infants. Thus, cells from the plastic surgery patient can be manipulated by the methods of the invention into breast tissue and, in one embodiment, the Manipulated tissue implanted in place of saline or silicone sacs. In another embodiment, the breast tissue implants of Manipulated cells are used after a mastectomy.

5.11.7. Coating Implants

The Manipulated cells of the invention can be used to coat synthetic implants or prosthetic devices for the purpose of improving the biocompatibility of the implant or imparting biological activity to the implant. Prosthetic devices are often used in surgical applications, for example in reconstructive or joint replacement surgery. The material of choice for prosthetic implants is metal, usually titanium, although other materials, e.g. ceramics, may be used. Prosthetic devices are often anchored at the site of implantation with synthetic cements. In recent times, implants have been coated with thin, porous materials to allow the surrounding tissue to grow into the porous layers encapsulating the implants. However, it is more desirable to encapsulate such prosthetic implants with cell types found at the site of implantation, which would promote more successful anchoring and integration. A method to generate cells of the type of tissue found at the site of prosthetic implantation is highly desirable for use in coating the prosthetic device. Thus, in one aspect of the invention, the Manipulated cells are used to coat prosthetic devices for implantation into humans. The prosthetic devices to be coated by the Manipulated cells include but are not limited to joint components (for example for knees, shoulders and hips), heart valve replacements, spinal disc implants, ossicular bone replacements and plates/rods for bone (e.g. femur, tibia) remodeling. In a preferred embodiment, the Manipulated cells used to coat the prosthetic implants are autologous to the individual.

5.12. Methods of Transplantation

The Manipulated cell populations of the present invention, whether recombinantly expressing a desired gene or not, can be transplanted into a patient for the treatment of disease or injury or for gene therapy by any method known in the art which is appropriate for the type of stem cells being transplanted and the transplant site. Hematopoietic cells can be transplanted intravenously, as can liver cells which will locate to the liver. Neural cells can be transplanted directly into the brain at the site of injury or disease. Skin cells can be used for grafts, to treat burns, etc. Mesenchymal cells can be used to coat prosthetic devices prior to implantation (as described supra).

Methods of introduction include but are not limited to intradermal, intramuscular, intraperitoneal, intravenous, subcutaneous, intranasal, and epidural routes. The Therapeutics may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir.

In a specific embodiment, it may be desirable to administer the Therapeutics of the invention locally to the area in need of treatment; this may be achieved by, for example, and not by way of limitation, local infusion during surgery, topical application, e.g., in conjunction with a wound dressing after surgery, by injection, by means of a catheter, or by means of an implant, said implant being of a porous, non-porous, or gelatinous material, including membranes, such as sialastic membranes, or fibers.

The following describes exemplary methods which can be modified for the transplantation of Manipulated cells: Protocols for the isolation and transplantation of fetal tissues in humans have been reported and clinical trials involving these studies having been carried out. For example, Lindvall et al., 1990, Science 247:574-577, have described results regarding grafts and survival of fetal dopamine neurons after transplantation into brain. Rinsing and partial dissociation of precursor cells, if necessary, can be carried out by a modification of the protocol described in Lindvall et al., 1989, Arch. Neurol. 46:615.

By way of example, implantation of cells into the brain can be performed as follows. Implantation is done at three sites in the left putamen with a stereotactic technique (Lindvall et al., 1989, Arch. Neurol. 46:615). For each site, 20 µl of the dissociated cells is drawn into the instrument (outer diameter, 1.0 mm). The cells are injected along a 10, 12 and 14 mm linear tract, respectively, in either 2.5 µl portions for 15 to 20 seconds each. Between each injection there is a 2 minute delay, and the cannula is then retracted 1.5 to 1.7 mm. After the final injection, the cannula is left in situ for 8 minutes before being slowly withdrawn from the brain. After surgery the cell viability is assessed following the procedure of Brundin et al., 1985 (Brain. Res. 331:251).

Another example is outlined by Caplan et al., 1993, U.S. Pat. No. 5,226,914. Briefly, after marrow cells are harvested from bone marrow plugs and the marrow mesenchymal, stem cells are separated by centrifugation. The stem cells are isolated further by selective adherence to the plastic or glass surface of a tissue culture dish. The stem cells are allowed to proliferate but not differentiate. Porous ceramic cubes composed of 60% hydroxyapatite and 40% β-tricalcium phosphate are added to the cells under a slight vacuum. The cubes with adhered cells are implanted into incisional pockets along the backs of nude mice. The mesenchymal stem cells differentiate into bone.

In a preferred embodiment, the cell transplant is autologous. In another embodiment, the transplant is non-autologous. In a specific embodiment, the transplanted cells can be an organ or tissue type produced according to the methods of the invention.

The titer of stem cells transplanted or the amount of the Therapeutic of the invention which will be effective in the treatment of a particular disorder or condition will depend on the nature of the disorder or condition, and can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances.

5.13. Pharmaceutical Compositions

The invention provides methods of treatment by administration to a subject of a pharmaceutical (therapeutic) composition comprising a therapeutically effective amount of a recombinant or non-recombinant Manipulated cell. Such a Manipulated cell or recombinant Manipulated stem cell envisioned for therapeutic use is referred to hereinafter as a "Therapeutic" or "Therapeutic of the invention." In a preferred aspect, the Therapeutic is substantially purified. The subject is preferably an animal, including but not limited to animals such as cows, pigs, horses, chickens, cats, dogs, etc., and is preferably a mammal, and most preferably human.

The present invention provides pharmaceutical compositions. Such compositions comprise a therapeutically effective amount of a Therapeutic, and a pharmaceutically acceptable carrier or excipient. Such a carrier includes but is not limited to saline, buffered saline, dextrose, water, glycerol, ethanol, and combinations thereof. The carrier and composition can be sterile. The formulation should suit the mode of administration.

The composition, if desired, can also contain minor amounts of wetting or emulsifying agents, or pH buffering agents. The composition can be a liquid solution, suspension, or emulsion.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection.

5.13.1. Pharmaceutical Kits

The invention also provides a pharmaceutical pack or kit comprising one or more containers filled with one or more of the ingredients of the pharmaceutical compositions of the invention and/or reagents to prepare said pharmaceutical compositions. Optionally associated with such container(s) can be a notice in the form prescribed by a governmental agency regulating the manufacture, use or sale of pharmaceuticals or biological products, which notice reflects approval by the agency of manufacture, use or sale for human administration.

6. EXAMPLE

Notch Signaling and the Determination of Appendage Identity

How organ identity is determined is one of the fundamental questions in developmental biology. In *Drosophila* the imaginal discs, the primordia of the trunk and the appendages of the adult fly, provide a unique system to study the determination of organ identity. Homeotic genes play are known to play important roles in determining organ identity; however, by themselves they do not provide the complete set of instructions for determining the identity of an organ. For example, Antp is capable of inducing both ventral (second leg) and dorsal mesothoracic structures (notum and wing), which indicates that homeotic genes specify body segments rather than organs, depending on the context. Therefore, the problem of the specification of organ identity remains open. In the example set forth below, an analysis of the roles of other cell fate control genes (described in Section 2.3, supra) and Notch (described in Section 2.2, supra) in the process of organogenesis is described. It is concluded that Notch signaling is involved in a regulatory pathway for the determination of the identity of the appendages of *Drosophila*.

6.1. Materials and Methods

Histochemistry: For immunohistochemistry, staged larvae were dissected in cold phosphate-buffered saline (PBS) and fixed in PEM (100 mM Pipes pH 6.9, 2 mM $MgSO_4$, 1 mM EGTA, 4% Formaldehyde) for 25 minutes on ice. After washing with PBT (PBS containing 0.3% Triton X-100), blocking was performed in PBTB (PBS containing 0.3% Triton X-100 and 5% bovine serum albumin) for two hours at 4° C. Antibody staining was performed using as primary antibodies mouse anti-β-galactosidase (Promega) at 1:1,000, rat anti-ELAV48 at 1:20, rat anti-EY (Halder et al., 1998, Development 125:2181-2191) at 1:300, Mouse anti-MYC (Calbiochem) at 1:100, Mouse anti-DLL (Diaz-Benjumea et al., 1994, Nature 372:175-179) at 1:10 and rabbit anti-VG (Williams et al., 1991, Genes Dev. 5:2481-2495) at 1:200 overnight at 4° C. Immunofluorescent detection was performed using DTAF and Cy3 conjugated donkey anti-IgGs (Jackson Immunoresearch). After washing with PBTB, discs were dissected in PBS and mounted in Vectashield (Vector). The preparations were analyzed on a Zeiss Axiophot microscope equipped for epifluorescence.

β-galactosidase staining was performed as described (Ashburner, 1989, *Drosophila*, A Laboratory Manual, protocol 77, Cold Spring Harbor Laboratory Press, Cold Spring harbor, N.Y.). For cuticle preparations, adults were dissected in PBS, mounted in Faure's mounting medium. For scanning electron microscopy, freshly hatched flies were immersed in 70% acetone. After critical point drying, they were mounted and coated with gold. The specimens were observed with a Hitachi S-88 field emission electron microscope at 6-12 kV. For in situ hybridization, the probes were labeled with dig-dUTP and detected by digoxigenin antibodies (Boehringer).

Clonal analysis: Su(H) mutant clones were induced using the FLP/FRT technique in larvae of the genotype w HSFlp; $Su(H)^{SF8}$ FRT40A/N-myc FRT40A. 30-60 hours after egg laying, clones were induced by heat shock for 2 hours at 39° C. After growth at 25° C., larvae were heat shocked for 2 hours at 38° C. to induce MYC expression. After 90 minutes of recovery at 25° C., eye imaginal discs were fixed and stained with rat anti-EY and mouse anti-MYC antibodies.

6.2. Opposite Effects of Inhibition and Activation of Notch Signaling on Eye Morphogenesis The intracellular domain of the truncated Notch receptor represents a constitutively activated state (Notch activated, $N^{act}$) and the extracellular domain of the truncated receptor mimics loss-of-function phenotypes and represents the dominant negative form (Notch dominant negative, $N^{dn}$; Fortini et al., 1993, Nature 365:555-557; Rebay et al., 1993, Cell 74:319-329). To examine the role of Notch signaling in early eye development, these truncated forms were expressed in the early eye imaginal disc. Using the GAL4 system (Brand and Perrimon, 1993, Development 118:401-415) with the eye specific enhancer of the ey gene (Hauck et al., 1999, Proc. Natl. Acad. Sci. USA 96:564-9) to target $N^{dn}$ expression to the eye disc at an early stage of eye development. This eye-specific enhancer induces $N^{dn}$ expression in the eye primordia of the embryo and maintains expression throughout eye morphogenesis. In contrast to ey expression in the wild type eye-antennal disc, the enhancer-driven reporter gene expression is not down-regulated in the differentiating cells posterior to the morphogenetic furrow but it extends all over the eye disc and into the area of the antennal disc where the rostral membrane is going to be formed (FIG. 1C). However, the activation in the antennal disc is quite variable from disc to disc. Crossing ey enhancer-GAL4 (ey-GAL4) flies to a stock carrying $N^{dn}$ under an upstream activating sequence for GAL4 (UAS-$N^{dn}$) results in a strongly reduced eye phenotype in all transheterozygous flies similar to that of the $ey^2$ mutant (FIG. 1A), suggesting a crucial role of Notch signaling in eye development. Inhibition of Notch signaling by misexpression of Hairless (H) and dominant negative forms of Delta (Dl) and Serrate (Ser) also leads to a reduction or complete absence of the eye (Go et al., 1998, Development 125:2031-2040; Sun and Artavanis-Tsakonas, 1997, Development 124:3439-3448).

Activation of Notch signaling by crossing ey-GAL4 flies to a UAS-$N^{act}$ line leads to significant pupal lethality but all transheterozygotes that escaped lethality showed hyperplasia of the eyes with a significant increase in the number of facets (FIG. 1B,D). The disc overgrowth is found in all eye discs of ey-GAL4 UAS-N$^{act}$ larvae, consistent with a role of Notch signaling in growth control of the eye imaginal discs. Furthermore, about 16% of the escapers (19/119) formed ectopic eyes on the rostral membrane of the head (FIG. 1B,D). The frequency of ectopic eye induction may correspond to the variable expression of ey-GAL4 in the area of antennal disc where the ectopic eye is formed.

The relationship between the site of ectopic eye formation and the cells expressing N$^{act}$ by immunostaining of eye-antennal discs of double transheterozygous larvae of the genetic constitution ey-GAL4 UAS-lacZ UAS-N$^{act}$ was further examined using an ELAV antibody to identify the differentiating photoreceptor cells and a β-galactosidase antibody to indirectly localize the N$^{act}$ protein respectively. The strong hyperplasia of the eye disc was associated with the expression of lacZ (FIG. 1E) and expression of ELAV revealing the clusters of photoreceptor cells was observed at the site of ectopic eye formation in the antennal disc (FIG. 1F). These results indicate that activation of Notch signaling correlates with ectopic eye induction. However, the time window for expression of the truncated receptors is critical. Transheterozygotes in which either N$^{dn}$ or N$^{act}$ were driven by the glass promoter GMR-GAL4 which drives expression in all cells posterior to the furrow only (Ellis et al., Development 119:855-865), showed only a mild phenotypic effect. As reported previously (Fortini et al., 1993, Nature 365:555-557; Rebay et al., 1993, Cell 74:319-329), N$^{dn}$ results in a roughening of the eye, whereas N$^{act}$ produces a polished eye phenotype. These findings indicate that the strong effects of Notch signaling on eye morphogenesis are restricted to early stages of eye development.

6.3. Notch Signaling Regulates Eyeless Expression

The reduced eye phenotype caused by expression of N$^{dn}$ and the induction of ectopic eyes by the expression of N$^{act}$ are similar not only to loss and gain mutants of ey but also resemble two other mutations acting downstream in the ey developmental pathway, eyes absent (eya; Bonini et al., 1998, Development 124:4819-4826) and dachshund (dac; Shen and Mardon, 1997, Development 124:45-52). The function of ey is required for expression of eya and dac but not vice versa (Bonini et al., 1998, Development 124:4819-4826; Shen and Mardon, 1997, Development 124:45-52; Halder et al., 1998, Development 125:2181-2191). The second Pax-6 gene of *Drosophila*, twin of eyeless (toy), was found to be an upstream regulator of ey capable of inducing ectopic eyes by inducing ey expression (Czerny et al., 1999, Mol. Cell 3:297-307)

To determine whether Notch signaling acts upstream of ey and toy or downstream like eya and dac, the effect of N$^{dn}$ on ectopic eye induction by ey and toy was studied. A dpp-enhancer GAL4 line30 (dpp-GAL4) was crossed to flies carrying both UAS-N$^{dn}$ and UAS-ey or alternatively to UAS-N$^{dn}$ and UAS-toy. Transheterozygotes from both crosses exhibited ectopic eyes on legs and wings in all flies. The size of the ectopic eyes were similar to those of the transheterozygous controls dpp-GAL4 UAS-ey and dpp-GAL4 UAS-toy respectively. These results indicate that Notch signaling is not required downstream of toy and ey and suggests that Notch acts upstream. Therefore, the effect of activation of Notch signaling on ey and toy expression was determined. For this purpose, double immunostaining of eye-antennal discs from transheterozygous ey-GAL4 UAS-N$^{act}$, UAS-lacZ was performed by using an anti-ey antibody to reveal ey protein and anti-β-galactosidase antibody to indirectly reveal N$^{act}$. The enhanced expression of ey was induced in all eye discs by the activation of Notch signaling. Moreover, strong ectopic expression of ey was observed (FIG. 2B). The ectopic expression pattern of ey corresponds to that of lacZ reflecting the expression of N$^{act}$ protein (FIG. 2A). Analysis of ey expression by in situ hybridization indicates that ey is induced at the transcriptional level. Similarly, ectopic expression of toy was also induced in the antennal discs of ey-GAL4 UAS-N$^{act}$ larvae. This demonstrates that activation of Notch signaling can induce toy and ey expression in antennal discs.

To examine the requirement for Notch signaling for the expression of ey in eye-discs where it is normally expressed, clones of cells homozygous for a Suppressor of Hairless (SU(H)) mutation—which therefore cannot mediate the Notch signal (Fortini and Artavanis-Tsakonas, 1994, Cell 79:273-282)—were generated in the eye disc by the FLP recombinase technique (Xu and Rubin, 1993, Development 117:1223-1237). The eye discs were examined for ey expression in and around the clones. Su(H) mutant cells generated anterior to the morphogenetic furrow in the eye disc failed to express ey (FIG. 3) and the failure to express ey was confined to the clones, indicating that the requirement for Su(H) is cell autonomous (FIG. 3). In Su(H) mutant clones no adult eye structures were formed, indicating that Notch signaling is required for eye morphogenesis. These results demonstrate that Notch signaling regulates ey expression during eye morphogenesis. Both ligands, Dl and Ser, can activate the Notch receptor, and Su(H) mediates the activation of Notch to induce the expression of toy and ey.

6.4. Activation of Notch Signaling in an Eyeless Mutant Background Induces Ectopic Antennae The effect of activation of Notch signaling on eye morphogenesis was also tested in a ey$^2$ hypomorphic mutation. Approximately 72% (63/88) of the ey-GAL4 UAS-N$^{act}$ ey$^2$ flies that survived were found to have reduced eyes. About 15% of these flies (13/88) had both a reduced original and a reduced ectopic eye (FIG. 4A), indicating that N$^{act}$ is functioning in this situation. Similar results were obtained with ey$^R$, another hypomorphic mutation. These results confirm that ey acts downstream of Notch signaling.

In addition to ectopic eyes N$^{act}$ also induced ectopic antennae in 25% (22/88) of these flies on the side of the head that is derived from the eye disc. Many of the induced ectopic antennae were complete with all three antennal segments and the arista (FIG. 4B). Similar results were also obtained with ey$^R$, the other hypomorphic allele. Since no ectopic antennae were found in ey-GAL4 UAS-N$^{act}$ ey$^+$ flies (FIG. 1B,D), these findings indicate that Notch signaling induces not only eye morphogenesis, but also antenna formation in a loss of function ey mutant background.

6.5. Activation of Notch Signaling Combined with the Ectopic Expression of Antennapedia Induces Ectopic Wings and Legs on the Head The observation that N$^{act}$ can induce both ectopic eyes and, in a specific genetic background, antennae led the possibility that Notch signaling might also induce the formation of other appendages in a different genetic context. To test this hypothesis, the activation of Notch signaling with ectopic expression of Antennapedia (Antp) were combined. The latter is known to determine the identity of the second thoracic segment (T2) (Schneuwly et al., 1987, Nature 325:816-818; Czerny et al., 1999, Mol. Cell 3:297-307) which on the dorsal side gives rise to a pair of wings and on the ventral side to a pair of second legs. For this purpose, transgenic flies of the constitution ey-GAL4 UAS-N$^{act}$ UAS-Antp were generated. About 26% (17/65) of the flies escaping pupal lethality were found to have ectopic wings on the head (FIG. 5A). Almost all ectopic wing structures consisted of dorsal and ventral wing blades bordered by bristles of the wing margin (double and triple row), but lacking wing veins. In contrast, wing structures induced by the ectopic expression of vg, the wing margin is not formed (Kim et al., 1996, Nature 382:133-138), suggesting that Notch signaling and Antp are acting upstream of vg. Furthermore, about 17% (11/65) of these flies showed ectopic leg structures induced by secondary transformation of the ectopic antennal tissue into leg structures (e.g. arista into tarsus) (FIG. 5B). The ey-GAL4 UAS-Antp control flies did not show any ectopic wing structures, but they clearly exhibited reduced eyes suggesting that the ectopic expression of Antp partially represses ey in the eye discs of these animals. An additional 10% (7/71) of these flies showed a transformation of the original antenna to leg structures. On the heads of ey-GAL4 UAS-N$^{act}$ flies, no wing nor leg structures were found (FIG. 1B,D). Therefore, activation of Notch signaling when combined with the ectopic expression of Antp driven by ey-GAL4 is capable of inducing wing and leg structures on the head.

6.6. Notch Signaling Regulates Master Control Genes Specifying the Identity of the Various Appendages The developmental consequences of the synergy between Notch signaling and the activity of other genes controlling morphogenesis was further explored. In order to determine whether the activation of Notch signaling regulates other control genes, eye discs in which Notch signaling had been activated were examined for induction of Dll or vg. Dll specifies the ventral appendages, namely the leg and antenna (Gorfinkiel et al., Genes Dev. 11:2259-2271) while vg determines wing and haltere identity (Kim et al., 1996, Nature 382:133-138; Weatherbee, S. D. et al., 1996, Genes Dev. 12:1474-1482). These genes, Dll and vg, are not to be regarded as completely equivalent to ey as the master control genes of the respective appendages. Ectopic expression of vg and Dll is observed in all of the tested eye discs when ectopic structures are induced by Notch signaling, suggesting that the transformation is induced in all eye discs at the level of gene expression.

Figure 6A:
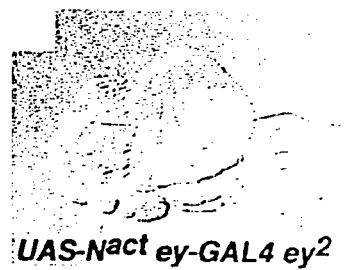
Figure 6B:
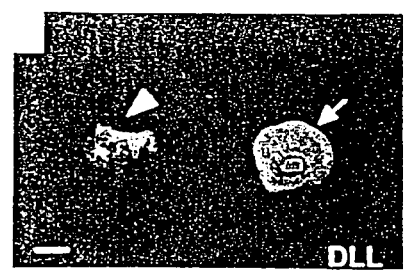
Figure 6C:
Figure 6D:
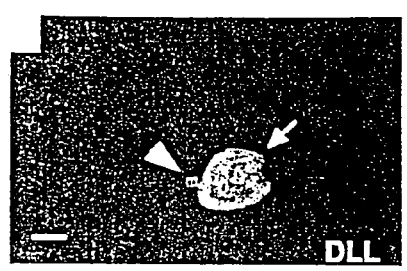
Figure 7A:
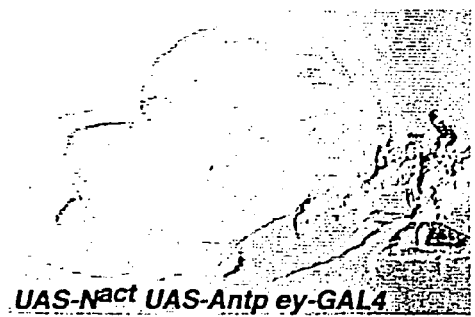
Figure 7B:
Figure 7C:
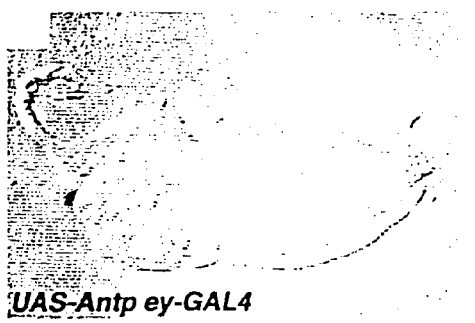
Figure 7D:
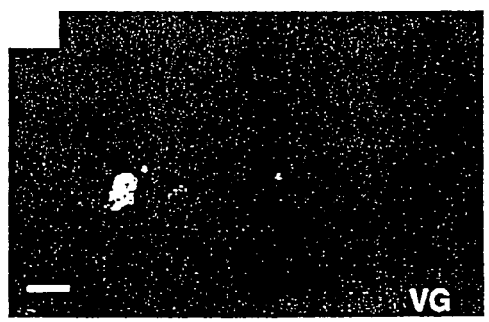
Figure 8A:
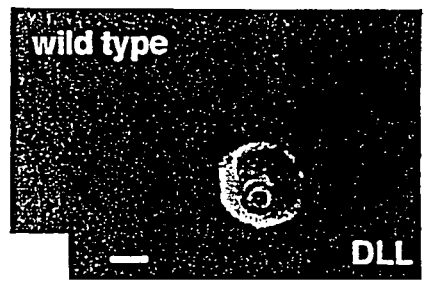
Figure 8B:

In wild type larvae, DLL protein is expressed in the antennal but not in the eye disc (FIG. 8A). In all of the tested discs (30/30) in ey-GAL4 UAS-N$^{act}$ ey$^2$ animals which form ectopic antennae from the eye disc, significant DLL expression was detected ectopically (FIG. 6B). By contrast, no ectopic expression of DLL was detected in the eye discs of ey$^2$ control larvae. In 14 out of 30 ey-GAL4 UAS-N$^{act}$ ey$^+$ larvae additional ectopic expression of DLL in a few cells of the antennal disc (FIG. 6D) was observed. This indicates that Notch signaling induces ectopic expression of Dll in the eye-antennal disc leading to the ectopic induction of antennae described above.

The vg gene is expressed in the wing but not in the eye disc of wildtype larvae (Williams et al., 1991, Genes Dev. 5:2481-2495). By contrast, in ey-GAL4 UAS-N$^{act}$ UAS-Antp animals in which ectopic wing structures are induced in the eye disc, all of the tested eye discs (25/25) showed significant ectopic expression of VG protein (FIG. 7B), whereas no ectopic expression of VG was detected in ey-GAL4 UAS-N$^{act}$ control larvae. However ey-GAL4 UAS-Antp larvae showed VG expression in a small region of the eye discs in 7 out of 11 tested discs (FIG. 7D), consistent with a synergistic effect of endogenous Notch activity with ectopic Antp expression on vg expression. Thus, activation of Notch signaling in context of Antp expression induces vg expression in the eye discs. Additionally, there are synergistic effects between Notch signaling and Antp expression. It has been shown (Kim et al., 1996, Nature 382:133-138) that the Notch signaling pathway is used to specifically activate the boundary enhancer of the vg gene necessary for D/V wing formation. This enhancer is potentially also used for ectopic formation of the wing.

In ey-GAL4 UAS-N$^{act}$ UAS-Antp flies, ectopic legs were also induced on the head (FIG. 5B) which is accompanied by DLL expression in 21 out of 21 tested eye discs. In contrast, no DLL expression was detected in eye discs of ey-GAL4 UAS-Antp larvae which is in agreement with the adult phenotype of these animals (FIG. 5).

A crucial role for Notch signaling has been established for wing morphogenesis (Kim et al., 1996, Nature 382:133-138; Artavanis-Tsakonas et al., 1995, Science 268:225-232; Neumann and Cohen, 1996, Development 122:3477-3485), but much less is known about its function in the development of normal antennae and legs. To study the role of Notch in these appendages, Dll-GAL4 flies were crossed to flies from a UAS-N$^{dn}$ line and the phenotypes of the antennae and legs of the progeny were examined. Dll-GAL4 drives expression in the central parts of both leg and antennal discs (Gorfinkiel et al., Genes Dev. 11:2259-2271), which corresponds to the distal segments of these appendages (Diaz-Benjumea et al., 1994, Nature 372:175-179). At 25° C. the transheterozygous Dll-GAL4 UAS-N$^{dn}$ flies are lethal during the pupal stage, but at 18° C. some escapers can be found which have reduced third antennal segments and show disorganization of the distal leg segments. The resulting leg phenotypes are similar to those observed in temperature-sensitive Dl mutants (Parody and Muskavitch, 1993, Genetics 135:527-539), supporting the conclusion that Notch signaling plays a crucial role not only in eye and wing morphogenesis, but also in antenna and leg development.

The effects of Notch signaling on the various appendages are dependent on the context provided by the control genes. In the eye primordia, Notch signaling induces ey expression, which induces a cascade of downstream genes leading to eye morphogenesis. In conjunction with Antp, Notch signaling induces vg leading to wing formation. At low levels of ey expression, Notch signaling induces Dll leading to antenna morphogenesis. In the case of the leg, Notch also induces Dll expression, which in conjunction with Antp leads to leg formation (Gorfinkiel et al., Genes Dev. 11:2259-2271).

6.7. Combinatorial Genetic Interactions Specify the Identity of the Various Appendages Segmental identity is specified by the homeotic genes that are active in a particular combination in each segment. Within a given segment, the appendages are specified by a different set of subsidiary control genes; the eyes are specified by ey, the wings and haltere by vg; the legs by Dll and the antennae by Dll in combination with extradenticle (exd) and homothorax (hth) (Casares and Mann, 1998, Nature 392:723-726; Gonzalez-Crespo et al., 1998, Nature 394:196-200). They are all regulated by Notch signaling, sharing the same cell signaling pathway, which implies that the appendage specificity is provided by a combinatorial interaction between Notch and the homeotic and subsidiary control genes. This is illustrated by the demonstration that Notch induces ey expression in the eye disc. However, in the presence of ANTP, which specifies the second thoracic segment, Notch signaling induces ectopic vg expression in the eye disc resulting in the formation of ectopic wing structures. Carroll et al. (Carroll et al., 1995, Nature 375:58-61) found that the wing primordia as judged by expression of the marker protein snail formed properly in Antp$^{w20}$ homozygous mutant embryos suggesting that Antp may not be required for wing formation. However, these results clearly indicate that Antp is involved in ectopic wing induction. Therefore, Antp function may also be required in normal wing development, a point that has to be investigated further.

Figure 8C:
Figure 8D:

The repression of one control gene by the expression of another seems to be a widespread mechanism to ensure that the developmental pathways are mutually exclusive so that the formation of intermediary cell types is prevented. Similar to the repression of ey by Antp, ey directly or indirectly represses Dll. In hypomorphic ey mutants, the activation of Notch signaling leads to ectopic expression of Dll in the eye disc, suggesting that ey might repress Dll in the wildtype eye disc. In dpp-GAL4 UAS-ey transheterozygous flies ey is expressed on the ventral side of the posterior half of the antennal discs under the control of the dpp-enhancer (FIG. 8D), whereas DLL is not detectable in this area (FIG. 8C). A similar mutually exclusive expression is found in the leg discs of these flies suggesting that ey represses Dll expression.

Based on these findings, model is proposed to explain the difference between the eye and antennal pathway starting from a common signaling mechanism. Notch signaling induces the expression of both ey and Dll. However, in the eye primordia ey represses Dll and induces eye morphogenesis. By contrast, in the antennal disc ey is repressed by a repressor resulting in Dll expression which confers antennal (ventral appendage) specificity. Two of the possible candidates for the repressor are the homeobox genes exd and hth, since both exd and hth mutant clones in the rostral membrane region of the antennal disc can result in ectopic eye development which is presumably due to derepression of ey (Gonzalez-Crespo and Morata, 1995, Development 121:2117-2125; Pai et al., 1998, Genes Dev. 12:435-446). Both exd and hth may also function in conjunction with Dll serving as co-repressors.

6.8. The Fundamental Role of Notch Signaling in Development and Evolution

Notch signaling regulates ey expression at the early stages of eye morphogenesis. By analogy to the *Drosophila* paradigm, it is therefore likely that the expression of Pax-6 is regulated by Notch signaling, given the extraordinary conservation of Notch function from ascidians (Hon et al., 1997, Dev. Genes Evol. 207:371-380) to mammals (Bao and Cepko, 1997, J. Neurosci. 17:1425-1434). Notch signaling participates in dorso-ventral patterning of the *Drosophila* wing (Kim et al., 1996, Nature 382:133-138; Neumann and Cohen, 1996, Development 122:3477-3485) and eye (Papayannopoulos et al., 1998, Science, 281:2031-2034) and also in the vertebrate limb (Rodriguez-Esteban et al., 1997, Nature 386: 360-366; Sidow et al., 1997, Nature 389:722-725). Thus, Notch is involved in the control of both vertebrate and invertebrate appendage formation. In describing the developmental role of Notch (Fleming et al., 1997, Trends Cell Biol. 7:437-441), it has been proposed that Notch signaling modulates the ability of individual precursor cells to respond to developmental signals, whether differentiation, proliferation or apoptotic cues. The present study extends the fundamental role of Notch by indicating that the implementation of entire developmental programs leading to appendage formation and organogenesis are controlled by Notch activity.

The present invention is not to be limited in scope by the specific embodiments described herein. Indeed, various modifications of the invention in addition to those described herein will become apparent to those skilled in the art from the foregoing description and accompanying drawings. Such modifications are intended to fall within the scope of the appended claims.

Various references are cited herein above, including patent applications, patents, and publications, the disclosures of which are hereby incorporated by reference in their entireties.

What is claimed is:

1. A kit comprising in one or more containers (a) an agonist of Notch pathway function selected from the group consisting of a Notch protein or a fragment of a Notch protein, a Delta protein or a fragment of a Delta protein, a Serrate protein or a fragment of a Serrate protein, a Jagged protein or a fragment of a Jagged protein, a Suppressor of Hairless protein or a fragment of a Suppressor of Hairless protein, a nucleic acid encoding a Notch protein or a fragment of a Notch protein, a nucleic acid encoding a Delta protein or a fragment of a Delta protein, a nucleic acid encoding a Serrate protein or a fragment of a Serrate protein, a nucleic acid encoding a Jagged protein or a fragment of a Jagged protein, a nucleic acid encoding a Suppressor of Hairless protein or a fragment of a Suppressor of Hairless protein, and a dominant-active Notch mutant; and (b) an agonist of a cell fate control gene pathway function, wherein the cell fate control gene is selected from the group consisting of a Pax gene, a HOX gene, a DLX gene, a Vestigial gene, a PBC gene, a MEINOX gene, a bHLH gene, a LIM homeobox gene, a MSX gene, a POU gene, a PTX gene, a NKX gene, a MADS box gene, a SOX gene, a T-box gene, a WNT gene, a BMP/TGF-β superfamily gene, and a hedgehog gene, and wherein the agonist of cell fate control gene pathway function is selected from the group consisting of a Pax protein, a HOX protein, a DLX protein, a Vestigial protein, a PBC protein, a MEINOX protein, a bHLH protein, a LIM homeobox protein, a MSX protein, a POU protein, a PTX protein, a NKX protein, a MADS box protein, a SOX protein, a T-box protein, a WNT protein, a BMP/TGF-β superfamily protein, a hedgehog protein, a nucleic acid encoding a Pax protein, a nucleic acid encoding a HOX protein, a nucleic acid encoding a DLX protein, a nucleic acid encoding a Vestigial protein, a nucleic acid encoding a PBC protein, a nucleic acid encoding a MEINOX protein, a nucleic acid encoding a bHLH protein, a nucleic acid encoding a LIM homeobox protein, a nucleic acid encoding a MSX protein, a nucleic acid encoding a POU protein, a nucleic acid encoding a PTX protein, a nucleic acid encoding a NKX protein, a nucleic acid encoding a MADS box protein, a nucleic acid encoding a SOX protein, a nucleic acid encoding a T-box protein, a nucleic acid encoding a WNT protein, a nucleic acid encoding a BMP/TGF-β superfamily protein, and a nucleic acid encoding a hedgehog protein.

2. A method for altering the cell fate otherwise adopted by a cell comprising:
   (a) contacting the cell in vitro with an agonist of Notch pathway function selected from the group consisting of a Notch protein or a fragment of a Notch protein, a Delta protein or a fragment of a Delta protein, a Serrate protein or a fragment of a Serrate protein, a Jagged protein or a fragment of a Jagged protein, a Suppressor of Hairless protein or a fragment of a Suppressor of Hairless protein, a nucleic acid encoding a Notch protein or a fragment of a Notch protein, a nucleic acid encoding a Delta protein or a fragment of a Delta protein, a nucleic acid encoding a Serrate protein or a fragment of a Serrate protein, a nucleic acid encoding a Jagged protein or a fragment of a Jagged protein, a nucleic acid encoding a Suppressor of Hairless protein or a fragment of a Suppressor of Hairless protein, and a dominant-active Notch mutant, thereby altering Notch pathway function in the cell;

(b) contacting the cell in vitro with an agonist of a cell fate control gene pathway function, wherein the cell fate control gene pathway is not the Notch pathway and wherein the cell fate control gene is selected from the group consisting of a Pax gene, a HOX gene, a DLX gene, a Vestigial gene, a PBC gene, a MEINOX gene, a bHLH gene, a LIM homeobox gene, a MSX gene, a POU gene, a PTX gene, a NKX gene, a MADS box gene, a SOX gene, a T-box gene, a WNT gene, a BMP/TGF-β superfamily gene, and a hedgehog gene, thereby altering the function of a cell fate control gene pathway in the cell, and wherein the agonist of cell fate control gene pathway function is selected from the group consisting of a Pax protein, a HOX protein, a DLX protein, a Vestigial protein, a PBC protein, a MEINOX protein, a bHLH protein, a LIM homeobox protein, a MSX protein, a POU protein, a PTX protein, a NKX protein, a MADS box protein, a SOX protein, a T-box protein, a WNT protein, a BMP/TGF-β superfamily protein, a hedgehog protein, a nucleic acid encoding a Pax protein, a nucleic acid encoding a HOX protein, a nucleic acid encoding a DLX protein, a nucleic acid encoding a Vestigial protein, a nucleic acid encoding a PBC protein, a nucleic acid encoding a MEINOX protein, a nucleic acid encoding a bHLH protein, a nucleic acid encoding a LIM homeobox protein, a nucleic acid encoding a MSX protein, a nucleic acid encoding a POU protein, a nucleic acid encoding a PTX protein, a nucleic acid encoding a NKX protein, a nucleic acid encoding a MADS box protein, a nucleic acid encoding a SOX protein, a nucleic acid encoding a T-box protein, a nucleic acid encoding a WNT protein, a nucleic acid encoding a BMP/TGF-β superfamily protein, and a nucleic acid encoding a hedgehog protein; and (c) after steps (a) and (b), subjecting the cell to conditions that allow cell fate determination to occur, thereby altering the cell fate otherwise adopted by the cell.

3. The method according to claim 2 comprising introducing into the cell one or more nucleic acids encoding an agonist of Notch pathway function and an agonist of a cell fate control gene pathway function such that the agonists are expressed by the cell.

4. The method according to claim 2 in which the agonist of cell fate control gene pathway function is a Pax protein or a nucleic acid encoding a Pax protein.

5. The method according to claim 4 in which the Pax protein is selected from the group consisting of human or mouse Pax-1, Pax-2, Pax-3, Pax-4, Pax-5, Pax-6, Pax-7, Pax-8 or Pax-9 and *Drosophila* Eyeless and Twin of Eyeless.

6. The method according to claim 2 in which the agonist of cell fate control gene pathway function is a Hox protein or a nucleic acid encoding a Hox protein.

7. The method according to claim 6 in which the Hox protein is selected from the group consisting of Mammalian Hox A1-7, Hox A9-11; HoxA13; Hox B1-9; Hox C4-6; Hox C8-13; Hox D1, Hox D3-4; Hox D8-13; and *Drosophila* Lab, Pb, Dfd, Scr, Antp, Ubx, Abd-A and Abd-B.

8. The method according to claim 2 in which the agonist of cell fate control gene pathway function is selected from the group consisting of a DLX protein, a nucleic acid encoding a DLX protein, LIM homeobox protein, a nucleic acid encoding a LIM homeobox protein, PBC protein, a nucleic acid encoding a PBC protein, MEINOX protein, a nucleic acid encoding a MEINOX protein, POU protein, a nucleic acid encoding a POU protein, PTX protein, a nucleic acid encoding a PTX protein, NKX protein, and a nucleic acid encoding a NKX protein.

9. The method according to claim 2 in which the agonist of cell fate control gene pathway function is selected from the group consisting of a Vestigial protein, a nucleic acid encoding a Vestigial protein, MADS domain protein, a nucleic acid encoding a MADS domain protein, bHLH protein, a nucleic acid encoding a bHLH protein, SOX protein, a nucleic acid encoding a SOX protein, T-box protein, and a nucleic acid encoding a T-box protein.

10. The method according to claim 2 wherein the agonist of cell fate control gene pathway function is selected from the group consisting of a Hedgehog protein, a nucleic acid encoding a Hedgehog protein, a WNT protein or a nucleic acid encoding a WNT protein, a TGF-β/BMP protein, and a nucleic acid encoding a TGF-β/BMP protein.

11. The method according to claim 2 which further comprises expanding the cell by subjecting the cell to cell growth conditions to produce a population of cells.

12. The method according to claim 2 wherein the altering of cell fate is a change in tissue or organ type.

13. The method according to claim 2 wherein the cell is a mammalian cell.

14. The method according to claim 13 wherein the cell is a human cell.

15. The method according to claim 2 wherein the agonist of Notch pathway function and the agonist of cell fate control gene pathway function are purified.

16. The method according to claim 2, wherein the cell fate produced by said method is apoptosis.

17. The method according to claim 15 wherein the cell is a human cell.

18. The method according to claim 16 wherein the cell is a cancer cell.

19. The method according to claim 17, wherein the cell fate that would have been otherwise adopted by said cell is apoptosis.

20. The method according to claim 2 wherein the agonist of Notch pathway function is a dominant-active Notch mutant.

21. The method according to claim 2 wherein the agonist of Notch pathway function is purified.

22. The method according to claim 2 wherein the agonist of Notch pathway function is a dominant-active Notch mutant and the agonist of cell fate control gene pathway function is a HOX protein or a nucleic acid encoding a HOX protein.

23. The kit according to claim 1 wherein the agonist of Notch pathway function is a dominant-active Notch mutant and the agonist of cell fate control gene pathway function is a HOX protein or a nucleic acid encoding a HOX protein.

* * * * *